(12) United States Patent
Roein Peikar et al.

(10) Patent No.: US 11,864,974 B2
(45) Date of Patent: Jan. 9, 2024

(54) DENTAL APPLIANCES, SYSTEMS AND METHODS

(71) Applicant: Brius Technologies, Inc., Addison, TX (US)

(72) Inventors: Seyed Mehdi Roein Peikar, Addison, TX (US); James Sylvester Wratten, Jr., Waterville, NY (US)

(73) Assignee: BRIUS TECHNOLOGIES, INC., Carrollton, TX (US)

( * ) Notice: Subject to any disclaimer, the term of this patent is extended or adjusted under 35 U.S.C. 154(b) by 4 days.

(21) Appl. No.: 16/865,323

(22) Filed: May 2, 2020

(65) Prior Publication Data

US 2020/0345460 A1 Nov. 5, 2020

Related U.S. Application Data

(60) Provisional application No. 62/842,391, filed on May 2, 2019.

(51) Int. Cl.
| | |
|---|---|
| *A61C 7/14* | (2006.01) |
| *A61C 7/00* | (2006.01) |
| *A61C 7/20* | (2006.01) |

(52) U.S. Cl.
CPC ............. *A61C 7/146* (2013.01); *A61C 7/002* (2013.01); *A61C 7/145* (2013.01); *A61C 7/20* (2013.01)

(58) Field of Classification Search
CPC ........... A61C 7/02; A61C 7/145; A61C 7/146; A61C 7/10
See application file for complete search history.

(56) References Cited

U.S. PATENT DOCUMENTS

| | | |
|---|---|---|
| 659,577 A | 10/1900 | Cederstrom |
| 1,292,702 A | 1/1919 | Canning |

(Continued)

FOREIGN PATENT DOCUMENTS

| | | |
|---|---|---|
| AU | 2016367144 B2 | 10/2021 |
| AU | 2021290322 A1 | 2/2022 |

(Continued)

OTHER PUBLICATIONS

International Search Report and Written Opinion dated Aug. 6, 2020, International Application No. PCT/2020/031211, 28 pages.

(Continued)

*Primary Examiner* — Ralph A Lewis
(74) *Attorney, Agent, or Firm* — FORTEM IP LLP; Mary Fox; Katrina Marcelo

(57) ABSTRACT

An orthodontic appliance and associated systems and methods are disclosed herein. In some embodiments, the present technology includes a positioning member configured to position an orthodontic appliance during installation in the patient's mouth. The positioning member may comprise a first portion configured to be coupled to the patient's teeth and a second portion extending away from the first portion. The second portion may be configured to be detachably coupled to the orthodontic appliance. While the positioning member is coupled to the orthodontic appliance, the positioning member is configured to be positioned in the patient's mouth and coupled to the patient's teeth, thereby positioning the orthodontic appliance at a desired location adjacent a patient's oral anatomy.

18 Claims, 54 Drawing Sheets

(56) References Cited

U.S. PATENT DOCUMENTS

| | | |
|---|---|---|
| 1,369,665 A | 2/1921 | Johnson |
| 2,259,160 A | 10/1941 | Glaser |
| 2,266,860 A * | 12/1941 | Griesinger .............. A61C 7/00 433/7 |
| 2,305,916 A | 12/1942 | Atkinson |
| 2,926,422 A | 3/1960 | Melvin |
| 3,235,965 A | 2/1966 | Muir |
| 3,256,602 A | 6/1966 | Broussard et al. |
| 3,262,207 A | 7/1966 | Kesling |
| 3,416,228 A | 12/1968 | Grimmett |
| 3,421,221 A | 1/1969 | Silverman et al. |
| 3,464,112 A | 9/1969 | Silverman et al. |
| 3,464,113 A | 9/1969 | Silverman et al. |
| 3,505,736 A | 4/1970 | Brader et al. |
| 3,510,340 A | 5/1970 | Blake et al. |
| 3,593,421 A | 7/1971 | Brader |
| 3,618,214 A | 11/1971 | Armstrong |
| 3,738,005 A | 6/1973 | Cohen et al. |
| 3,762,050 A | 10/1973 | Dal |
| 3,792,529 A | 2/1974 | Goshgarian |
| 3,815,237 A | 6/1974 | Wallshein |
| 3,936,938 A | 2/1976 | Northcutt |
| 4,037,324 A | 7/1977 | Andreasen |
| 4,197,643 A | 4/1980 | Burstone et al. |
| 4,354,834 A | 10/1982 | Wilson |
| 4,360,342 A | 11/1982 | Salvo |
| 4,433,960 A | 2/1984 | Garito et al. |
| 4,468,196 A | 8/1984 | Keller |
| 4,479,779 A | 10/1984 | Wool |
| 4,516,938 A | 5/1985 | Hall |
| 4,533,320 A | 8/1985 | Piekarsky |
| 4,571,179 A | 2/1986 | Balenseifen |
| 4,731,018 A | 3/1988 | Adell |
| 4,815,968 A | 3/1989 | Keller |
| 4,932,866 A | 6/1990 | Guis |
| 4,976,614 A | 12/1990 | Tepper |
| 5,022,855 A | 6/1991 | Jeckel |
| 5,120,218 A | 6/1992 | Hanson |
| 5,167,499 A | 12/1992 | Arndt et al. |
| 5,255,352 A | 10/1993 | Falk |
| 5,295,886 A | 3/1994 | Wildman |
| 5,310,340 A | 5/1994 | Zedda |
| 5,312,247 A | 5/1994 | Sachdeva et al. |
| 5,380,197 A | 1/1995 | Hanson |
| 5,429,501 A | 7/1995 | Farzin-Nia et al. |
| 5,431,562 A | 7/1995 | Andreiko et al. |
| 5,435,721 A | 7/1995 | Vogt |
| 5,536,169 A | 7/1996 | Yousefian |
| 5,580,243 A | 12/1996 | Bloore |
| 5,645,423 A | 7/1997 | Collins |
| 5,791,897 A | 8/1998 | Wildman |
| 5,829,980 A | 11/1998 | Sheridan et al. |
| 5,975,893 A | 11/1999 | Chishti et al. |
| 6,053,730 A | 4/2000 | Cleary |
| 6,086,364 A | 7/2000 | Brunson |
| 6,174,163 B1 | 1/2001 | Hiro |
| 6,190,166 B1 | 2/2001 | Sasakura |
| 6,220,856 B1 | 4/2001 | Carano et al. |
| 6,254,384 B1 | 7/2001 | Rosenberg |
| 6,302,688 B1 | 10/2001 | Jordan et al. |
| 6,582,226 B2 | 6/2003 | Jordan et al. |
| 6,732,558 B2 | 5/2004 | Butscher et al. |
| 6,739,870 B2 | 5/2004 | Lai et al. |
| 6,755,064 B2 | 6/2004 | Butscher et al. |
| 6,860,132 B2 | 3/2005 | Butscher et al. |
| 6,884,067 B2 | 4/2005 | Tuneberg |
| 6,908,306 B2 | 6/2005 | Bowman et al. |
| 6,928,733 B2 | 8/2005 | Rubbert et al. |
| 6,935,858 B2 | 8/2005 | Cleary |
| 6,984,127 B2 | 1/2006 | Lai |
| 7,020,963 B2 | 4/2006 | Cleary et al. |
| 7,056,115 B2 | 6/2006 | Phan et al. |
| 7,063,531 B2 | 6/2006 | Maijer et al. |
| 7,076,980 B2 | 7/2006 | Butscher et al. |
| 7,131,836 B1 | 11/2006 | Kesling |
| 7,210,929 B2 | 5/2007 | Raby et al. |
| 7,234,934 B2 | 6/2007 | Rosenberg |
| 7,240,528 B2 | 7/2007 | Weise et al. |
| 7,283,891 B2 | 10/2007 | Butscher et al. |
| 7,291,011 B2 | 11/2007 | Stark et al. |
| 7,335,021 B2 | 2/2008 | Nikodem |
| 7,347,688 B2 | 3/2008 | Kopelman et al. |
| 7,354,268 B2 | 4/2008 | Raby et al. |
| 7,357,634 B2 | 4/2008 | Knopp |
| 7,416,407 B2 | 8/2008 | Cronauer |
| 7,433,810 B2 | 10/2008 | Pavloskaia et al. |
| 7,556,496 B2 | 7/2009 | Cl et al. |
| 7,578,673 B2 | 8/2009 | Wen et al. |
| 7,580,846 B2 | 8/2009 | Chishti et al. |
| 7,600,999 B2 | 10/2009 | Knopp |
| 7,613,527 B2 | 11/2009 | Raby et al. |
| 7,641,473 B2 | 1/2010 | Sporbert et al. |
| 7,658,610 B2 | 2/2010 | Knopp |
| 7,708,557 B2 | 5/2010 | Rubber |
| 7,726,968 B2 | 6/2010 | Raby et al. |
| 7,785,102 B2 * | 8/2010 | Papadopoulos .......... A61C 7/10 433/21 |
| 7,837,466 B2 | 11/2010 | Griffith et al. |
| 7,869,983 B2 | 1/2011 | Raby et al. |
| 7,940,258 B2 | 5/2011 | Stark et al. |
| 7,993,133 B2 | 8/2011 | Cinader et al. |
| RE42,815 E | 10/2011 | Rubbert et al. |
| 8,192,196 B2 | 6/2012 | Singh |
| 8,194,067 B2 | 6/2012 | Raby et al. |
| 8,266,940 B2 | 9/2012 | Riemeier et al. |
| 8,292,617 B2 | 10/2012 | Brandt et al. |
| 8,308,478 B2 | 11/2012 | Primus et al. |
| 8,326,647 B2 | 12/2012 | Chishti et al. |
| 8,356,993 B1 | 1/2013 | Marston |
| 8,382,917 B2 | 2/2013 | Johnson |
| 8,401,686 B2 | 3/2013 | Moss et al. |
| 8,417,366 B2 | 4/2013 | Getto et al. |
| 8,496,473 B2 | 7/2013 | Phan et al. |
| 8,517,726 B2 | 8/2013 | Kakavand et al. |
| 8,517,727 B2 | 8/2013 | Raby et al. |
| 8,529,253 B2 | 9/2013 | Jasper |
| 8,550,814 B1 | 10/2013 | Collins |
| RE44,668 E | 12/2013 | Rubbert et al. |
| 8,606,598 B2 | 12/2013 | Chishti et al. |
| 8,685,184 B2 | 4/2014 | Johnson et al. |
| 8,734,149 B2 | 5/2014 | Phan et al. |
| 8,801,633 B2 | 8/2014 | Fox et al. |
| 8,827,697 B2 | 9/2014 | Cinader et al. |
| 8,932,054 B1 | 1/2015 | Rosenberg |
| 8,944,812 B2 | 2/2015 | Kuo |
| 8,992,215 B2 | 3/2015 | Chapoulaud et al. |
| 9,017,070 B2 | 4/2015 | Parker |
| 9,061,124 B2 | 6/2015 | Fox et al. |
| 9,127,338 B2 | 9/2015 | Johnson |
| 9,149,344 B2 | 10/2015 | Gautam |
| 9,168,113 B2 | 10/2015 | Wu et al. |
| 9,204,942 B2 | 12/2015 | Phan et al. |
| 9,220,580 B2 | 12/2015 | Borovinskih et al. |
| 9,326,831 B2 | 5/2016 | Cheang |
| 9,328,406 B2 | 5/2016 | Johnson et al. |
| 9,375,300 B2 | 6/2016 | Matov et al. |
| 9,427,291 B2 | 8/2016 | Khoshnevis et al. |
| 9,433,479 B2 | 9/2016 | Phan et al. |
| 9,498,302 B1 | 11/2016 | Patel |
| 9,504,544 B2 | 11/2016 | Conley et al. |
| 9,532,854 B2 | 1/2017 | Cinader et al. |
| 9,554,875 B2 | 1/2017 | Gualano |
| 9,566,133 B2 | 2/2017 | Yu |
| 9,572,971 B2 | 2/2017 | Su |
| 9,610,628 B2 | 4/2017 | Riemeier et al. |
| 9,757,211 B2 | 9/2017 | Ward |
| 9,844,420 B2 | 12/2017 | Cheang |
| 9,883,924 B2 | 2/2018 | Rudman |
| 9,925,019 B2 | 3/2018 | Cinader et al. |
| 9,925,025 B2 | 3/2018 | Conley et al. |
| 9,937,018 B2 | 4/2018 | Martz et al. |
| 10,022,204 B2 | 7/2018 | Cheang |
| 10,052,174 B2 | 8/2018 | Kitching et al. |
| 10,154,890 B2 | 12/2018 | Johnson et al. |

(56) References Cited

U.S. PATENT DOCUMENTS

| | | |
|---|---|---|
| 10,226,312 B2 | 3/2019 | Khoshnevis et al. |
| 10,278,791 B2 | 5/2019 | Schumacher |
| 10,363,116 B2 | 7/2019 | Boronkay |
| 10,383,707 B2 | 8/2019 | Roein Peikar et al. |
| 10,413,386 B2 | 9/2019 | Moon et al. |
| 10,478,271 B2 * | 11/2019 | Patel .............. A61C 7/10 |
| 10,729,516 B2 * | 8/2020 | Hung .............. A61C 7/08 |
| 10,905,527 B2 | 2/2021 | Roein Peikar et al. |
| 10,980,614 B2 | 4/2021 | Roein Peikar et al. |
| 10,993,785 B2 | 5/2021 | Roein Peikar et al. |
| 11,058,518 B2 * | 7/2021 | Roein Peikar .......... A61C 7/22 |
| 11,058,520 B2 | 7/2021 | Khoshnevis et al. |
| 11,317,994 B2 | 5/2022 | Roein Peikar et al. |
| 11,317,995 B2 | 5/2022 | Roein Peikar et al. |
| 11,324,572 B2 | 5/2022 | Roein Peikar et al. |
| 11,529,216 B2 | 12/2022 | Roein Peikar et al. |
| 2003/0075186 A1 | 4/2003 | Florman |
| 2003/0091952 A1 * | 5/2003 | Bowman .............. A61C 7/10 433/7 |
| 2003/0096210 A1 | 5/2003 | Rubbert et al. |
| 2003/0118967 A1 | 6/2003 | Tepper |
| 2003/0224310 A1 | 12/2003 | Andreiko |
| 2004/0009449 A1 | 1/2004 | Mah et al. |
| 2004/0048222 A1 | 3/2004 | Forster et al. |
| 2004/0067463 A1 | 4/2004 | Rosenberg |
| 2004/0072120 A1 | 4/2004 | Lauren |
| 2004/0131989 A1 | 7/2004 | Dellinger |
| 2004/0214126 A1 * | 10/2004 | Forster .............. A61C 7/10 433/7 |
| 2005/0130094 A1 | 6/2005 | Graham |
| 2005/0227196 A1 | 10/2005 | Von |
| 2005/0239012 A1 | 10/2005 | Bathen et al. |
| 2005/0244780 A1 | 11/2005 | Abels et al. |
| 2006/0073436 A1 | 4/2006 | Raby et al. |
| 2006/0234179 A1 | 10/2006 | Wen et al. |
| 2007/0087302 A1 | 4/2007 | Reising et al. |
| 2007/0259301 A1 | 11/2007 | Hagelganz et al. |
| 2007/0264605 A1 * | 11/2007 | Belfor .............. A61C 7/00 433/6 |
| 2008/0020339 A1 * | 1/2008 | Papadopoulos .......... A61C 7/00 433/21 |
| 2008/0032258 A1 | 2/2008 | Kyung et al. |
| 2008/0057460 A1 | 3/2008 | Hicks |
| 2008/0233528 A1 | 9/2008 | Kim et al. |
| 2008/0254403 A1 | 10/2008 | Hilliard |
| 2008/0311535 A1 | 12/2008 | Andreiko |
| 2009/0098500 A1 | 4/2009 | Diaz |
| 2010/0068671 A1 | 3/2010 | Kakavand et al. |
| 2010/0075268 A1 | 3/2010 | Duran |
| 2010/0279245 A1 | 11/2010 | Navarro |
| 2011/0027743 A1 | 2/2011 | Cinader et al. |
| 2011/0269095 A1 | 11/2011 | Singh |
| 2012/0048432 A1 | 3/2012 | Johnson et al. |
| 2012/0123577 A1 | 5/2012 | Chapoulaud et al. |
| 2012/0225398 A1 | 9/2012 | Fallah |
| 2012/0322019 A1 | 12/2012 | Lewis |
| 2013/0081271 A1 | 4/2013 | Farzin-Nia et al. |
| 2013/0252195 A1 * | 9/2013 | Popat .............. A61C 7/10 433/7 |
| 2014/0120491 A1 | 5/2014 | Khoshnevis et al. |
| 2014/0154637 A1 | 6/2014 | Hansen et al. |
| 2014/0234794 A1 | 8/2014 | Vu |
| 2014/0302448 A1 | 10/2014 | Cassalia |
| 2014/0356799 A1 | 12/2014 | Cinader et al. |
| 2015/0157421 A1 | 6/2015 | Martz et al. |
| 2015/0245888 A1 | 9/2015 | Hasegawa |
| 2015/0257856 A1 | 9/2015 | Martz et al. |
| 2016/0058527 A1 | 3/2016 | Schumacher |
| 2016/0095670 A1 | 4/2016 | Witte et al. |
| 2016/0095672 A1 | 4/2016 | Izadi |
| 2016/0106520 A1 | 4/2016 | Borovinskih et al. |
| 2016/0135926 A1 | 5/2016 | Djamchidi |
| 2016/0278882 A1 * | 9/2016 | Kitching .............. A61C 7/08 |
| 2016/0302890 A1 | 10/2016 | Hamilton |
| 2016/0324601 A1 | 11/2016 | Phan et al. |
| 2016/0346064 A1 * | 12/2016 | Schulhof .............. A61C 7/002 |
| 2017/0100215 A1 | 4/2017 | Khouri |
| 2017/0156823 A1 | 6/2017 | Roein Peikar et al. |
| 2017/0245963 A1 | 8/2017 | Hirsch |
| 2017/0296304 A1 | 10/2017 | Tong et al. |
| 2018/0014916 A1 | 1/2018 | Cinader et al. |
| 2018/0021108 A1 | 1/2018 | Cinader et al. |
| 2018/0049847 A1 | 2/2018 | Oda et al. |
| 2018/0071057 A1 | 3/2018 | Rudman |
| 2018/0142377 A1 | 5/2018 | Gao et al. |
| 2018/0153651 A1 | 6/2018 | Tong et al. |
| 2018/0185125 A1 | 7/2018 | Salah et al. |
| 2018/0221113 A1 | 8/2018 | Tong et al. |
| 2018/0303583 A1 | 10/2018 | Tong et al. |
| 2018/0311014 A1 * | 11/2018 | Yousefian .............. A61C 7/10 |
| 2018/0325629 A1 | 11/2018 | Cursio |
| 2018/0338564 A1 | 11/2018 | Oda et al. |
| 2018/0353265 A1 | 12/2018 | Paehl et al. |
| 2019/0015178 A1 | 1/2019 | Wiechmann |
| 2019/0069974 A1 | 3/2019 | Schumacher |
| 2019/0090985 A1 | 3/2019 | Jo |
| 2019/0090988 A1 | 3/2019 | Schumacher et al. |
| 2019/0090989 A1 | 3/2019 | Jo |
| 2019/0321138 A1 | 10/2019 | Roein Peikar et al. |
| 2020/0078140 A1 | 3/2020 | Roein Peikar et al. |
| 2020/0085540 A1 | 3/2020 | Roein Peikar et al. |
| 2020/0085541 A1 | 3/2020 | Roein Peikar et al. |
| 2020/0107911 A1 | 4/2020 | Roein Peikar |
| 2020/0129272 A1 | 4/2020 | Roein Peikar et al. |
| 2020/0345455 A1 | 11/2020 | Roein Peikar et al. |
| 2020/0375699 A1 | 12/2020 | Roein Peikar et al. |
| 2020/0390524 A1 | 12/2020 | Roein Peikar et al. |
| 2021/0007830 A1 | 1/2021 | Roein Peikar et al. |
| 2021/0007832 A1 | 1/2021 | Roein Peikar et al. |
| 2021/0169616 A1 | 6/2021 | Jo |
| 2021/0177551 A1 | 6/2021 | Roein Peikar et al. |
| 2021/0186662 A1 | 6/2021 | Roein Peikar et al. |
| 2021/0353389 A1 | 11/2021 | Roein Peikar et al. |
| 2022/0133438 A1 | 5/2022 | Wratten et al. |
| 2022/0226076 A1 | 7/2022 | Roein Peikar et al. |
| 2022/0226077 A1 | 7/2022 | Roein Peikar et al. |
| 2022/0287804 A1 | 9/2022 | Oda |

FOREIGN PATENT DOCUMENTS

| | | |
|---|---|---|
| CA | 2511247 C | 6/2009 |
| CN | 201079455 Y | 7/2008 |
| CN | 101277658 A | 10/2008 |
| CN | 104146786 A | 11/2014 |
| CN | 104887332 A | 9/2015 |
| CN | 106491221 A | 3/2017 |
| CN | 207949917 U | 10/2018 |
| CN | 211271270 U | 8/2020 |
| DE | 102015009345 A1 | 1/2016 |
| EP | 0400932 A3 | 1/1991 |
| EP | 0551800 A1 | 7/1993 |
| EP | 1379193 B1 | 2/2007 |
| EP | 1769772 A2 | 4/2007 |
| EP | 1301140 B1 | 11/2010 |
| EP | 2881075 A1 | 6/2015 |
| EP | 3383309 A1 | 10/2018 |
| EP | 3581145 A1 | 12/2019 |
| EP | 3649981 A1 | 5/2020 |
| GB | 974100 A | 11/1964 |
| GB | 2521046 A | 6/2015 |
| JP | H0634607 U | 5/1994 |
| JP | H08280711 A | 10/1996 |
| JP | 2002102256 A | 4/2002 |
| JP | 2003204973 A | 7/2003 |
| JP | 2005110830 A | 4/2005 |
| JP | 2005177161 A | 7/2005 |
| JP | 2006246978 A | 9/2006 |
| JP | 2009504247 A | 2/2009 |
| JP | 2011517603 A | 6/2011 |
| KR | 20180107481 A | 10/2018 |
| SU | 1502023 A1 | 8/1989 |
| WO | 01/80761 A2 | 11/2001 |
| WO | 2007021468 A2 | 2/2007 |

(56) References Cited

FOREIGN PATENT DOCUMENTS

| | | |
|---|---|---|
| WO | 2009126433 A2 | 10/2009 |
| WO | 2010146192 A1 | 12/2010 |
| WO | 2011103669 A1 | 9/2011 |
| WO | 2014088422 A1 | 6/2014 |
| WO | 2014140013 A1 | 9/2014 |
| WO | 2015032918 A1 | 3/2015 |
| WO | 2016149007 A1 | 9/2016 |
| WO | 2016149008 A1 | 9/2016 |
| WO | 2017081637 A1 | 5/2017 |
| WO | 2017100198 A1 | 6/2017 |
| WO | 2018215863 A1 | 11/2018 |
| WO | 2019043005 A1 | 3/2019 |
| WO | 2019064127 A1 | 4/2019 |
| WO | 2020223714 A1 | 11/2020 |
| WO | 2020223744 A1 | 11/2020 |
| WO | 2020223745 A1 | 11/2020 |
| WO | 2020223745 A9 | 11/2020 |
| WO | 2021226618 A1 | 11/2021 |
| WO | 2021252675 A1 | 12/2021 |
| WO | 2022099267 A1 | 5/2022 |
| WO | 2022246420 A1 | 11/2022 |

OTHER PUBLICATIONS

International Search Report and Written Opinion dated Aug. 26, 2020, International Application No. PCT/US20/70017, 12 pages.

International Search Report and Written Opinion dated Oct. 8, 2020, International Application No. PCT/US20/70016, 18 pages.

Extended European Search Report dated Jul. 24, 2019, from Application No. 16873680.9.

International Report on Patentability dated Jun. 21, 2018, from Application No. PCT/US2016/065174.

International Search Report and Written Opinion dated Mar. 13, 2017, from related International Application No. PCT/US2016/065174.

Khosravi, Rooz, "Biomechanics in lingual orthodontics: What the future holds", Seminars in Orthodontics, vol. 24, No. 3, 2018, 363-371.

International Search Report dated Jul. 19, 2021 for International Patent Application No. PCT/US21/70469. 14 pages.

Baron Pascal, et al., "Customized Brackets and the Straight Arch Technique Combined in One Appliance to Simplify Lingual Orthodontics", J. Dentofacial Anom Orthod, 2012, pp. 1-16.

Faber Zackary, "Incognito Customized Orthodontic Appliance: A Giant Leap Forward in Orthodontic Technology", Dentistry iQ, 2012, pp. 1-5.

Gracco Antonio, et al., "The Insignia System of Customized Orthodontics", JCO, Inc., 2011, pp. 442-451.

Kusy Robert, "Orthodontic Biomaterials: From the Past to the Present", The Angle Orthodontist, 2002, pp. 501-512.

Miankar Mugdha, et al., "Precision Multiloop (PM Design) with Space Closing Circles for Lingual Orhodontics", Journal of Indian Orthodontic Society, 2016, pp. S88-S93.

Miura Fujio, et al., "New Application of Superelastic NiTi Rectangular Wire", J. Clin. Orthod., 1990, pp. 544-548.

Raboud D.W., "Superelastic Response to NiTi Shape Memory Alloy Wires for Orthodontic Applications", Smart Materials and Stuctures, 2000, pp. 684-692.

Ribeiro Gerson Luiz Ulema, et al., "Multiloop Edgewise Archwire in the Treatment of a Patient with an Anterior Open Bite and a Long Face", American Journal of Orthodontics and Dentofacial Orthopedics, 2010, pp. 89-95.

Sanjay N., et al., "Space Closure with Loop Mechanics for Treatment of Bimaxillary Protrusion: A Case Report", Journal of International Oral Health, 2015, pp. 65-67.

Siatkowski Raymond, "Continuous Arch Wire Closing Loop Design, Optimization, and Verification. Part 1", American Journal of Orthodontics and Dentofacial Orthopedics, 1997, pp. 393-408.

Teramoto Alberto, "Sentalloy the Story of Superelasticity", Materials Science, 2012, pp. 1-12.

Viecilli Amanda, et al., "The T-Loop in Details", Dental Press J. Orthod., 2018, pp. 108-117.

Werner Alison, "MEAW Therapy", Orthodontic Products, https://orthodonticproductsonline.com/clinical-tips/meaw-therapy/, 2012, pp. 1-7.

Wiechmann Dirk, et al., "Customized Brackets and Archwire for Lingual Orthodontic Treatment", American Journal of Orthodontics and Dentofacial Orthopedics, 2003, pp. 593-599.

Yang Won-Sik, et al., "A Study of the Regional Load Deflection Rate of Multiloop Edgewise Arch Wire", The Angle Orthodontist, 2001, pp. 103-109.

International Search Report and Written Opinion dated Mar. 28, 2022; International Application No. PCT/US2021/072214; 18 pages.

KR20180107481A (Yoon Sung Hee; Oh Yoon Joon) (Biocetec Co Ltd) Self ligation orthodontic bracket assembly, Oct. 2, 2018. [retrieved on May 26, 2022], Translation retrieved from: Espacenet (Year: 2018).

International Search Report and Written Opinion dated Sep. 15, 2022; International Application No. PCT/US2022/072399; 14 pages.

* cited by examiner

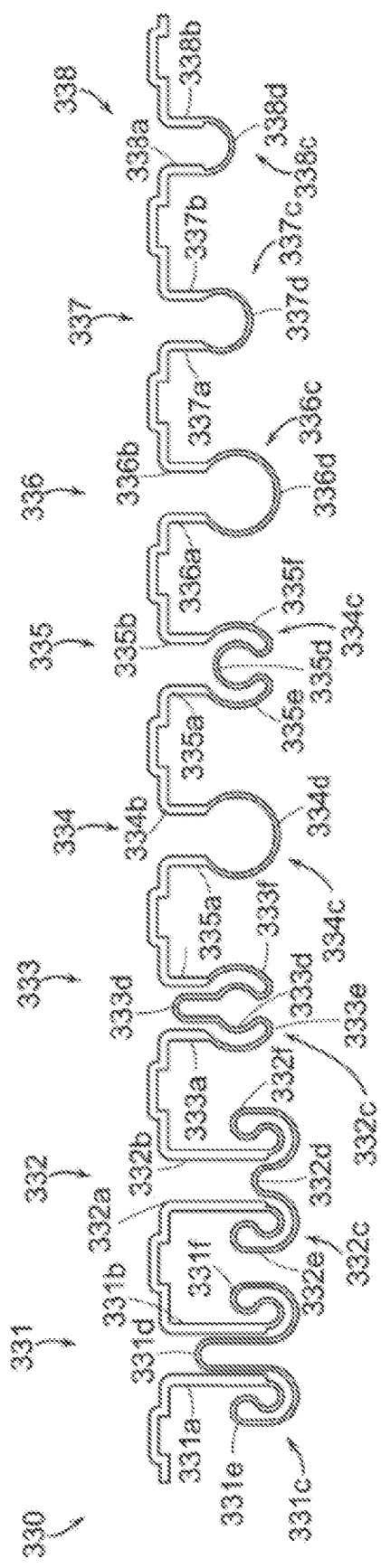
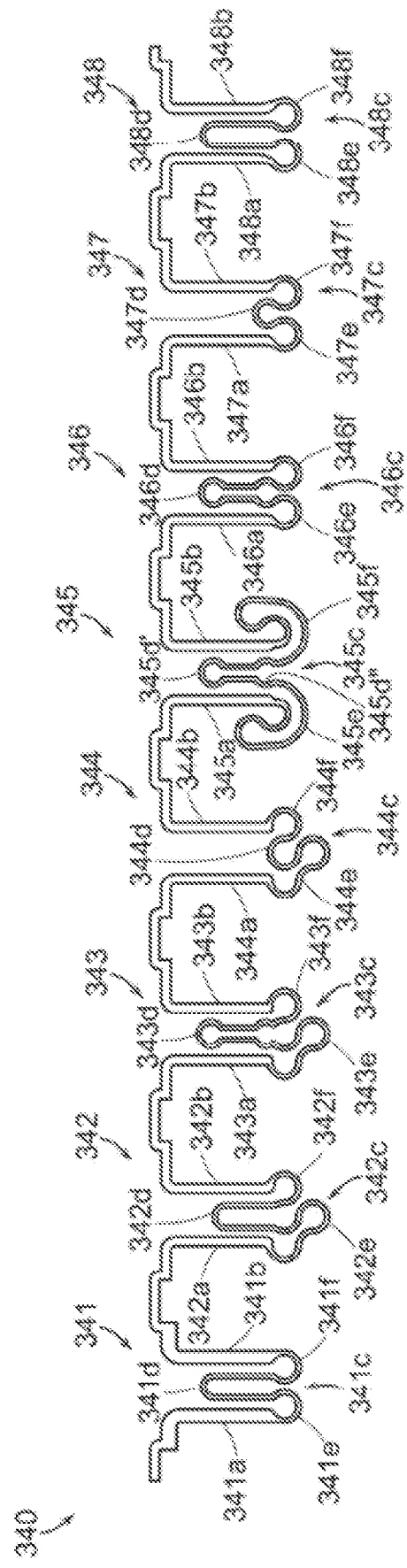
FIG. 36
FIG. 37

DENTAL APPLIANCES, SYSTEMS AND METHODS

CROSS-REFERENCE TO RELATED PATENT APPLICATIONS

The present application claims the benefit of priority to U.S. Patent Application No. 62/842,391, filed May 2, 2019, which is incorporated by reference herein in its entirety.

The present application incorporates by reference herein U.S. patent application Ser. No. 15/370,704, filed Dec. 5, 2016, U.S. Provisional Application No. 62/263,659, filed Dec. 6, 2015, U.S. Provisional Application No. 62/352,025, filed Jun. 20, 2016, and U.S. Provisional Application No. 62/393,526, filed Sep. 12, 2016, in their entireties.

BACKGROUND OF THE INVENTION

1. Field of Invention

Present embodiments relate generally to appliances, appliance members for making appliances, systems and methods for making appliances and appliance members, and systems and methods for repositioning teeth, including orthodontic systems and methods that include or employ one or more appliances that are installed (in a removable or non-removable manner) on a patient's teeth. Further embodiments relate to components of appliances and appliance members, additional elements that may be employed with an appliance (including installation units, platforms, aligners and retainers), and systems and methods that include combinations of appliances or appliance members and one or more of such additional elements.

2. Background

In orthodontics, repositioning the teeth for aesthetic or other purposes has been performed by orthodontic devices traditionally referred to as braces. Braces are typically composed of brackets, archwires, O-rings and ligature wires. In addition to braces that typically have an appliance in front of the teeth, other methods include lingual orthodontics (which employs an appliance behind the teeth) and clear aligners such as Invisalign™ aligners (which employ transparent polymeric shells over the teeth).

SUMMARY OF THE DISCLOSURE

Embodiments described herein relate to systems and methods for repositioning teeth and include or employ one or more appliances that are installed (in a removable or non-removable manner) on a patient's teeth.

According to an example, an appliance for installing on a patient's teeth includes at least one first rigid segment having a length dimension, and at least one second rigid segment having a length dimension, wherein each of the first and second rigid segments is configured to extend along two or more adjacent teeth in a jaw of the patient when the appliance is installed. At least one arm extends from the at least one first rigid segment. At least one loop or curved feature is formed along the length dimension of the second segment. The appliance further includes a plurality of bracket connectors, where each bracket connector is configured to selectively connect to a bracket that may be secured to respective one of the patient's teeth. The plurality of bracket connectors includes at least one first bracket connector on the at least one arm and at least one second bracket connector on the at least one second rigid segment.

In an appliance according to a further example, the first and second rigid segments are configured to extend along the same two or more adjacent teeth in the jaw of the patient when the appliance is installed.

In an appliance according to a further example, the at least one first rigid segment is configured to extend along a different set of two or more adjacent teeth in the jaw of the patient relative to the teeth that the at least one second rigid segment is configured to extend along, when the appliance is installed.

In an appliance according to a further example, at least a portion of the first segment includes an arch shaped member having an arch shape or partial arch shape and configured to extend along two or more adjacent teeth in the patient's jaw.

In an appliance according to a further example, the at least one arm includes a first arm extending from the first rigid segment to a first one of the first bracket connectors, and a second arm extending from the first rigid segment to a second one of the first bracket connectors, and wherein the at least one second rigid segment extends from the first one of the first bracket connectors to the second one of the first bracket connectors.

In an appliance according to a further example, the at least one second bracket connector includes a plurality of second bracket connectors located along the at least one second rigid segment, between the first one of the first bracket connectors to the second one of the first bracket connectors.

In an appliance according to a further example, the at least one first bracket connector includes one or more further bracket connectors on the at least one first rigid segment.

In an appliance according to a further example, each of the first arm and the second arm includes a spring member.

In an appliance according to a further example, the at least one second rigid segment has a length dimension extending from one end of the arch shaped member of the first rigid segment.

In an appliance according to a further example, the at least one arm extending from the at least one first rigid segment includes a plurality of arms, the at least one first bracket connector includes a plurality of first bracket connectors on the plurality of arms, and the at least one second bracket connectors include a plurality of bracket connectors along the length dimension of the second rigid segment.

In an appliance according to a further example, the at least one second rigid segment has a length dimension extending from a second end of the arch shaped member of the first rigid segment.

In an appliance according to a further example, the at least one arm extending from the at least one first rigid segment includes a plurality of arms, the at least one first bracket connector includes a plurality of first bracket connectors on the plurality of arms, and the at least one second bracket connector includes a plurality of bracket connectors along the length dimension each of the second rigid segments.

In an appliance according to a further example, the at least one arm includes a first arm extending from the first rigid segment to a first one of the first bracket connectors, and a second arm extending from the first rigid segment to a second one of the first bracket connectors, and wherein the at least one second rigid segment extends from the first one of the first bracket connectors to the second one of the first bracket connectors.

In an appliance according to a further example, the at least one arm includes at least one additional arm located along the length of the first rigid segment between the first arm and the second arm, each additional arm extending from the first rigid segment to a respective further one of the first bracket connectors located between the first one of the first bracket connectors and the second one of the second bracket connectors.

In an appliance according to a further example, at least a portion of the second rigid segment includes an arch shaped member having an arch shape or partial arch shape and configured to extend along two or more adjacent teeth in the patient's jaw.

According to an example, an appliance for installing on a patient's teeth includes at least one first rigid segment having a length dimension, and at least one second rigid segment having a length dimension, wherein at least one of the first and second rigid segments is configured to extend along two or more adjacent teeth in a jaw of the patient when the appliance is installed. The appliance further includes at least one arm extending from the at least one first rigid segment and at least one loop or curved feature formed along the length dimension of the second rigid segment. The appliance further includes a plurality of bracket connectors, each bracket connector configured to selectively connect to a bracket that may be secured to respective one of the patient's teeth, the bracket connectors being provided along the length dimension of the second rigid segment, the bracket connectors including at least one bracket connector connected to the at least one arm extending from the at least one first rigid segment.

In that appliance according to a further example, the at least one arm includes a spring member located between the at least one first rigid segment and the bracket connector to which the at least one arm is connected.

In that appliance according to a further example, two or more of the bracket connectors are connected to two or more of the arms extending from the at least one first rigid segment.

In that appliance according to a further example, each of the two or more of the arms includes a spring member located between the at least one first rigid segment and the bracket connector to which the arm is connected.

In that appliance according to a further example, the appliance is configured as single, unitary structure from a single sheet of material.

According to an example, an appliance system includes an appliance for installing on a patient's teeth, where the appliance includes at least one rigid segment having a length dimension configured to extend along two or more adjacent teeth in a jaw of the patient when the appliance is installed. At least one bracket connector is supported by the at least one rigid segment and is configured to selectively connect to a tooth bracket. The at least one bracket connector includes a body portion having first and second arm sections that connect to each other at an interface and that each have a free end, the body portion being sufficiently flexible and resilient to allow the free ends of the first and second arm sections to be forced to move toward each other into a compressed state when a sufficient squeezing force is applied to the first and second arm sections, and to resiliently move back away from each other from the squeezed state to an uncompressed or partially uncompressed state when the force is removed. At least part of the body portion has a first width dimension when the first and second arm sections are in the compressed state and a second width dimension when the first and second arm sections are in the uncompressed state, and wherein the second width dimension is greater than the first width dimension.

In that appliance system according to a further example, the body portion is configured to be received by the bracket when the first and second arm sections are in the compressed state, and to be locked to the bracket in which it is received, when the first and second arm sections are in the uncompressed state.

In that appliance system according to a further example, the interface at which the first and second arm sections connect to each other is a U-shaped interface.

In that appliance system according to a further example, each of the first and second arm sections has a free end and one or more projections extending from the arm section at or near the free end.

In that appliance system according to a further example, each of the first and second arm sections has a free end and a plurality of projections extending from the arm section at or near the free end.

That appliance system according to a further example, further includes the bracket, including a base configured to be secured to a tooth. A plurality of projections extend from the base, including at least two projections arranged to define a gap between the at least two projections, wherein the gap has a size sufficient to receive the first and second arm sections of the bracket connector between the at least two projections when the first and second arm sections are in the compressed state, and wherein the plurality of projections extending from each arm section are arranged to extend on two respective sides of one of the two projections when the first and second arm sections are received in the gap and in the un-compressed state.

That appliance system according to another example, further includes the bracket, including a base configured to be secured to a tooth, where a plurality of projections extend from the base, including at least two projections arranged to define a gap between the at least two projections.

In that appliance system according to a further example, the gap has a size sufficient to receive the body portion between the at least two projections when the first and second arm sections are in the compressed state, and to be locked to the bracket in which it is received, when the first and second arm sections are in the uncompressed state.

In that appliance system according to a further example, each of the at least two projections has an extension, extending in a direction away from the gap.

In that appliance system according to a further example, the at least two projections includes a plurality of projections on a first side of the gap and a plurality of projections on the second side of the gap.

In that appliance system according to a further example, the plurality of projections on the first side of the gap include first and second projections that are spaced apart by a distance at least as great as a width dimension of a projection extending from the first or second arm section.

That appliance system according to a further example, includes either (a) at least one arm extending from the at least one first rigid segment, (b) at least one loop or curved feature formed along the length dimension of the second rigid segment, or (c) at least one arm extending from the at least one first rigid segment and at least one loop or curved feature formed along the length dimension of the second rigid segment.

In that appliance system according to a further example, the appliance is configured as single, unitary structure from a single sheet of material.

According to an example, a bracket connector for a dental appliance includes a body portion having first and second arm sections that connect to each other at an interface and that each have a free end. The body portion is sufficiently flexible and resilient to allow the free ends of the first and second arm sections to be forced to move toward each other into a compressed state when a sufficient squeezing force is applied to the first and second arm sections, and to resiliently move back away from each other from the squeezed state to an uncompressed or partially uncompressed state when the force is removed. At least part of the body portion has a first width dimension when the first and second arm sections are in the compressed state and a second width dimension when the first and second arm sections are in the uncompressed state, wherein the second width dimension is greater than the first width dimension.

In the bracket connector according to a further example, the body portion is configured to be received by a bracket when the first and second arm sections are in the compressed state, and to be locked to the bracket in which it is received, when the first and second arm sections are in the uncompressed state.

In the bracket connector according to a further example, the interface at which the first and second arm sections connect to each other is a U-shaped interface.

In the bracket connector according to a further example, each of the first and second arm sections has a free end and one or more projections extending from the arm section at or near the free end.

In the bracket connector according to a further example, each of the first and second arm sections has a free end and a plurality of projections extending from the arm section at or near the free end.

In the bracket connector according to a further example, the bracket connector is configured as single, unitary structure from a single sheet of material.

According to another example, a bracket connector for a dental appliance includes a base configured to be secured to a tooth, and a plurality of projections extending from the base, including at least two projections arranged to define a gap between the at least two projections. The gap has a size sufficient to receive the first and second arm sections of the bracket connector between the at least two projections when the first and second arm sections are in the compressed state. The plurality of projections extending from each arm section are arranged to extend on two respective sides of one of the two projections when the first and second arm sections are received in the gap and in the un-compressed state.

According to another example, an orthodontic appliance system includes an appliance for installing on a patient's teeth, where the appliance is configured to extend along two or more adjacent teeth in a jaw of the patient when the appliance is installed. The appliance has at least one platform connector element. The system also includes an anchoring platform for installing on the patient's maxilla or mandible. The anchoring platform has at least one appliance connector element configured to selectively connect with the at least one platform connector element of the appliance.

In that system according to a further example, the appliance includes at least one first rigid segment and at least one platform connector arm extending from the at least one first rigid segment, and wherein the at least one platform connector element of the appliance is provided on the at least one arm.

In that system according to a further example, the appliance includes at least one further arm extending from the at least one first rigid segment and a bracket connector on each further arm. Each bracket connector is configured to selectively connect to a bracket that may be secured to respective one of the patient's teeth.

In that system according to a further example, the appliance includes a plurality of further arms extending from the at least one first rigid segment and a plurality of bracket connectors including a bracket connector on each further arm. Each bracket connector is configured to selectively connect to a bracket that may be secured to respective one of the patient's teeth.

In that system according to a further example, the at least one platform connector element includes at least one Y shaped member having laterally projecting end portions configured to be received within corresponding apertures of the at least one appliance connector element.

In that system according to a further example, the anchoring platform includes at least one anchorage connector element configured to receive at least one temporary anchoring device (TAD) for holding the anchoring platform onto the patient's maxilla.

In that system according to a further example, the anchoring platform includes at least one anchorage connector element configured to receive at least one temporary anchoring device (TAD) for holding the anchoring platform onto the patient's mandible.

In that system according to a further example, the anchoring platform includes an annular body configured to be installed on the patient's mandible.

In that system according to a further example, the anchoring platform further includes at least one anchorage connector element extending from the annular body and configured to receive at least one temporary anchoring device (TAD) for holding the anchoring platform onto the patient's mandible.

In that system according to a further example, the anchoring platform further includes a plurality of anchorage connector elements extending from the annular body and configured to receive at least one temporary anchoring device (TAD) for holding the anchoring platform onto the patient's mandible, the plurality of anchorage connector elements including one or more first anchorage connector elements extending inward from the annular body toward a central area surrounded by the annular body.

In that system according to a further example, the plurality of anchorage connector elements further includes one or more second anchorage connector elements extending outward from the annular body toward an area outside of the annular body.

In that system according to a further example, the anchoring platform further includes a plurality of anchorage connector elements extending from the annular body and configured to receive at least one temporary anchoring device (TAD) for holding the anchoring platform onto the patient's mandible. The plurality of anchorage connector elements include one or more anchorage connector elements extending outward from the annular body toward an area outside of the annular body.

In that system according to a further example, the anchoring platform includes a plate-like body configured to be installed on the patient's mandible.

In that system according to a further example, the plate-like body of the anchoring platform further includes at least one opening through which at least one temporary anchoring device (TAD) may extend for holding the anchoring platform onto the patient's mandible.

In that system according to a further example, the plate-like body of the anchoring platform has a convex surface for abutting against a patient's palate and a concave surface facing opposite to the convex surface.

In that system according to a further example, the plate-like body of the anchoring platform is configured to correspond to an impression mold of the patient's palate.

In that system according to a further example, the anchoring platform further includes one or more appliance connector elements extending from the concave surface, and configured to selectively connect with the one or more platform connector elements of the appliance.

An example of a method of making an orthodontic appliance system includes configuring an appliance for installing on a patient's teeth, to extend along two or more adjacent teeth in a jaw of the patient when the appliance is installed. The method further includes providing the appliance with at least one platform connector element, configuring an anchoring platform for installing on the patient's maxilla or mandible, and providing the anchoring platform with at least one appliance connector element configured to selectively connect with the at least one platform connector element of the appliance.

In that method, according to a further example, configuring the appliance includes configuring at least one first rigid segment and at least one platform connector arm extending from the at least one first rigid segment, wherein the at least one platform connector element of the appliance is provided on the at least one arm.

In that method, according to a further example, configuring the appliance includes configuring includes at least one further arm extending from the at least one first rigid segment, and providing a bracket connector on each further arm, wherein each bracket connector is configured to selectively connect to a bracket that may be secured to respective one of the patient's teeth.

According to a further example, the method further includes providing the anchoring platform with at least one anchorage connector element configured to receive at least one temporary anchoring device (TAD) for holding the anchoring platform onto the patient's maxilla.

According to a further example, the method further includes providing the anchoring platform with at least one anchorage connector element or opening configured to receive at least one temporary anchoring device (TAD) for holding the anchoring platform onto the patient's mandible.

In that method, according to a further example, providing the anchoring platform includes forming an annular body configured to be installed on the patient's mandible.

In that method, according to a further example, providing the anchoring platform includes forming a plate-like body configured to be installed on the patient's mandible.

An example of an installation unit for installing an orthodontic appliance or a platform on a patient, includes a body portion having a shape that corresponds to one or more (or a plurality of) teeth in one of the patient's jaws. The body portion is configured to hold an appliance during installation of the appliance on the patient's teeth, and wherein the body portion includes a plurality of connection sections for temporarily connecting with the orthodontic appliance during installation, the plurality of connection sections being configured to release the appliance from the body portion, after the appliance is installed on the patient.

An installation unit according to a further example further includes at least one wire or tie member for temporarily connecting the orthodontic appliance to the plurality of connection sections.

An installation unit according to a further example further includes at least one slot or receptacle in or between the plurality of connection sections, for receiving and temporarily holding one or more sections of the orthodontic appliance.

In the installation unit according to a further example, the body portion having a shape corresponding to a plurality of teeth in the patient's jaw.

In the installation unit according to a further example, the body portion has an arch shape corresponding to a dental impression of the patient's jaw.

In the installation unit according to a further example, each connection section includes a hook, tab or finger extension on the body portion.

In the installation unit according to a further example, the body portion has an arch shape and the installation unit further includes a central frame portion extending within the arch shape of the body portion. The central frame portion is configured to hold the platform during installation of the platform on the patient.

In the installation unit according to a further example, the central frame portion includes one or more (or a plurality of) connection sections for temporarily connecting with the platform during installation. The plurality of connection sections are configured to release the platform from the central frame portion, after the platform is installed on the patient.

A method of making an installation unit for installing an orthodontic appliance or a platform on a patient includes forming a body portion having a shape that corresponds to one or more (or a plurality of) teeth in one of the patient's jaws. The body portion is configured to hold an appliance during installation of the appliance on the patient's teeth. The method further includes providing a plurality of connection sections on the body for temporarily connecting with the orthodontic appliance during installation, the plurality of connection sections being configured to release the appliance from the body portion, after the appliance is installed on the patient.

The method according to further examples further includes providing at least one wire or tie member for temporarily connecting the orthodontic appliance to the plurality of connection sections.

The method according to further examples further includes providing at least one slot or receptacle in or between the plurality of connection sections, for receiving and temporarily holding one or more sections of the orthodontic appliance.

In the method according to a further example, the body portion has an arch shape and the method further includes forming a central frame portion that extends within the arch shape of the body portion to hold the platform during installation of the platform on the patient.

In the method according to further examples, forming the central frame portion includes configuring one or more (or a plurality of) connection sections for temporarily connecting with the platform during installation, and to release the platform from the central frame portion after the platform is installed on the patient.

An example of a method of installing an appliance includes providing an installation unit having a body configured in a shape that corresponds to one or more (or a plurality of) teeth in one of the patient's jaws. The method further includes connecting an appliance to the installation unit, and placing the installation unit, having the appliance connected thereto, onto the one or more (or plurality of) teeth in the patient's jaw. The method further includes securing the appliance to the one or more (or plurality of) teeth in the patient's jaw, while the appliance is connected to the installation unit and while the installation unit is on the one or more (or plurality of) teeth. The method further includes disconnecting the appliance from the installation unit, while the appliance is secured to the one or more (or plurality of) teeth in the patient's jaw, and removing the installation unit from the one or more (or plurality of) teeth in the patient's jaw, while the appliance remains secured to the one or more (or plurality of) teeth.

That method according to a further example further includes connecting one or more (or a plurality of) brackets to the appliance before securing the appliance to the one or more (or plurality of) teeth, wherein securing the appliance includes connecting the one or more (or a plurality of) brackets to the one or more (or plurality of) teeth in the patient's jaw while the appliance is connected to the installation unit.

In that method according to a further example, connecting the one or more (or a plurality of) brackets to the one or more (or plurality of) teeth in the patient's jaw includes bonding the one or more (or a plurality of) brackets to the one or more (or plurality of) teeth in the patient's jaw.

In that method according to a further example, connecting an appliance to the installation unit includes providing one or more temporary connectors, and connecting the appliance to the installation unit with the one or more temporary connectors.

In that method according to a further example, the one or more temporary connector elements include one or more wire ties.

In that method according to a further example, connecting an appliance to the installation unit includes extending one or more arms of the appliance through one or more slots or gaps in the installation unit, and wherein disconnecting the appliance from the installation unit includes removing the one or more arms of the appliance from the slots or gaps in the installation unit.

In that method according to a further example, providing an installation unit includes forming or selecting the installation unit body having a shape that corresponds to the one or more (or plurality of) teeth in the patient's jaw, and wherein placing the installation unit onto the one or more (or plurality of) teeth includes fitting the installation unit body over the one or more (or plurality of) teeth.

In that method according to a further example, providing an installation unit includes forming or selecting the installation unit body having an arch shape and a central frame portion that extends within the arch shape of the body to hold a platform during installation of the platform on the patient. That method further includes connecting the platform to the central frame portion before placing the installation unit onto the one or more (or plurality of) teeth in the patient's jaw, installing the platform on the patient after placing the installation unit onto the one or more (or plurality of) teeth in the patient's jaw, and disconnecting the platform from the central frame after installing the platform.

Examples of the present technology include the following:

1. An appliance for installing on a patient's teeth, the appliance comprising:
   at least one first rigid segment having a length dimension, and at least one second rigid segment having a length dimension, wherein each of the first and second rigid segments is configured to extend along two or more adjacent teeth in a jaw of the patient when the appliance is installed;
   at least one arm extending from the at least one first rigid segment;
   at least one loop or curved feature formed along the length dimension of the second segment; and
   a plurality of bracket connectors, each bracket connector configured to selectively
   connect to a bracket that may be secured to respective one of the patient's teeth, the plurality of bracket connectors including at least one first bracket connector on the at least one arm and at least one second bracket connector on the at least one second rigid segment.

2. The appliance of example 1, wherein the first and second rigid segments are configured to extend along the same two or more adjacent teeth in the jaw of the patient when the appliance is installed.

3. The appliance of example 1, wherein the at least one first rigid segment is configured to extend along a different set of two or more adjacent teeth in the jaw of the patient relative to the teeth that the at least one second rigid segment is configured to extend along, when the appliance is installed.

4. The appliance of example 1, wherein at least a portion of the first segment comprises an arch shaped member having an arch shape or partial arch shape and configured to extend along two or more adjacent teeth in the patient's jaw.

5. The appliance of example 4, wherein the at least one arm comprises a first arm extending from the first rigid segment to a first one of the first bracket connectors, and a second arm extending from the first rigid segment to a second one of the first bracket connectors, and wherein the at least one second rigid segment extends from the first one of the first bracket connectors to the second one of the first bracket connectors.

6. The appliance of example 5, wherein the at least one second bracket connector comprises a plurality of second bracket connectors located along the at least one second rigid segment, between the first one of the first bracket connectors to the second one of the first bracket connectors.

7. The appliance of example 6, wherein the at least one first bracket connector comprises one or more further bracket connectors on the at least one first rigid segment.

8. The appliance of example 4, wherein each of the first arm and the second arm includes a spring member.

9. The appliance of example 4, wherein the at least one second rigid segment has a length dimension extending from one end of the arch shaped member of the first rigid segment.

10. The appliance of example 9, wherein the at least one arm extending from the at least one first rigid segment comprises a plurality of arms, the at least one first bracket connector comprises a plurality of first bracket connectors on the plurality of arms, and the at least one second bracket connectors comprise a plurality of bracket connectors along the length dimension of the second rigid segment.

11. The appliance of example 9, wherein the at least one second rigid segment comprises has a length dimension extending from a second end of the arch shaped member of the first rigid segment.

12. The appliance of example 11, wherein the at least one arm extending from the at least one first rigid segment comprises a plurality of arms, the at least one first bracket connector comprises a plurality of first bracket connectors on the plurality of arms, and the at least one second bracket connectors comprise a plurality of bracket connectors along the length dimension each of the second rigid segments.

13. The appliance of example 1, wherein the at least one arm comprises a first arm extending from the first rigid segment to a first one of the first bracket connectors, and a second arm extending from the first rigid segment to a second one of the first bracket connectors, and wherein the at least one second rigid segment extends from the first one of the first bracket connectors to the second one of the first bracket connectors.

14. The appliance of example 13, wherein the at least one arm comprises at least one additional arm located along the length of the first rigid segment between the first arm and the second arm, each additional arm extending from the first rigid segment to a respective further one of the first bracket connectors located between the first one of the first bracket connectors and the second one of the second bracket connectors.

15. The appliance of example 1, wherein at least a portion of the second rigid segment comprises an arch shaped member having an arch shape or partial arch shape and configured to extend along two or more adjacent teeth in the patient's jaw.

16. An appliance for installing on a patient's teeth, the appliance comprising:
  at least one first rigid segment having a length dimension, and at least one second rigid segment having a length dimension, wherein at least one of the first and second rigid segments is configured to extend along two or more adjacent teeth in a jaw of the patient when the appliance is installed;
  at least one arm extending from the at least one first rigid segment;
  at least one loop or curved feature formed along the length dimension of the second rigid segment; and
  a plurality of bracket connectors, each bracket connector configured to selectively connect to a bracket that may be secured to respective one of the patient's teeth, the bracket connectors being provided along the length dimension of the second rigid segment, the bracket connectors including at least one bracket connector connected to the at least one arm extending from the at least one first rigid segment.

17. The appliance of example 16, wherein the at least one arm includes a spring member located between the at least one first rigid segment and the bracket connector to which the at least one arm is connected.

18. The appliance of example 16, wherein two or more of the bracket connectors are connected to two or more of the arms extending from the at least one first rigid segment.

19. The appliance of example 18, wherein each of the two or more of the arms includes a spring member located between the at least one first rigid segment and the bracket connector to which the arm is connected.

20. The appliance of example 1, wherein the appliance is configured as single, unitary structure from a single sheet of material.

21. An appliance system including an appliance for installing on a patient's teeth and comprising:
  at least one rigid segment having a length dimension configured to extend along two or more adjacent teeth in a jaw of the patient when the appliance is installed;
  at least one bracket connector supported by the at least one rigid segment in and configured to selectively connect to a tooth bracket, the at least one bracket connector including:
  a body portion having first and second arm sections that connect to each other at an interface and that each have a free end, the body portion being sufficiently flexible and resilient to allow the free ends of the first and second arm sections to be forced to move toward each other into a compressed state when a sufficient squeezing force is applied to the first and second arm sections, and to resiliently move back away from each other from the squeezed state to an uncompressed or partially uncompressed state when the force is removed;
  wherein at least part of the body portion has a first width dimension when the first and second arm sections are in the compressed state and a second width dimension when the first and second arm sections are in the uncompressed state, and wherein the second width dimension is greater than the first width dimension.

22. The appliance system of example 21, wherein the body portion is configured to be received by the bracket when the first and second arm sections are in the compressed state, and to be locked to the bracket in which it is received, when the first and second arm sections are in the uncompressed state.

23. The appliance system of example 21, wherein the interface at which the first and second arm sections connect to each other is a U-shaped interface.

24. The appliance system of example 21, wherein each of the first and second arm sections has a free end and one or more projections extending from the arm section at or near the free end.

25. The appliance system of example 21, wherein each of the first and second arm sections has a free end and a plurality of projections extending from the arm section at or near the free end.

26. The appliance system of example 25, further comprising the bracket, including a base configured to be secured to a tooth, a plurality of projections extending from the base, including at least two projections arranged to define a gap between the at least two projections, wherein the gap has a size sufficient to receive the first and second arm sections of the bracket connector between the at least two projections when the first and second arm sections are in the compressed state, and wherein the plurality of projections extending from each arm section are arranged to extend on two respective sides of one of the two projections when the first and second arm sections are received in the gap and in the un-compressed state.

27. The appliance system of example 21, further comprising the bracket, including a base configured to be secured to a tooth, a plurality of projections extending from the base, including at least two projections arranged to define a gap between the at least two projections.

28. The appliance system of example 27, wherein the gap has a size sufficient to receive the body portion between the at least two projections when the first and second arm sections are in the compressed state, and to be locked to the bracket in which it is received, when the first and second arm sections are in the uncompressed state.

29. The appliance system of example 27, wherein each of the at least two projections has an extension, extending in a direction away from the gap.

30. The appliance system of example 27, wherein the at least two projections comprises a plurality of projections on a first side of the gap and a plurality of projections on the second side of the gap.

31. The appliance system of example 30, wherein the plurality of projections on the first side of the gap include first and second projections that are spaced apart by a distance at least as great as a width dimension of a projection extending from the first or second arm section.

32. The appliance system of example 21, further comprising either (a) at least one arm extending from the at least one first rigid segment, (b) at least one loop or curved feature formed along the length dimension of the second rigid segment, or (c) at least one arm extending from the at least one first rigid segment and at least one loop or curved feature formed along the length dimension of the second rigid segment.

33. The appliance system of example 21, wherein the appliance is configured as single, unitary structure from a single sheet of material.

34. A bracket connector for a dental appliance comprising:
a body portion having first and second arm sections that connect to each other at an
interface and that each have a free end, the body portion being sufficiently flexible and resilient to allow the free ends of the first and second arm sections to be forced to move toward each other into a compressed state when a sufficient squeezing force is applied to the first and second arm sections, and to resiliently move back away from each other from the squeezed state to an uncompressed or partially uncompressed state when the force is removed;
wherein at least part of the body portion has a first width dimension when the first and second arm sections are in the compressed state and a second width dimension when the first and second arm sections are in the uncompressed state, and wherein the second width dimension is greater than the first width dimension.

35. The bracket connector of example 34, wherein the body portion is configured to be received by a bracket when the first and second arm sections are in the compressed state, and to be locked to the bracket in which it is received, when the first and second arm sections are in the uncompressed state.

36. The bracket connector of example 34, wherein the interface at which the first and second arm sections connect to each other is a U-shaped interface.

37. The bracket connector of example 34, wherein each of the first and second arm sections has a free end and one or more projections extending from the arm section at or near the free end.

38. The bracket connector of example 34, wherein each of the first and second arm sections has a free end and a plurality of projections extending from the arm section at or near the free end.

39. The bracket connector of example 34, wherein the bracket connector is configured as single, unitary structure from a single sheet of material.

40. A bracket for a dental appliance comprising;
a base configured to be secured to a tooth;
a plurality of projections extending from the base, including at least two projections arranged to define a gap between the at least two projections, wherein the gap has a size sufficient to receive the first and second arm sections of the bracket connector between the at least two projections when the first and second arm sections are in the compressed state, and wherein the plurality of projections extending from each arm section are arranged to extend on two respective sides of one of the two projections when the first and second arm sections are received in the gap and in the un-compressed state.

41. An orthodontic appliance system comprising:
an appliance for installing on a patient's teeth, the appliance configured to extend along two or more adjacent teeth in a jaw of the patient when the appliance is installed, the appliance having at least one platform connector element;
an anchoring platform for installing on the patient's maxilla or mandible, the anchoring platform having at least one appliance connector element configured to selectively connect with the at least one platform connector element of the appliance.

42. The system of example 41, wherein the appliance includes at least one first rigid segment and at least one platform connector arm extending from the at least one first rigid segment, and wherein the at least one platform connector element of the appliance is provided on the at least one arm.

43. The system of example 42, wherein the appliance includes at least one further arm extending from the at least one first rigid segment; and a bracket connector on each further arm, each bracket connector configured to selectively connect to a bracket that may be secured to respective one of the patient's teeth.

44. The system of example 42, wherein the appliance includes a plurality of further arms extending from the at least one first rigid segment; and a plurality of bracket connectors including a bracket connector on each further arm, each bracket connector configured to selectively connect to a bracket that may be secured to respective one of the patient's teeth.

45. The system of example 41, wherein the at least one platform connector element comprises at least one Y shaped member having laterally projecting end portions configured to be received within corresponding apertures of the at least one appliance connector element.

46. The system of example 41, wherein the anchoring platform includes at least one anchorage connector element configured to receive at least one temporary anchoring device (TAD) for holding the anchoring platform onto the patient's maxilla.

47. The system of example 41, wherein the anchoring platform includes at least one anchorage connector element configured to receive at least one temporary anchoring device (TAD) for holding the anchoring platform onto the patient's mandible.

48. The system of example 41, wherein the anchoring platform includes an annular body configured to be installed on the patient's mandible.

49. The system of example 48, wherein the anchoring platform further includes at least one anchorage connector element extending from the annular body and configured to receive at least one temporary anchoring device (TAD) for holding the anchoring platform onto the patient's mandible.

50. The system of example 48, wherein the anchoring platform further includes a plurality of anchorage connector elements extending from the annular body and configured to receive at least one temporary anchoring device (TAD) for holding the anchoring platform onto the patient's mandible, the plurality of anchorage connector elements including one or more first anchorage connector elements extending inward from the annular body toward a central area surrounded by the annular body.

51. The system of example 50, wherein the plurality of anchorage connector elements further includes one or more second anchorage connector elements extending outward from the annular body toward an area outside of the annular body.

52. The system of example 48, wherein the anchoring platform further includes a plurality of anchorage connector elements extending from the annular body and configured to receive at least one temporary anchoring device (TAD) for holding the anchoring platform onto the patient's mandible, the plurality of anchorage connector elements including one or more anchorage connector elements extending outward from the annular body toward an area outside of the annular body.

53. The system of example 41, wherein the anchoring platform includes a plate-like body configured to be installed on the patient's mandible.

54. The system of example 53, wherein the plate-like body of the anchoring platform further includes at least one opening through which at least one temporary anchoring device (TAD) may extend for holding the anchoring platform onto the patient's mandible.

55. The system of example 54, wherein the plate-like body of the anchoring platform has a convex surface for abutting against a patient's palate and a concave surface facing opposite to the convex surface.

56. The system of example 55, wherein the plate-like body of the anchoring platform is configured to correspond to an impression mold of the patient's palate.

57. The system of example 55, wherein the anchoring platform further includes one or more appliance connector elements extending from the concave surface, and configured to selectively connect with the one or more platform connector elements of the appliance.

58. A method of making an orthodontic appliance system comprising:
configuring an appliance for installing on a patient's teeth, to extend along two or more adjacent teeth in a jaw of the patient when the appliance is installed; providing the appliance with at least one platform connector element;
configuring an anchoring platform for installing on the patient's maxilla or mandible; providing the anchoring platform with at least one appliance connector element configured to selectively connect with the at least one platform connector element of the appliance.

59. The method of example 58, wherein configuring the appliance comprises configuring at least one first rigid segment and at least one platform connector arm extending from the at least one first rigid segment, and wherein the at least one platform connector element of the appliance is provided on the at least one arm.

60. The method of example 59, wherein configuring the appliance comprises configuring includes at least one further arm extending from the at least one first rigid segment, and providing a bracket connector on each further arm, wherein each bracket connector is configured to selectively connect to a bracket that may be secured to respective one of the patient's teeth.

61. The method of example 58, further comprising providing the anchoring platform with at least one anchorage connector element configured to receive at least one temporary anchoring device (TAD) for holding the anchoring platform onto the patient's maxilla.

62. The method of example 58, further comprising providing the anchoring platform with at least one anchorage connector element or opening configured to receive at least one temporary anchoring device (TAD) for holding the anchoring platform onto the patient's mandible.

63. The method of example 58, wherein providing the anchoring platform comprises forming an annular body configured to be installed on the patient's mandible.

64. The method of example 58, wherein providing the anchoring platform comprises forming a plate-like body configured to be installed on the patient's mandible.

65. An installation unit for installing an orthodontic appliance or a platform on a patient, the installation unit comprising:
a body portion having a shape that corresponds to one or more (or a plurality of) teeth in one of the patient's jaws, wherein the body portion is configured to hold an appliance during installation of the appliance on the patient's teeth, and wherein the body portion includes a plurality of connection sections for temporarily connecting with the orthodontic appliance during installation, the plurality of connection sections being configured to release the appliance from the body portion, after the appliance is installed on the patient.

66. An installation unit of example 65, further comprising at least one wire or tie member for temporarily connecting the orthodontic appliance to the plurality of connection sections.

67. An installation unit of example 65, further comprising at least one slot or receptacle in or between the plurality of connection sections, for receiving and temporarily holding one or more sections of the orthodontic appliance.

68. An installation unit of example 65, wherein the body portion having a shape corresponding to a plurality of teeth in the patient's jaw.

69. An installation unit of example 65, wherein the body portion has an arch shape corresponding to a dental impression of the patient's jaw.

70. An installation unit of example 65, wherein each connection section comprises a hook, tab or finger extension on the body portion.

71. An installation unit of example 65, wherein the body portion has an arch shape and the installation unit further comprises a central frame portion extending within the arch shape of the body portion, the central frame portion is configured to hold the platform during installation of the platform on the patient.

72. An installation unit of example 71, wherein the central frame portion includes one or more (or a plurality of) connection sections for temporarily connecting with the platform during installation, the plurality of connection sections being configured to release the platform from the central frame portion, after the platform is installed on the patient.

73. A method of making an installation unit for installing an orthodontic appliance or a platform on a patient, the method comprising forming a body portion having a shape that corresponds to one or more (or a plurality of) teeth in one of the patient's jaws, wherein the body portion is configured to hold an appliance during installation of the appliance on the patient's teeth; and providing a plurality of connection sections on the body for temporarily connecting with the orthodontic appliance during installation, the plurality of connection sections being configured to release the appliance from the body portion, after the appliance is installed on the patient.

74. The method of example 73, further comprising providing at least one wire or tie member for temporarily connecting the orthodontic appliance to the plurality of connection sections.

75. The method of example 73, further comprising providing at least one slot or receptacle in or between the plurality of connection sections, for receiving and temporarily holding one or more sections of the orthodontic appliance.

76. The method of example 73, wherein the body portion has an arch shape and the method further comprises forming a central frame portion that extends within the arch shape of the body portion to hold the platform during installation of the platform on the patient.

77. The method of example 76, wherein forming the central frame portion comprises configuring one or more (or a plurality of) connection sections for temporarily connecting with the platform during installation, and to release the platform from the central frame portion after the platform is installed on the patient.

78. A method of installing an appliance comprising:
providing an installation unit having a body configured in a shape that corresponds to one or more (or a plurality of) teeth in one of the patient's jaws;
connecting an appliance to the installation unit;
placing the installation unit, having the appliance connected thereto, onto the one or more (or plurality of) teeth in the patient's jaw;
securing the appliance to the one or more (or plurality of) teeth in the patient's jaw, while the appliance is connected to the installation unit and while the installation unit is on the one or more (or plurality of) teeth;
disconnecting the appliance from the installation unit, while the appliance is secured to the one or more (or plurality of) teeth in the patient's jaw; and
removing the installation unit from the one or more (or plurality of) teeth in the patient's jaw, while the appliance remains secured to the one or more (or plurality of) teeth.

79. The method as recited in example 78, further comprising connecting one or more (or a plurality of) brackets to the appliance before securing the appliance to the one or more (or plurality of) teeth, wherein securing the appliance comprises connecting the one or more (or a plurality of) brackets to the one or more (or plurality of) teeth in the patient's jaw while the appliance is connected to the installation unit.

80. The method as recited in example 79, wherein connecting the one or more (or a plurality of) brackets to the one or more (or plurality of) teeth in the patient's jaw comprises bonding the one or more (or a plurality of) brackets to the one or more (or plurality of) teeth in the patient's jaw.

81. The method as recited in example 78, wherein connecting an appliance to the installation unit comprises providing one or more temporary connectors, and connecting the appliance to the installation unit with the one or more temporary connectors.

82. The method as recited in example 81, wherein the one or more temporary connector elements comprise one or more wire ties.

83. The method as recited in example 78, wherein connecting an appliance to the installation unit comprises extending one or more arms of the appliance through one or more slots or gaps in the installation unit, and wherein disconnecting the appliance from the installation unit comprises removing the one or more arms of the appliance from the slots or gaps in the installation unit.

84. The method as recited in example 78, wherein providing an installation unit comprises forming or selecting the installation unit body having a shape that corresponds to the one or more (or plurality of) teeth in the patient's jaw, and wherein placing the installation unit onto the one or more (or plurality of) teeth comprises fitting the installation unit body over the one or more (or plurality of) teeth.

85. The method of example 78, wherein providing an installation unit comprises forming or selecting the installation unit body having an arch shape and a central frame portion that extends within the arch shape of the body to hold a platform during installation of the platform on the patient, and wherein the method further comprises: connecting the platform to the central frame portion before placing the installation unit onto the one or more (or plurality of) teeth in the patient's jaw; installing the platform on the patient after placing the installation unit onto the one or more (or plurality of) teeth in the patient's jaw; and disconnecting the platform from the central frame after installing the platform.

86. A device for guiding installing of an orthodontic appliance in a patient's mouth, the device comprising:
a first portion configured to be coupled to a patient's teeth; and
a second portion extending away from the first portion towards an interior portion of the mouth, the second portion configured to be releasably coupled to the orthodontic appliance,
wherein, while the device is coupled to the orthodontic appliance, the device is configured to be positioned in the patient's mouth such that (a) the orthodontic appliance is proximate the palate and (b) the first portion is coupled to the patient's teeth, thereby positioning the orthodontic appliance at a desired location adjacent the palate.

87. The device of example 86, wherein the first portion and the second portion comprise a unitarily-formed, integral structure.

88. The device of any one of the previous examples, wherein the first portion is a cover configured to be disposed over an occlusal surface of the patient's teeth.

89. The device of any one of the previous examples, wherein the device comprises a transparent material.

90. The device of any one of the previous examples, wherein the second portion of the device includes an indentation complementary to a topography of all or a portion of the orthodontic appliance such that the complementary portion of the orthodontic appliance is configured to be received within the indentation, thereby releasably securing the orthodontic appliance to the device.

91. The device of any one of the previous examples, wherein the device includes one or more openings through while at least a portion of the orthodontic appliance is visible when the orthodontic appliance is coupled to the second portion.

92. A system, comprising:
an appliance configured to be installed within a patient's mouth adjacent the patient's palate; and
a positioning member comprising:
a first portion configured to be coupled to a patient's teeth, and
second portion extending away from the first portion towards an interior portion of the mouth, the second portion configured to be releasably coupled to the appliance,
wherein, while the positioning member is coupled to the appliance, the positioning member is configured to be positioned in the patient's mouth such that (a) the appliance is proximate the palate and (b) the first portion is coupled to the patient's teeth, thereby positioning the appliance at a desired location adjacent the palate.

93. The system of example 92, wherein the appliance includes at least one anchorage connector element configured to receive at least one temporary anchoring device (TAD) for holding the appliance onto the patient's maxilla and/or mandible.

94. The system of any one of the previous examples, wherein the first portion and the second portion of the positioning member comprise a unitarily-formed, integral structure.

95. The system of any one of the previous examples, wherein the first portion of the positioning member is a cover configured to be disposed over an occlusal surface of the patient's teeth.

96. The system of any one of the previous examples, wherein the positioning member comprises a transparent material.

97. The system of any one of the previous examples, wherein the second portion of the positioning member includes an indentation complementary to a topography of all or a portion of the appliance such that the complementary portion of the appliance is configured to be received within the indentation, thereby releasably securing the appliance to the positioning member.

98. The system of any one of the previous examples, wherein the positioning member includes one or more openings through while at least a portion of the appliance is visible when the appliance is coupled to the second portion of the positioning member.

99. A system, comprising:
   a first appliance configured to be installed within a patient's mouth adjacent the patient's teeth to reposition one or more of the teeth;
   a second appliance configured to be installed within a patient's mouth adjacent the patient's palate, the second appliance configured to be coupled to the first appliance; and
   a positioning member comprising:
      a first portion configured to be coupled to a patient's teeth, and
      a second portion extending away from the first portion towards an interior portion of the mouth, the second portion configured to be releasably coupled to the second appliance,
      wherein, while the positioning member is coupled to the second appliance, the positioning member is configured to be positioned in the patient's mouth such that (a) the second appliance is proximate the palate and (b) the first portion is coupled to the patient's teeth, thereby positioning the second appliance at a desired location adjacent the palate.

100. The system of example 99, wherein the second appliance includes at least one anchorage connector element configured to receive at least one TAD for holding the second appliance onto the patient's maxilla and/or mandible.

101. The system of any one of the previous examples, wherein the first portion and the second portion of the positioning member comprise a unitarily-formed, integral structure.

102. The system of any one of the previous examples, wherein the first portion of the positioning member is a cover configured to be disposed over an occlusal surface of the patient's teeth.

103. The system of any one of the previous examples, wherein the positioning member comprises a transparent material.

104. The system of any one of the previous examples, wherein the second portion of the positioning member includes an indentation complementary to a topography of all or a portion of the second appliance such that the complementary portion of the second appliance is configured to be received within the indentation, thereby releasably securing the second appliance to the positioning member.

105. The system of any one of the previous examples, wherein the positioning member includes one or more openings through while at least a portion of the second appliance is visible when the second appliance is coupled to the second portion of the positioning member.

BRIEF DESCRIPTION OF THE DRAWINGS

The above and other aspects and features of the present invention will become more apparent to those skilled in the art from the following detailed description of the example embodiments with reference to the accompanying drawings, in which:

FIG. 36 is a diagram of further examples of loop or curved features and bracket connectors of an appliance.

FIG. 37 is a diagram of further examples of loop or curved features and bracket connectors of an appliance.

DETAILED DESCRIPTION

Figure 1:
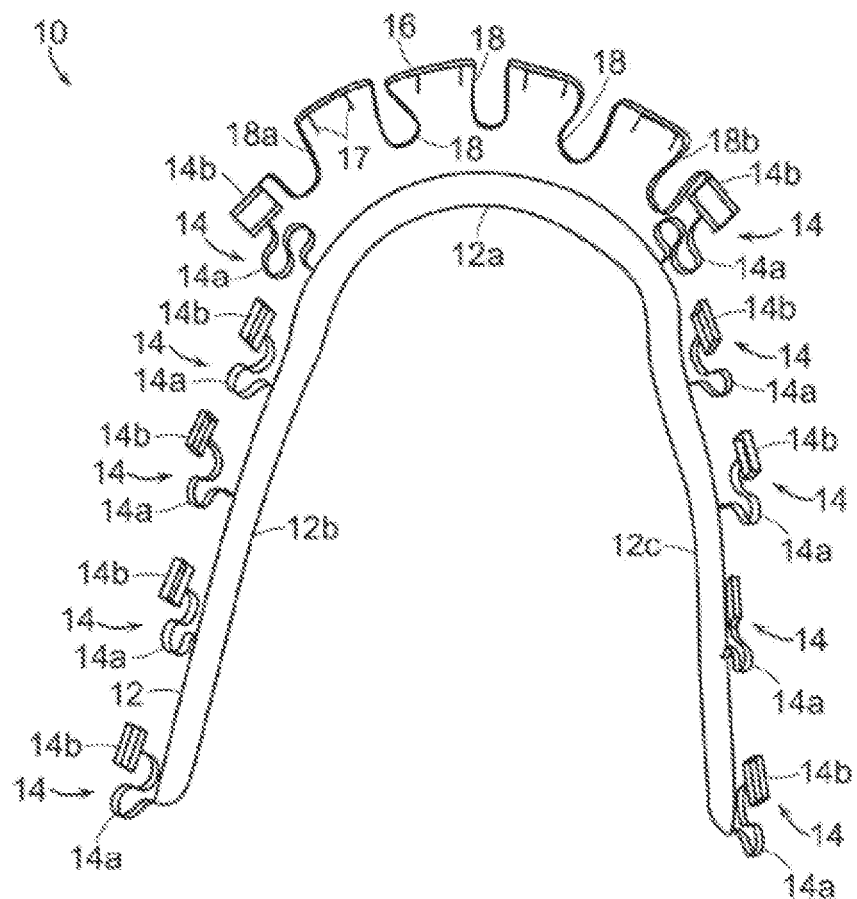
FIG. 1 is a perspective representation of an example appliance.

In the following description of various example embodiments, reference is made to the accompanying drawings which form a part hereof and in which are shown by way of illustration specific examples in which the invention may be practiced. It is to be understood that other examples may be utilized, and structural changes may be made without departing from the scope of the various examples disclosed in the present disclosure.

In the drawings, the relative sizes of elements, layers, and regions may be exaggerated and/or simplified for clarity. Terms, such as "vertical," "vertically," "horizontal," "horizontally," "beneath," "below," "lower," "under," "above," "upper," and the like, may be used herein for ease of explanation (for example, as reference to orientations of elements or features in a drawing figures) to describe one element or feature's relationship to another element(s) or feature(s) as illustrated in the figures. It will be understood that the spatially relative terms are intended to encompass different orientations of the device in use or in operation, in addition to the orientation depicted in the figures, where such different orientations may also be referred to as first and second (and so forth) orientations. As used herein, the term "substantially," "about," and similar terms are used as terms of approximation and not as terms of degree, and are intended to account for the inherent variations in measured or calculated values that would be recognized by those of ordinary skill in the art.

Example embodiments described herein relate to appliances, systems and methods for repositioning teeth. Particular examples relate to appliances, systems and methods for repositioning teeth from an original tooth arrangement (OTA) to a desired final tooth arrangement (FTA). In particular examples, tooth repositioning can be accomplished in one single step, by using one appliance. In other examples, tooth repositioning involves multiple steps performed progressively, by using multiple appliances. Example embodiments involving multiple steps (or multiple appliances, or both) may include one or more intermediate tooth arrangements (ITAs) between an original tooth arrangement (OTA) and a desired final tooth arrangement (FTA).

Example embodiments described herein relate to systems and methods as described in U.S. patent application Ser. No. 15/370,704, filed Dec. 5, 2016, which is incorporated herein, in its entirety. Particular examples described herein may correspond to one or more (or a combination) of appliance and method embodiments described in U.S. patent application Ser. No. 15/370,704, filed Dec. 5, 2016, and may include one or more further features described herein. In other examples, one or more features described herein may be included in other suitable appliances or methods, not limited to the particular examples described in the cited patent application.

Examples described herein may use non-sliding mechanics in which one or more appliances can be installed behind the teeth for aesthetically concerned patients. However, in further examples, appliances or appliance members described herein may employ any suitable mechanics to install one or more appliances behind or in front of the patient's teeth, or both behind and in front of the patient's teeth. The decision of whether or not to place the appliance in front of or behind the teeth is typically made by a clinician, doctor or other trained personnel, with the patient.

Certain examples described herein include or employ a fixed appliance that cannot be removed by the patient once the appliance is installed on the patient's teeth. Other examples described herein include or employ a removable appliance that can be selectively removed and installed on the patient's teeth, by the patient. Examples that include or employ a fixed appliance may require or involve less patient cooperation and training, as compared to examples that include or employ removable orthodontic techniques.

Particular example embodiments described herein allow for computerized design and manufacturing, for example, to design or to custom configure various aspects of one or more appliances, appliance members or additional elements that may be employed with an appliance (including installation units, platforms, aligners and retainers). Computerized design and manufacturing techniques may be employed to design and/or manufacture appliances or appliance members (or portions or components thereof), including one or more (or each) spring, arm, rigid bar, bracket connector, or other feature of the appliance or appliance member, in according to any of the examples described herein. Such computerized design and manufacture may be based on computer input associated with which tooth or teeth is/are to be moved and the desired amount and direction of movement. In particular examples, a computerization of the shape and features of the appliance and/or manufacturing techniques described herein, can provide significant advantages. In particular examples, such computerization can simplify the treatment process for the clinician and can increase treatment precision as compared to traditional techniques. In certain examples, an appliance, appliance member, or components thereof, according to any of the examples described herein may be made, after rearranging a three dimensional (3D) digital OTA to a 3D digital FTA, and designing (via computer aided design or other suitable design techniques) an appliance shape that is configured to impart forces on the patient's teeth to move the teeth from the OTA to the FTA (or to an ITA, or from an ITA to an FTA or another ITA).

Appliances (and components of the appliances) as described herein may be made of any suitable material including, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in a single structure. In certain examples, appliances (or certain components of appliances) are formed in a single, unitary and integral structure, and are not made by connecting separately formed elements together.

Particular examples and features described herein can reduce the number of patient visits to the clinician as well as the chair time for the clinician and the patient. In addition, particular examples can shorten the total treatment time as compared to traditional orthodontics procedures.

One or more appliances and methods described herein may include or be combined with one or more bone anchorage devices including, but not limited to, temporary anchorage devices, mini-plates, implants and the like.

Appliances, appliance members, systems and methods according to examples described herein include some or all of the components and features of any of the appliances, systems and methods of any of the example embodiments described in U.S. patent application Ser. No. 15/370,704, filed Dec. 5, 2016, as well as appliances, systems and methods having other suitable features or configurations. An appliance according to the example embodiments described herein is configured to secure to one or more teeth (or a plurality of teeth or, in some examples, all of the teeth) of an upper jaw or a lower jaw of a patient. In some examples, the appliance includes one or more (or multiple) sections to secure to one or more teeth in both the upper jaw and the lower jaw of the patient.

With systems or methods according to example embodiments described herein, translational orthodontic tooth movement is feasible in one or more, or all three directions of space (i.e. mesiodistal, buccolingual and occlusogingival). Alternatively, or in addition to translational movement of the teeth, one or more, or all three rotational movements including torque, angulation and rotation (i.e. buccolingual root torque, mesiodistal angulation and mesial out-in rotation) are possible.

Systems or methods according to certain examples include or employ an appliance configured to extend along two or more (or a plurality of) adjacent teeth in a patient's jaw (the upper jaw or the lower jaw), when installed. The appliance includes one or more rigid bars that are configured to, individually or together, extend along the two or more (or a plurality of) adjacent teeth. In some examples, an appliance or system of appliances includes one or more rigid bars that is configured to extend along two or more (or a plurality of) adjacent teeth in one of the patient's jaws (e.g., the upper jaw) and a further one or more rigid bars that is configured to extend along two or more (or a plurality of) adjacent teeth in the other one of the patient's jaw (e.g., the lower jaw). Each rigid bar may have sufficient rigidity to hold and maintain its shape and, in particular examples, is sufficiently rigid to resist bending, but may have some flexibility and shape-returning resilience provided by its shape, configuration, and material. In various examples, a rigid bar having a desired amount or degree of rigidity, flexibility and resilience can be determined and designed for a particular patient, or groups of patients (or all patients), by designing or selecting the shape, configuration, material or other characteristics of the rigid bar.

In particular examples, the one or more rigid bars includes an arch-shaped member having an arch shape or partial arch shape that is configured to extend along two or more (or a plurality of) adjacent teeth in a patient's jaw. In other examples, the one or more rigid bars includes a rigid bar having a linear or other suitable shape that extends along two or more (or a plurality of) adjacent teeth in the patient's jaw.

In some examples (referred to herein as examples according to embodiment X), the appliance includes one or more (or a plurality) of separate arms that extend from the one or more rigid bars. Each separate arm is configured to connect to a corresponding one or more of the patient's teeth. In some examples, each arm of the appliance is configured to connect to a different respective tooth relative to each other arm of the appliance. In further examples, the appliance may include one arm configured to connect to a plurality of teeth, or multiple separate arms configured to connect to a corresponding one of the patient's teeth, or various combinations of arm-to-tooth connections. In certain examples, the appliance includes a single rigid bar, to which each of the separate arms is attached. In other examples, the appliance includes more than one rigid bar, with one or more arms attached to each rigid bar. Some examples of appliances according to embodiment X are described with reference to FIGS. 8-11, 18a-18f, and 23a-23b of U.S. patent application Ser. No. 15/370,704, filed Dec. 5, 2016. Other examples of appliances according to embodiment X are described herein.

In further examples (referred to herein as examples according to embodiment Z), the appliance includes additional rigid material (that may form one or more further rigid sections or further rigid bars) having one or more bracket holders (also referred to herein as bracket connectors or male connector elements) and one or more loop or curved feature (force applying feature) formed along the length dimension of the one or more rigid bars. Some examples of appliances according to embodiment Z are described with reference to FIGS. 17a and 17b, 19a-19c, 22a and 22b of U.S. patent application Ser. No. 15/370,704, filed Dec. 5, 2016. Other examples of appliances according to embodiment Z are described herein.

In yet further examples (referred to herein as examples according to embodiment XZ), the appliance includes a combination of X and Z features (including one or more features of one or more examples according to embodiment Z and one or more features of one or more examples according to embodiment X).

An appliance (and methods of making an appliance) configured with a combination of X and Z features can provide significant advantages. For example, an appliance having embodiment X features (including a rigid bar and a plurality of arms extending from the rigid bar) may be desirable for some or all of the teeth in a particular patient's jaw. However, in some cases, it may not be possible to provide an appliance having embodiment X features for the entire jaw. For example, a digital (or computer-generated) scan of the patient's gingiva or jaw may be unclear, incomplete or may not include the patient's entire jaw. In such cases, one or more portions of the appliance may include Z embodiment features to accommodate one or more sections of the patient's jaw, corresponding to the portions of the scans that are unclear, incomplete or missing.

In certain examples, the Z embodiment features may be configured to be located further occlusally (and not extend as far gingivally as certain X embodiment features) when the appliance is installed. Such examples can be beneficial, in contexts in which a patient's scan does not show a complete image of the gingiva, or a part of the patient's anatomy (e.g., a tori) makes it difficult to place a rigid bar of an X embodiment feature on that part of the gingiva.

An appliance having one or more Z embodiment features in combination with X embodiment features may provide other advantages, including, but not limited to, accommodating or fitting the patient's anatomy when the patient has a tori or other growth or anatomical feature in the gingiva, or for accommodating locations where a tooth or teeth have been extracted.

Examples appliances according to embodiment XZ are shown in FIGS. 1-9. Other appliances according to embodiment XZ may have other suitable configurations and combinations of X and Z features.

The example appliance 10 shown in FIG. 1 includes a rigid bar 12 and a plurality of arms 14 extending from the rigid bar 12. The rigid bar 12 is formed in an arch shape (an arch shaped member having a generally arch-shaped configuration). The rigid bar 12 is configured to extend along two or more (or a plurality of) adjacent teeth in one of the patient's jaws, when the appliance 10 is installed, as described herein.

The rigid bar 12 has a lengthwise dimension that includes a section 12a that is configured to extend along the incisor, lateral incisor, and cuspid (canine) teeth. The lengthwise dimension of the rigid bar 12 includes further sections 12b and 12c configured to extend along some or all of the bicuspid and molar teeth. In other embodiments, the rigid bar 12 may be smaller in length and, for example, may include section 12a (or a portion of section 12a), but no sections 12b or 12c. In other embodiments, the rigid bar 12 may include section 12a and a portion of the length of one or each of sections 12b and 12c. In yet other embodiments, the appliance may include one or more rigid bar sections 12b and 12c (of any suitable length) and no section 12a. In yet other embodiments, the appliance may include one or more rigid bar sections 12b and 12c (of any suitable length) and Z embodiment appliance features or other appliance features in the location of section 12a (instead of a rigid bar section 12a) connecting sections 12b and 12c.

The plurality of arms 14 extend from the rigid bar 12, at spaced intervals along the length dimension of the rigid bar 12. The plurality of arms 14 may be spaced at even intervals relative to each other, or at uneven intervals relative to each other, along the length dimension of the rigid bar 12. In particular examples, the arms 14 are provided at locations along the length dimension of the rigid bar 12 that correspond to or are associated with locations of teeth (or, in further particular examples, to the FTA of each tooth) to which the arms connect, when the appliance is installed.

Each arm 14 includes a spring portion (or spring member) 14a and a bracket connector element (or male connector element) 14b. Each spring member 14a in the appliance 10 may correspond to any of the spring members or spring portions on arms described in U.S. patent application Ser. No. 15/370,704, filed Dec. 5, 2016 or herein. Each bracket connector element (or male connector element) 14b in the appliance 10 may correspond to any of the bracket connectors (or male connector elements) described in U.S. patent application Ser. No. 15/370,704, filed Dec. 5, 2016 or herein.

In the example in FIG. 1, the appliance 10 includes ten arms 14 extending from the rigid bar 12, including five arms on the right side and five arms on the left side of the appliance. A respective one of the arms 14 is located at each respective distal end of the rigid bar 12. The five arms on the right side of the appliance 10 are spaced apart and located along the length section 12b, and the five arms on the left side of the appliance 10 are spaced apart and along the length section 12c. of the rigid bar 12 In other examples, the appliance 10 may include fewer or more arms along one or both length sections 12b and 12c. In those or other examples, some or all of the arms 14 may extend from the section 12a of the rigid bar 12.

In the example shown in FIG. 1, the arm 14 closest to the section 12a on the right side of the appliance and the arm 14 closest to the section 12a on the left side of the appliance are, each, connected to (by being either coupled to or integral with) a respective end of a further rigid section of additional rigid material (or second rigid bar) 16. The further rigid section 16 extends along and adjacent to section 12a of the rigid bar 12. In other examples, the further rigid section 16 may also or alternatively extend along and adjacent some or all of the length of section 12b or of section 12c (or of both sections 12b and 12c) of the rigid bar 12. While the appliance 10 in FIG. 1 includes one further rigid section 16, other examples may include two or more further rigid sections of additional rigid material 16 (for example, arranged over and adjacent two or more of the sections 12a, 12b, and 12c, or of portions of those sections).

The further rigid section 16 has a plurality of bracket connectors 17 along its length dimension. The further rigid section 16 also has a plurality of loop or curved features 18 formed along its length dimension.

Each bracket connector 17 may be a bracket connector (or male connector element) corresponding to any of the bracket connectors (or male connector elements) described in U.S. patent application Ser. No. 15/370,704, filed Dec. 5, 2016 or herein. Alternatively, some or all of the bracket connectors 17 may have other suitable bracket connector configurations. In the example of FIG. 1, the bracket connectors 17 have a configuration corresponding to the bracket connectors 266, 267, 268 or 269 described below.

In the example in FIG. 1, four bracket connectors 17 extend from the further rigid section 16. The bracket connectors 17 are spaced apart and located along the length dimension of the further rigid section 16 and, thus, along at least a portion of the corresponding length dimension of section 12a of the rigid bar 12. In other examples, the appliance 10 may include fewer or more bracket connectors 17. In particular examples, the bracket connectors 17 are provided at locations along the length dimension of the further rigid section 16 that correspond to or are associated with locations of teeth to which the bracket connectors 17 connect, when the appliance is installed.

One or more (or each) of the loop or curved features 18 in the further rigid section 16 may be configured to provide a flexibility or a bias or spring force in one or more directions (or both), a force magnitude, durability, or other characteristic, based in part on the shape, material and configuration of the feature 18. In certain examples, as shown in FIG. 1, the appliance 10 includes five loop or curved features 18 along the length of the further rigid section 16. Also, in certain examples, as shown in FIG. 1, one bracket connector 17 is located between each adjacent pair of the loop or curved features 18.

The loop or curved features 18 may include a loop or curved feature 18a located on the left end of the further rigid section 16, and a loop or curved feature 18b located on the right end of the further rigid section 16. In such examples, the further rigid section 16 may connect to arms 14 extending from the rigid bar 12, through the loop or curved feature 18a and 18b. Accordingly, one or both of the loop or curved feature 18a or 18b can be configured to provide one or more of a desired flexibility, bias force magnitude, bias force direction, durability or other characteristics at the interfaces of arms extending from the rigid bar 12 and the further rigid section 16.

In the example in FIG. 1, all of the bracket connectors 17 on the further rigid section 16 are located between the loop or curved features 18a and 18b. In other examples, one or more of the bracket connectors 17 may be located between one or both features 18a or 18b and the respective arms 14 that are connected to the ends of the further rigid section 16.

Other examples may include more or fewer than five loop or curved features along the length of the further rigid section 16, more or fewer than one bracket connector 17 between each adjacent pair of loop or curved features 18, or more than one loop or curved feature 18 between two adjacent bracket connectors 17. The number, configuration and location of the bracket connectors 17 and the loop or curved features 18 may be selected for the appliance 10, to provide (when the appliance is installed) the desired teeth connection positions and desired forces on the teeth, as described herein. For example, the number, configuration and location of the bracket connectors 17 and the loop or curved features 18 may be selected to move one or more teeth from an original tooth arrangement (OTA) to the final tooth arrangement (FTA), or to an intermediate tooth arrangement (ITA), or from an ITA to an FTA or another ITA.

The appliance 10 is configured to be installed on a patient, by coupling the bracket connector elements 14b and bracket connectors 17 to corresponding brackets (or female connector elements) that have been secured to the patient's teeth (or to a selected number of teeth) in one of the patient's jaws. The brackets or female connector elements may have any suitable configuration and may be secured to a patient's teeth in any suitable manner including, but not limited to the configurations and manners of securing described In connection with the brackets or female connector elements at reference numbers 700, 1300, 1501, 1601, 1706, 2600, and 2610 in U.S. patent application Ser. No. 15/370,704, filed Dec. 5, 2016.

The appliance 10 and associated brackets (or female connector elements), may be manufactured in any suitable manners, including, but not limited to any of the manners of manufacturing any of the appliances or brackets (or female connector elements) as described in U.S. patent application Ser. No. 15/370,704, filed Dec. 5, 2016, including, but not limited to molding, casting, machining, 3D printing, stamping, extruding, or the like. However, in particular examples, the appliance 10 or female connector elements (or both) are made by cutting a two dimensional (2D) form of the appliance from a 2D sheet of material and bending the 2D form into a desired 3D shape of the appliance, according to processes as described in U.S. patent application Ser. No. 15/370,704, filed Dec. 5, 2016 or other suitable processes. In those or other examples, the appliance 10 may be configured in a single, unitary structure, from a single sheet (or type) of material. In other examples, the appliance 10 may be configured from multiple components that are coupled together in any suitable manner such as, but not limited to, welds, solder, adhesives, press or friction fitting, mechanical connector, or the like.

In the examples described with reference to FIG. 1, the appliance 10 includes a combination of X and Z features (including one or more features of one or more examples according to embodiment Z and one or more features of one or more examples according to embodiment X). With regard to features according to embodiment X, the appliance 10 includes one or more (or a plurality) of separate arms 14 that extend from the one or more rigid bars 12. With regard to features examples according to embodiment Z, the appliance 10 also includes one or more rigid bars 16 having one or more bracket connectors 17 and one or more loop or curved feature 18 (force applying feature) formed along its length dimension.

Figure 2:
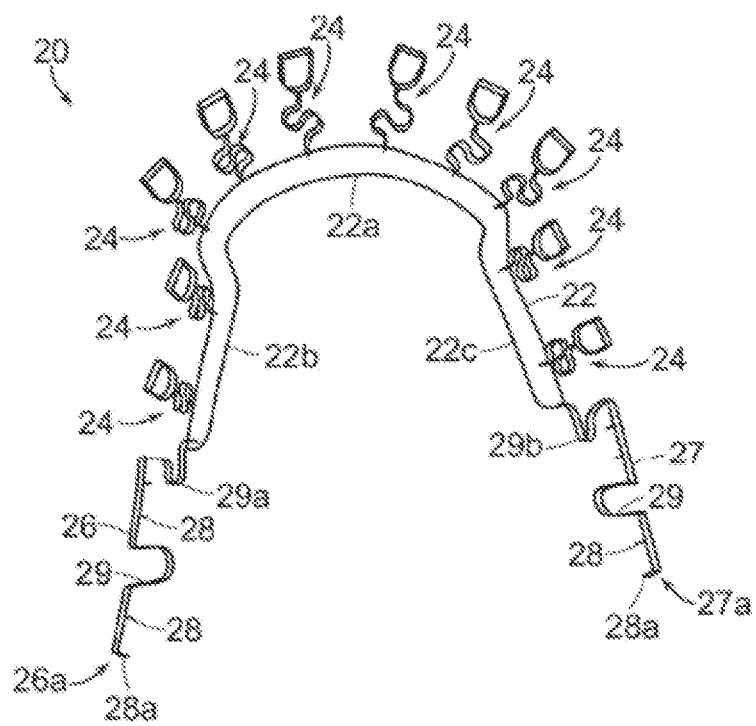
FIG. 2 is a perspective representation of another example appliance.
Figure 3:
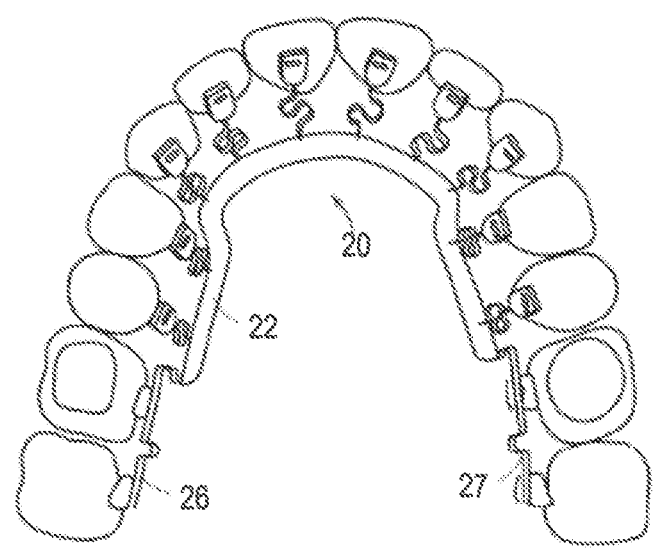
FIG. 3 is a perspective representation of the example appliance of FIG. 2, installed in a patient's mouth.

Another example of an appliance 20 having a combination of X and Z features is shown in FIGS. 2 and 3, and may be made, and used in manners similar or corresponding to such manners described herein for appliance 10. The appliance 20 is shown in FIG. 2, in an un-installed state (not installed on a patient). The appliance 20 is shown in FIG. 3, in an installed state (installed on the teeth of a patient). The appliance 20 includes certain features corresponding in structure or function (or both) to some of the features of appliance 10.

For example, the appliance 20 includes a rigid bar 22 that corresponds to the rigid bar 12 of appliance 10. However, the rigid bar 22 has a lengthwise dimension including a section 22a that is configured to extend along the incisor, lateral incisor, and cuspid (canine) teeth, and further sections 22b and 22c configured to extend along some, but not all of the bicuspid or molar teeth, when the appliance is installed. In other embodiments, the rigid bar 22 may be smaller in length and, for example, may include section 22a (or a portion of section 22a), but no portions of sections 22b or 22c. In other embodiments, the rigid bar 22 may include section 22a and a longer section 22b or a longer section 22c that extend to molar teeth on one side of the appliance 22, when the appliance is installed. The rigid bar 22 may be formed in an arch shape (an arch shaped member having a generally arch-shaped configuration) that is configured to extend along two or more (or a plurality of) adjacent teeth in one of the patient's jaws, when the appliance 20 is installed.

A plurality of arms 24 extend from the rigid bar 22. The arms 24 of the appliance 20 may correspond in structure and function as described with regard to the arms 14 of the appliance 10. For example, the arms 24 may include spring members and bracket connectors (or male connector elements) similar to those described with regard to arms 14 of the appliance 10. The arms 24 may be spaced along the length dimension of the rigid bar 22 in a manner similar to the spacing described with regard to arms 14 on the rigid bar 12. However, in the appliance 20, at least some of the arms 24 are located along the rigid bar section 22a that is configured to extend along some or all of the incisor, lateral incisor, and cuspid (canine) teeth. In other examples, the appliance 20 may include a further rigid section extending along the rigid bar section 22a, or along some or all of the rigid bar sections 22b or 22c (such as, but not limited to the further rigid section 16 of the appliance 10), instead of or in addition to one or more (or all) of the arms 24 located along the rigid bar section 22a (or along sections 22b or 22c).

In the example in FIG. 2, the appliance 20 includes ten arms 24 extending from the rigid bar 22, including six arms extending from the rigid bar section 22a, two arms extending from the rigid bar section 22b and two arms extending from the rigid bar section 22c. In other examples, the appliance 20 may include fewer or more arms along one or more of the length sections 22a, 22b and 22c.

The appliance 20 also includes further rigid sections (or second rigid bars) 26 and 27, extending from the right side end and the left side end, respectively of the rigid bar 22. Each further rigid section 26 and 27 has a lengthwise dimension extending from one end of the rigid bar 22 to a distal end 26a and 27a, respectively. In other examples, the appliance 20 may include one of the further rigid sections 26 or 27, but not the other further rigid section 27 or 26. In those or other examples, the appliance 20 may include one or more further rigid sections (similar to the further rigid sections 26 and 27) located along a portion (or all) of the length of the rigid bar section 22a, instead of (in place of) the rigid bar section 22a.

In the example in FIG. 2, the further rigid section 26 has a shape that corresponds to (or is a mirror image of) the shape of the further rigid section 27. In other examples, the further rigid section 26 may have a shape and configuration that is different from the shape and configuration of the further rigid section 27.

Each further rigid section 26 and 27 has a plurality of bracket connectors 28 and a plurality of loop or curved features 29 formed along its length dimension. The distal end of each further rigid section 26 and 27 may include a portion of a bracket connector 28a. Each of the bracket connectors 28, and loop or curved features 29 may correspond in structure, arrangement and function to any of the various examples described with regard to the bracket connectors 17 and loop or curved features 18 of the appliance 10. In other examples, one or more (or all) of the bracket connectors 28, or features 29 may have other suitable structures, configurations or functions.

In certain examples, such as shown in FIG. 2, the loop or curved features 29 may include a loop or curved feature 29a at or adjacent the location at which the further rigid section 26 extends from the rigid bar 22, and a further loop or curved feature 29b at or adjacent the location at which the further rigid section 27 extends from the rigid bar 22. In such examples, the further rigid sections 26 and 27 may connect to the rigid bar 22, through the loop or curved feature 29a or 29b. In some examples, the loop or curved features 29a and 29b may be a curved or loop feature on an arm extending from the rigid bar 22 (for example, similar to an arm 24). Accordingly, one or both of the loop or curved feature 29a or 29b can be configured to provide one or more of a desired flexibility, bias force magnitude, bias force direction, durability or other characteristics at the interfaces of the rigid bar 22 and the further rigid sections 26 and 27.

In the example in FIG. 2, all of the bracket connectors 28 on the left side of the appliance 20 are located between the loop or curved feature 29a and the distal end 26a of the further rigid section 26. Similarly, all of the bracket connectors 28 on the right side of the appliance 20 are located between the loop or curved feature 29b and the distal end 27a of the further rigid section 27. In other examples, one or more of the bracket connectors 28 may be located between the loop or curved feature 29a or 29b and the rigid bar distal ends 26a or 27a, respectively.

Similar to the appliance 10, the number, configuration and location of the arms 24, bracket connectors 28 and loop or curved features 29 may be selected for the appliance 20, to provide (when the appliance is installed) the desired teeth connection positions and desired forces on the teeth, as described herein. For example, the number, configuration and location of the arms, the bracket connectors, and the loop or curved features may be selected to move one or more teeth from an original tooth arrangement (OTA) to the final tooth arrangement (FTA), or to an intermediate tooth arrangement (ITA), or from an ITA to an FTA or another ITA.

With regard to features according to embodiment X, the appliance 20 includes one or more (or a plurality) of separate arms 24 that extend from the one or more rigid bars 22. With regard to features examples according to embodiment Z, the appliance 20 also includes one or more rigid bars 26 or 27 having one or more bracket connectors 28 and one or more loop or curved feature 29 (force applying feature) formed along its length dimension.

Figure 4:
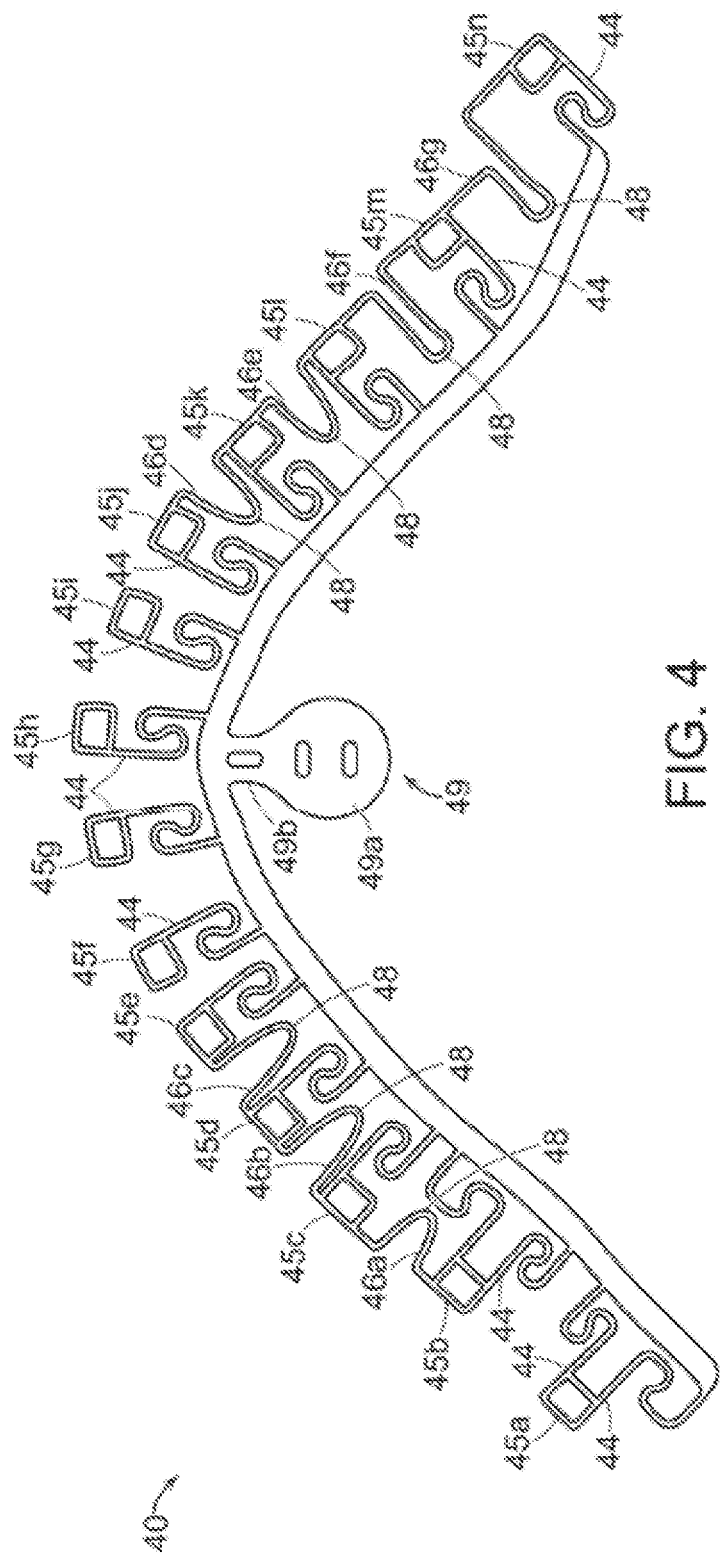
FIG. 4 is a diagram of an example appliance member.

Another example of an appliance having a combination of X and Z features is described with regard to the 2D member 40 for forming an appliance, as shown in FIG. 4. The 2D appliance member 40 in FIG. 4 is configured to be bent or otherwise formed into a 3D appliance in any suitable manner, including processes as described in U.S. patent application Ser. No. 15/370,704, filed Dec. 5, 2016. However, an appliance having features as described with regard to the example in FIG. 4 may be made according to other suitable processes.

An appliance in accordance with the example of FIG. 4 may be made and used in manners similar or corresponding to such manners described herein for appliances 10 and 20. An appliance according to the example of FIG. 4 may include certain features corresponding in structure or function (or both) to some of the features of appliance 10 or appliance 20.

For example, the appliance member 40 includes a rigid bar 42 that corresponds to the rigid bar 12 of appliance 10. The rigid bar 42 has a lengthwise dimension including a section 42a that is configured to extend along the incisor, lateral incisor, and cuspid (canine) teeth, and further sections 42b and 42c configured to extend along some, but not all of the bicuspid or molar teeth, when the appliance formed from the appliance member 40 and is installed. In other embodiments, the rigid bar 42 may be smaller in length and, for example, may include section 42a (or a portion of section 42a), but no portions of sections 42b or 42c. In other embodiments, the rigid bar 42 may include section 42a and a longer section 42b or a longer section 42c that extend to molar teeth on one side of the appliance, when the appliance is formed and installed. In yet other embodiments, the appliance may include a rigid bar 42 having a length dimension, with one or two second rigid bars (or further rigid bar sections) having Z embodiment features (for example, corresponding to the second rigid bars 26 or 27 of the appliance 20).

The rigid bar 42 may have an arch shape (an arch shaped member having a generally arch-shaped configuration) that is configured to extend along two or more (or a plurality of) adjacent teeth in one of the patient's jaws, when the appliance is formed and installed. A plurality of arms 44 extend from the rigid bar 42. The arms 44 may correspond in structure and function as described with regard to the arms 14 or 24 of the appliance 10 or 20. For example, the arms 44 may include spring members and bracket connectors (or male connector elements) similar to those described with regard to arms 14 and 24.

The arms 44 may be spaced along the length dimension of the rigid bar 42 in a manner similar to the spacing described with regard to arms 14 on the rigid bar 12. However, in the appliance member 40, at least some of the arms 44 are located along the rigid bar section 42a that is configured to extend along some or all of the incisor, lateral incisor, and cuspid (canine) teeth. In other examples, the appliance member 40 may include a further rigid section extending along the rigid bar section 42a, or along some or all of the rigid bar sections 42b or 42c (such as, but not limited to the further rigid section 16 of the appliance 10), instead of one or more (or all) of the arms 44 located along the rigid bar section 42a (or along sections 42b or 42c).

In the example in FIG. 4, the appliance member 40 includes sixteen arms 44 extending from the rigid bar 42 to fourteen bracket connectors 45a-45n. One or more (or all) of the bracket connectors may be connected to or part of two respective arms 44, such as shown in FIG. 4 with regard to the bracket connectors 45a and 45b. One or more (or all) of the other bracket connectors may be connected to or part of a single arm 44, such as shown in FIG. 4 with regard to the bracket connectors 45c-45n. In other examples, the appliance member 40 may include fewer or more arms along one or more of the length sections 42a, 42b and 42c. Also, the appliance member 40 of other examples may include fewer or more bracket connectors.

An appliance member according to the example in FIG. 4 includes one or more second rigid bars extending to and between two or more of the bracket connectors. In the example in FIG. 4, the appliance member 40 includes a second rigid bar having segments 46a, 46b and 46c extending between bracket connectors 45b, 45c, 45d and 45e. The appliance 40 includes another second rigid bar having segments 46d, 46e, 46f and 46g extending between the bracket connectors 45j, 45k, 45l, 45m and 45n. In other examples, the number and configuration of second rigid bars and segments 46a-g, and the number and location of bracket connectors 45a-45n to and between which the second rigid bar segments extend, is selected to provide a desired flexibility or force, or both, as described herein.

Each second rigid bar segment 46a-46g may have one or more (or a plurality of) loop or curved features 48 formed along its length dimension. Each of the bracket connectors 45a-45n and loop or curved features 48 may correspond in structure, arrangement and function to any of the various examples described with regard to the bracket connectors 17 and loop or curved features 18 of the appliance 10. In other examples, one or more (or all) of the bracket connectors 45a-45n, or features 48 may have other suitable structures, configurations or functions. One or more of the loop or curved features 48 can be configured to provide one or more of a desired flexibility, bias force strength, bias force direction, between two or more of the bracket connectors 45a-45n.

In certain examples, such as shown in FIG. 4, the appliance member (or appliance) may include an anchor holder, for anchoring the appliance to a patient's palate. In the example in FIG. 4, the appliance member 40 includes an anchor holder 49 or Nance. The anchor holder 49 is connected to (by being either coupled to or integral with) the rigid bar 42. In the example in FIG. 4, the anchor holder 49 has a rounded, plate-shaped head portion 49a connected to the rigid bar 42, through a narrowed neck section 49b. A plurality of apertures is provided in the head portion 49a and the neck portion 49b of the anchor holder 49. When the appliance is formed and installed, one or more temporary anchorage devices TADs (or other suitable anchorage devices) may be extended through the one or more apertures in the anchor holder 49, and into the patient's palate (soft and hard tissue), to anchor the appliance to the patient's palate. In particular examples, the anchor holder 49 is for soft tissue anchorage, where soft tissue is used to help anchor the appliance. In some examples, the appliance member (or appliance), including the anchor holder, may lay against the soft tissue in the patient's palate, without the use of TADs (or other suitable anchoring devices), when the appliance is installed. In other examples, TADs or other suitable anchor holders may be employed. An anchor holder (such as, but not limited to the anchor holder 49) may be included in any of the example embodiments described herein.

Figure 5:
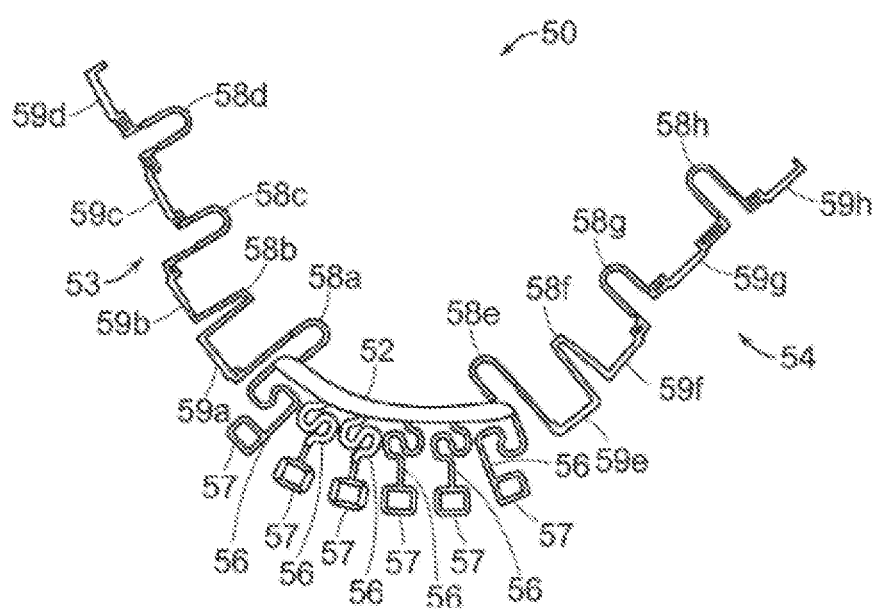
FIG. 5 is a diagram of another example appliance member.
Figure 6:
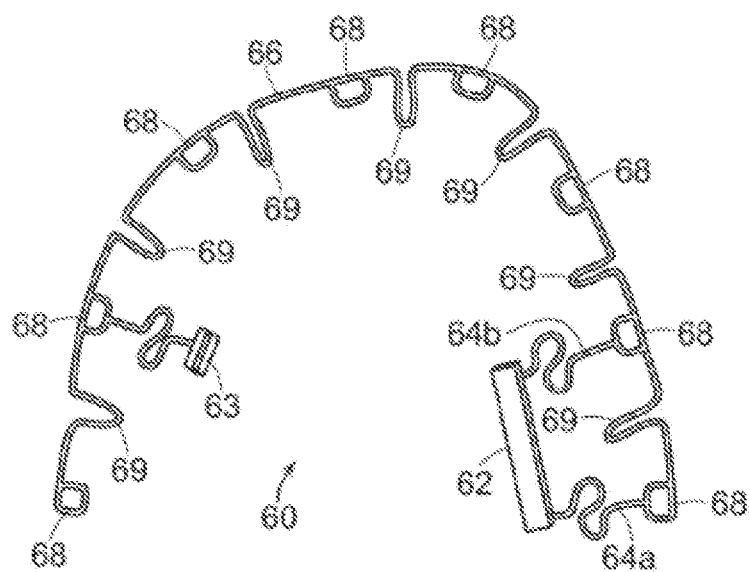
FIG. 6 is a diagram of another example appliance member.
Figure 7:
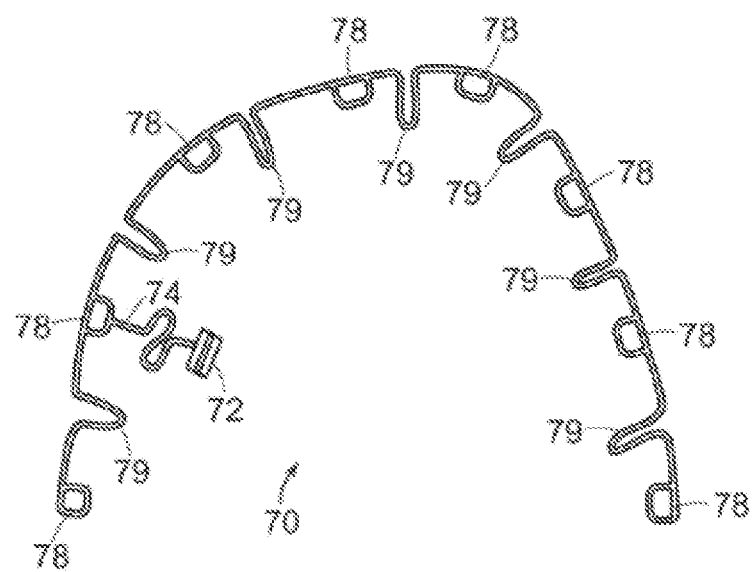
FIG. 7 is a diagram of another example appliance member.
Figure 8:
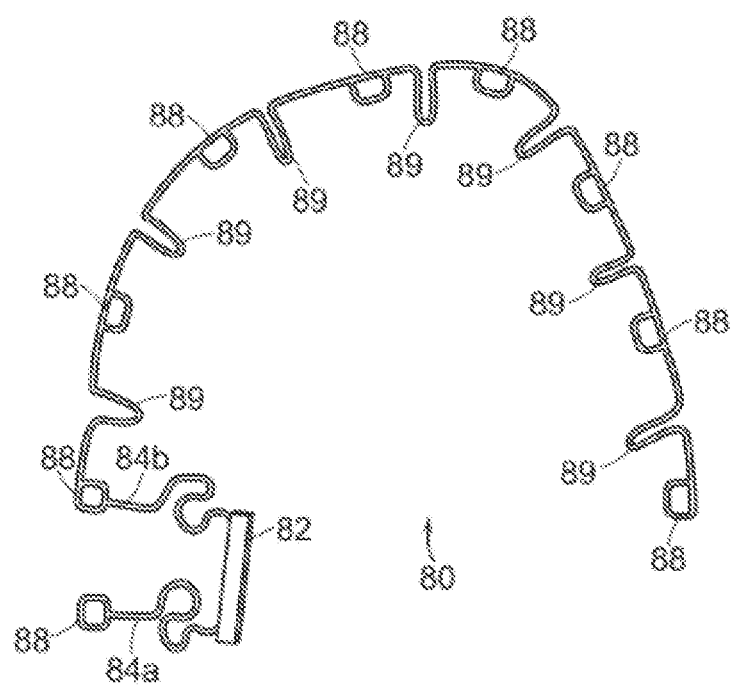
FIG. 8 is a diagram of another example appliance member.

Another example of an appliance having a combination of X and Z features is described with regard to the 2D member 50 for forming an appliance, as shown in FIG. 5. The 2D appliance member 50 in FIG. 5 is configured to be bent or otherwise formed into a 3D appliance in any suitable manner, including processes as described in U.S. patent application Ser. No. 15/370,704, filed Dec. 5, 2016. However, an appliance having features as described with regard to the example in FIG. 5 may be made according to other suitable processes.

An appliance in accordance with the example of FIG. 5 may be made and used in manners similar or corresponding to such manners described herein for the appliances 10 or 20 or the appliance member 40. An appliance according to the example of FIG. 5 may include certain features corresponding in structure or function (or both) to some of the features of the appliance 10 or the appliance 20, or the appliance member 40.

For example, the appliance member 50 includes a rigid bar 52 that corresponds to the rigid bar 12 of the appliance 10, or the rigid bar 22 of the appliance 20, or the rigid bar 42 of the appliance member 40. The rigid bar 52 has a lengthwise dimension that is configured to extend along the incisor, lateral incisor, and cuspid (canine) teeth, when the appliance is formed and installed. Further rigid bars or bar sections 53 and 54 are connected to (coupled to or extended from) the rigid bar 52, to extend along some or all of the bicuspid or molar teeth, when the appliance formed from the appliance member 50 and is installed. In other examples, the rigid bar 52 may be smaller in length than shown in FIG. 5 and, for example, may extend along some (but not all) of the incisor, lateral incisor, and cuspid (canine) teeth when the appliance is formed and installed. In other examples, the rigid bar 52 may extend further along bicuspid or molar teeth (in place of some or all of one or both bar or bar sections 53 and 54) when the appliance is formed and installed. In yet other examples, one or both sections 53 and 54 may be omitted or smaller than shown in FIG. 5.

The rigid bar 52 may have an arch shape (an arch shaped member having a generally arch-shaped configuration) that is configured to extend along two or more (or a plurality of) adjacent teeth in one of the patient's jaws, when the appliance is formed and installed. A plurality of arms 56 extend from the rigid bar 52. The arms 56 may correspond in structure and function as described with regard to the arms 14, 24 or 44 of the appliance 10 or 20 or the appliance member 40. For example, the arms 56 may include spring members and bracket connectors (or male connector elements) similar to those described with regard to arms 14, 24 or 44.

The arms 56 may be spaced along the length dimension of the rigid bar 52 in a manner similar to the spacing described with regard to arms 14 on the rigid bar 12 in FIG. 1, or the arms 44 on the rigid bar 42 in FIG. 4. In the appliance member 50, all of the arms 56 are located along the rigid bar 52 that is configured to extend along some or all of the incisor, lateral incisor, and cuspid (canine) teeth.

In the example in FIG. 5, the appliance member 50 includes six arms 56 extending from the rigid bar 52 to six corresponding bracket connectors 57. Each respective bracket connector 57 may be connected to or part of a single respective arm 56, such as shown in FIG. 5. In other examples, one or more (or all) of the bracket connectors may be connected to or part of two respective arms (for example, similar to the manner shown in FIG. 4 with regard to the bracket connectors 45a and 45b). In other examples, the appliance member 50 may include fewer or more arms along the length of rigid bar 52. Also, the appliance member 50 of other examples may include fewer or more bracket connectors.

An appliance member according to the example in FIG. 5 includes one or more further rigid bars or bar sections 53 and 54 connected to the rigid bar 52. Each further rigid bar 53 and 54 may have one or more (or a plurality of) loop or curved features and one or more (or a plurality of) bracket connectors (or male connector elements) along its length dimension. In the example in FIG. 5, the rigid bars 53 and 54 have a total of eight loop or curved features 58a-58h and eight bracket connectors (or male connector elements) 59a-59h. In other examples, each rigid bar 53 and 54 may have more or fewer loop or curved features or bracket connectors than shown in the example of FIG. 5.

Each of the bracket connectors 59 and loop or curved features 58 may correspond in structure, arrangement and function to any of the various examples described with regard to the bracket connectors 17 and loop or curved features 18 of the appliance 10, or with regard to the bracket connectors 45a-45n and loop or curved features 48 of the appliance member 40. In other examples, one or more (or all) of the bracket connectors 59, or features 58 may have other suitable structures, configurations or functions. One or more of the loop or curved features 58 can be configured to provide one or more of a desired flexibility, bias force strength, bias force direction, between two or more of the bracket connectors 59.

In certain examples, such as shown in FIG. 5, the loop or curved features 58 may include a loop or curved feature 58a at or adjacent the location at which the further rigid bar 53 extends from the rigid bar 52, and a further loop or curved feature 58e at or adjacent the location at which the further rigid bar 54 extends from the rigid bar 52. In such examples, the further rigid bars 53 and 54 may connect to the rigid bar 52, through the loop or curved feature 58a or 58e. Accordingly, one or both of the loop or curved feature 58a or 58e can be configured to provide one or more of a desired flexibility, bias force magnitude, bias force direction, durability or other characteristics at the interfaces of the rigid bar 52 and the further rigid bars 53 and 54.

Other examples appliances (or appliance members) 60, 70, 80 and 90 having a combination of X and Z features are shown in FIGS. 6-9A, respectively, and may be made and used in manners similar or corresponding to such manners described herein for the appliances 10 or 20, or the appliance members 40 or 50. An appliance according to any of the examples of FIGS. 6-9A may include certain features corresponding in structure or function (or both) to some of the features of the appliances 10 or 20, or the appliance members 40 or 50.

In particular, each of the appliances (or appliance members) 60, 70, 80 and 90 includes one or more rigid bars and one or more (or a plurality) of separate arms that extend from the one or more rigid bars, for example, in accordance with X embodiment features described herein. In particular, the appliance (or appliance member) 60 includes two rigid bars 62 and 63. The appliance 70 (or appliance member) includes a rigid bar 72. The appliance 80 includes a rigid bar 82, and the appliance 90 (or appliance member) includes a rigid bar 92. Each of the rigid bars 62, 82 and 92 have a lengthwise dimension that is configured to extend along two or more teeth, when the appliance is formed and installed. However, each of the rigid bars 63 and 72 has a lengthwise dimension that is configured to extend along one tooth, when the appliance is formed and installed. The rigid bars 62, 63, 72, 83 and 92 may each correspond in structure to the rigid bar 12 of the appliance 10, the rigid bar 22 of the appliance 20, the rigid bar 42 of the appliance member 40 or the rigid bar 52 of the appliance member 50. Other examples may include any suitable number, size and locations of rigid bars.

Each of the appliances (or appliance members) 60, 70, 80 and 90 includes one or more (or a plurality of) arms extending from the one or more rigid bars. For example, the appliance (or appliance member) 60 includes two arms 64a and 64b extending from the rigid bar 62, and a third arm 64c extending from the rigid bar 63. The appliance (or appliance member) 70 includes one arm 74 extending from the rigid bar 72. The appliance (or appliance member) 80 includes arms 84a and 84b extending from the rigid bar 82. The appliance 90 (or appliance member) includes one arm 94 extending from the rigid bar 92. Each of the arms extends to a respective bracket connector (or male connector element).

Each of the appliances (or appliance members) 60, 70, 80 and 90 includes one or more further rigid sections having Z embodiment features, and connected to (by being coupled to or integral with) the rigid bar 62, 63, 72, 83 or 92, through one or more arms. For example, the appliance (or appliance member) 60 includes a further rigid section 66 connected to the rigid bar 62 through arms 64a and 64b, and connected to the rigid bar 63 through the arm 64c. Similarly, the appliance (or appliance member) 70 includes a further rigid section 76 that is connected to the rigid bar 72 through the arm 74. Also similarly, the appliance (or appliance member) 80 includes a further rigid section 86 that is connected to the rigid bar 82 through an arm 84b. Also similarly, the appliance (or appliance member) 90 includes a further rigid section 96 that is connected to the rigid bar 92 through an arm 94.

Each of the further rigid sections 66, 76, 86 and 96 have a length dimension extending in a generally arch shaped configuration. One or more bracket connectors and one or more loop or curved feature (force applying feature) are provided along the length dimension of the one or more further rigid sections 66, 76, 86 and 96. For example, the rigid section 66 of the appliance (or appliance member) 60 has eight bracket connectors 68 and seven loop or curved features 69. Similarly, the rigid section 76 of the appliance (or appliance member) 70 has eight bracket connectors 78 and seven loop or curved features 79, the rigid section 86 of the appliance (or appliance member) 80 has eight bracket connectors 88 and seven loop or curved features 89, and the rigid section 96 of the appliance (or appliance member) 90 has eight bracket connectors 98 and seven loop or curved features 99. Any of the examples described herein may include one or more further bracket connectors that are connected to a rigid bar, but not to the further rigid section, such as the bracket connector at the distal end of the arm 84*a* in the appliance (or appliance member) 80 of FIG. 8.

In the examples shown in FIGS. 6-9A, each loop or curved feature (69, 79, 89, or 99) is located between a pair of adjacent bracket connectors (68, 78, 88 or 98) along the length dimension of the further rigid section (66, 76, 86 or 96, respectively). In other examples, the further rigid section may include no loop or curved feature (or two or more loop or curved features) between any of the adjacent pairs of bracket connectors. The number, configuration and location of loop or curved features on the further rigid bar 66, 76, 86 or 96 may be selected to provide the desired teeth connection positions and desired forces on the teeth, when the appliance is installed, as described herein.

Figure 9A:
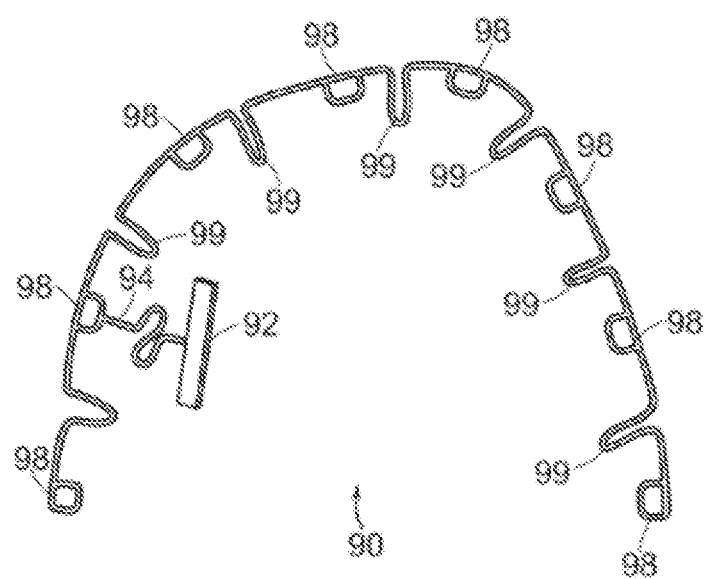
FIGS. 9A-9D are diagrams of other example appliance members.
Figure 9B:
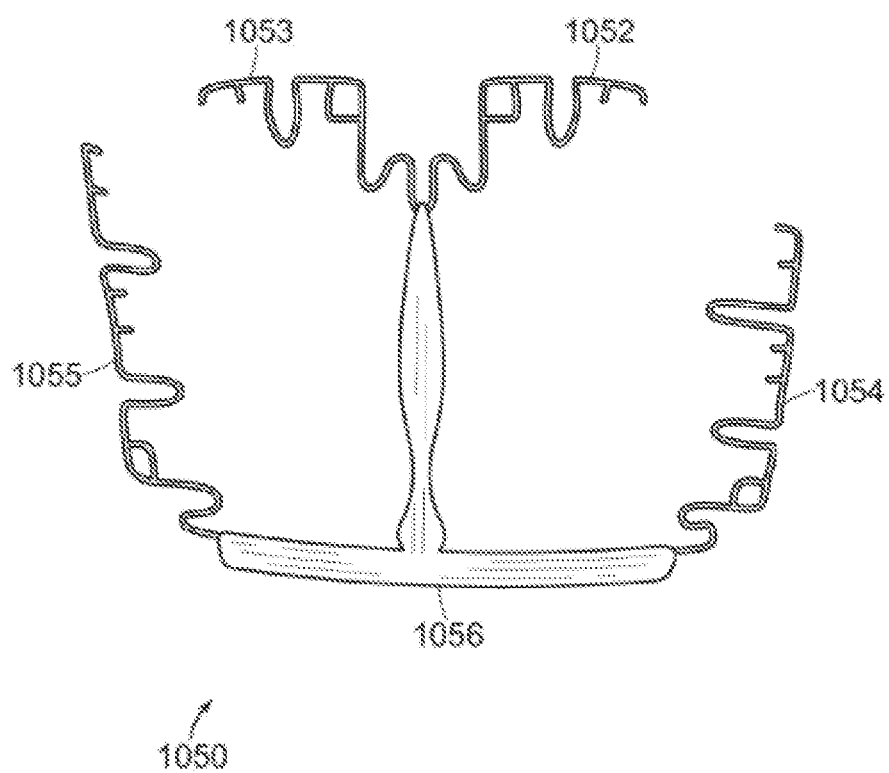
Figure 9C:
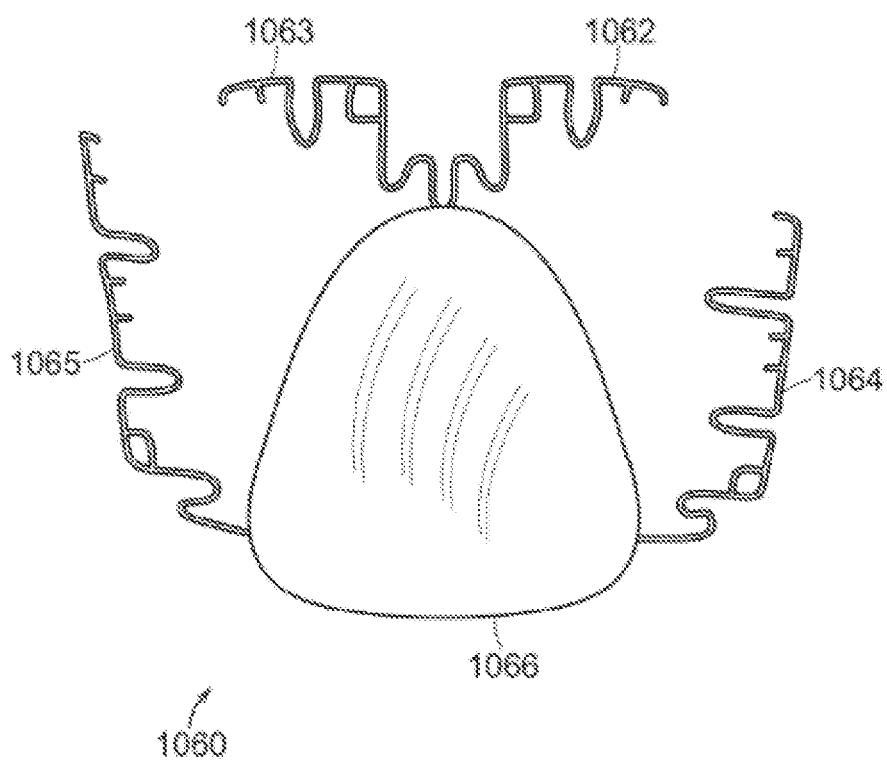
Figure 9D:
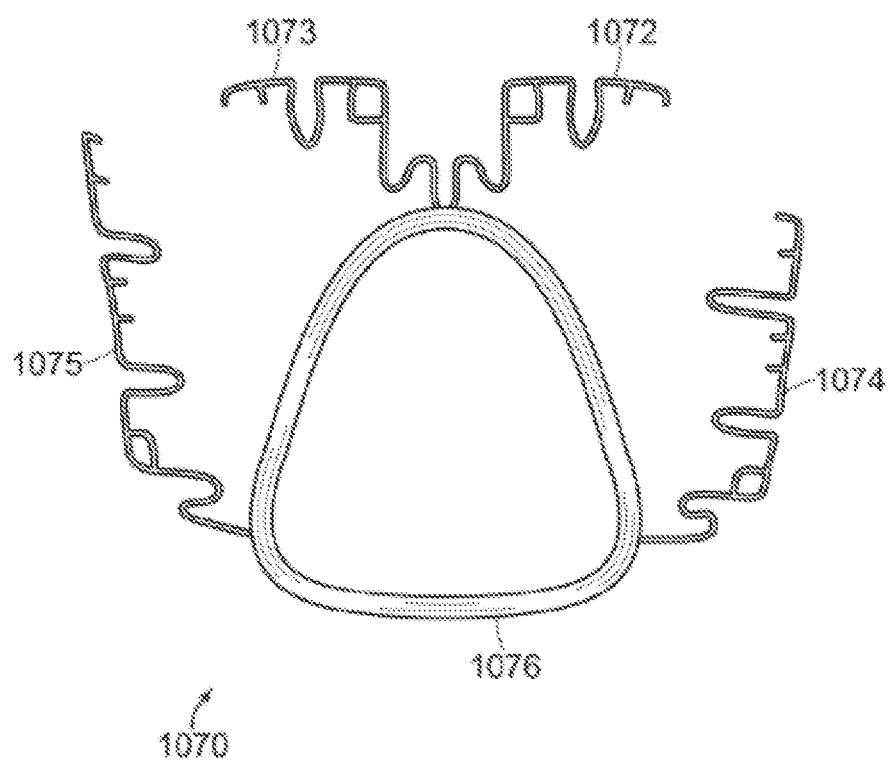

Additional examples of appliances (or appliance members) are shown in FIGS. 9B-9D, each including a plurality of further rigid sections, each having Z embodiment features. In the example appliance (or appliance member) 1050 in FIG. 9B has four further rigid sections 1052, 1053, 0154 and 1055 extending from a T-shaped central rigid bar 1056. The central rigid bar 1056 has a generally T shape. The example appliance (or appliance member) 1060 of FIG. 9C, has four further rigid sections 1062, 1063, 1064 and 1065 extending from a central rigid palate plate 1066. The central rigid palate plate 1066 has a shape to fit against a patient's palate. The example appliance (or appliance member) 1070 in FIG. 9D has four further rigid sections 1072, 1073, 0174 and 1075 extending from a central annular-shaped rigid bar 1076. In any of the appliances described herein, one or more of the arms or loop or curved features or bracket connector elements may be omitted, and replaced with a portion of the rigid bar or further rigid section that is formed to be rigid with minimal or no flexibility, for example for improved anchorage.

In each of the examples in FIGS. 1-9, the appliance (or an appliance member) includes one or more X embodiment features (in combination with one or more Z embodiment features), including one or more (or a plurality of) arms, extending to one or more (or a plurality of) bracket connectors (or male connector elements). One or more (or each) of the arms may include one or more spring member features. Any of the arms, spring members, and bracket connectors (or male connector elements) of FIGS. 1-9 may have any suitable configuration, including the configurations shown in the respective drawings of those FIGS. 1-9. In other examples, any one or more of the arms, spring members, or bracket connectors (or male connector elements) in any of those or other appliances (or appliance members) described herein may have other suitable configurations according to any of the other arms, spring members, or bracket connectors (or male connector elements) described herein.

Further examples of arms 100-132 that may be employed as one or more of the arms in any of the examples described herein or in U.S. patent application Ser. No. 15/370,704, filed Dec. 5, 2016, or yet other appliance examples, are described with reference to FIGS. 10, 11 and 12. Each of the example arms 100-132 extends from a rigid bar 133 to an associated bracket connector (or male connector element) 100*a*-132*a*. The rigid bar 133 may correspond to the rigid bar 12, 22, 42, 52, 62, 63, 72, 82 or 92 in any of the examples of FIGS. 1-9, or the rigid bar of any other examples described herein, or of yet other appliance or appliance member examples.

Each of the arms 100-132 includes a spring member 100*b*-132*b*. In other examples, an arm may include more than one spring member. In particular examples, each spring member has a configuration (including a shape, material, and size) that provides one or more of a desired flexibility, bias force magnitude, bias force direction, durability or other characteristics The number, configuration and location of the spring members may be selected to provide (when the appliance is installed) the desired forces on the teeth to which the bracket connectors of the appliance connect, when the appliance is installed as described herein. For example, the number, configuration and location of the spring members may be selected to move one or more teeth from an original tooth arrangement (OTA) to the final tooth arrangement (FTA), or to an intermediate tooth arrangement (ITA), or from an ITA to an FTA or another ITA.

Figure 10:
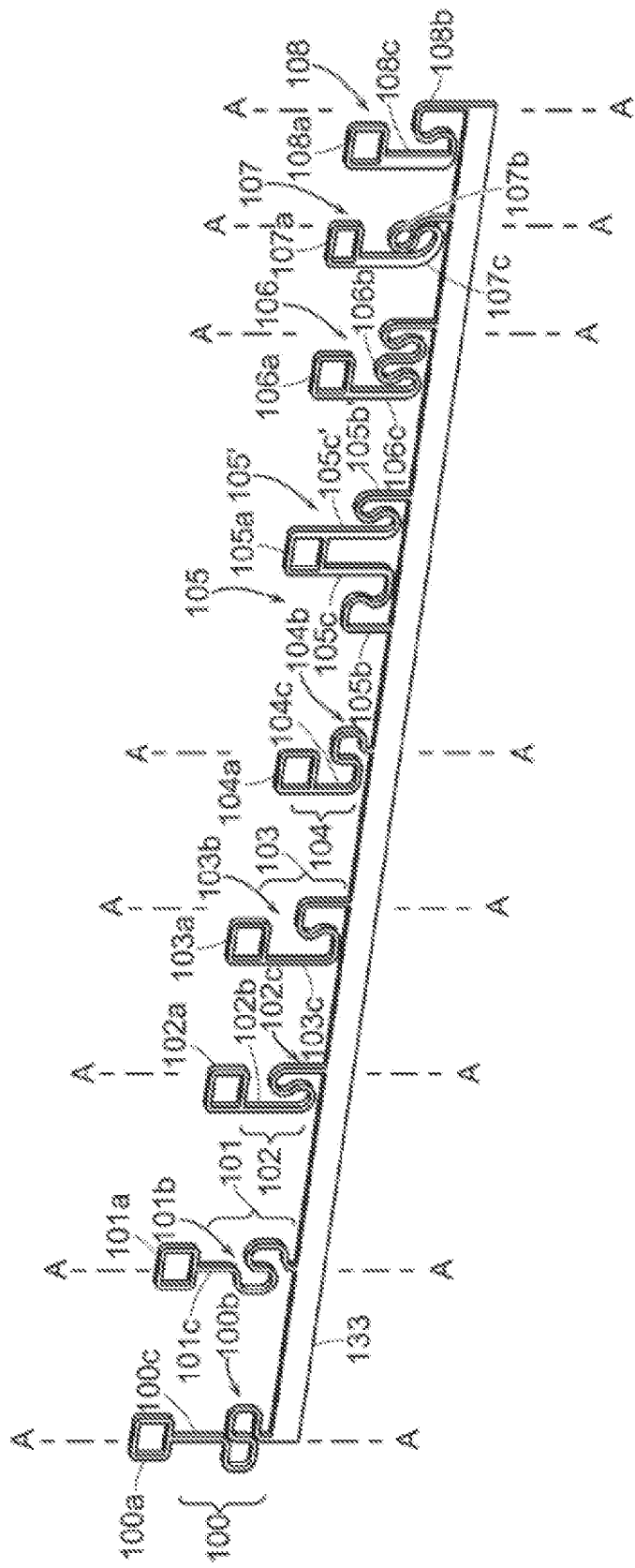
FIG. 10 is a diagram of various examples of arms of an appliance member.

The arm 100 includes a spring member 100*b* that has a shape having two open loop portions arranged adjacent each other in a horizontal direction (direction generally parallel to the length dimension of the rigid bar 133), forming an "S" shape laying in that horizontal direction. In other examples, the spring member may have one open loop or more than two open loops. In the example of FIG. 10, the bracket connector 100*a* of the arm 100 is located vertically above the location at which the arm couples to or extends from the rigid bar 133 (and is centered along an axis A perpendicular to the length dimension of the rigid bar 133 at the location at which the arm 100 connects to the rigid bar 133). In other examples, the bracket connector 100*a* may be located laterally offset from the axis A (e.g., toward the right or the left of the axis A).

The arm 100 in the example in FIG. 10 includes a linear arm section 100*c* that extends from the spring member 100*b* to the bracket connector 100*a*. In some examples, the linear arm section 100*c* may extend along the axis A as shown in FIG. 10. In other examples, the linear arm section 100*c* may be laterally spaced from but parallel to the axis A, or may extend at an angle transverse (non-parallel) to the axis A. In other examples, the arm section 100*c* may be non-linear (curved or other suitable shape) or may be omitted (such that the spring member 100*b* extends to the bracket connector 100*a*). In certain examples, the arm section 100*c* (or corresponding arm section of other arms described herein) has a sufficient length dimension to be gripped by a clinician, doctor or other trained personnel (e.g., with a tool, such as, but not limited to a Weingart tool as described herein) during installation of an appliance, to help guide the bracket connector 100*a* into engagement with a bracket.

The two open loop portions of the spring member 100*b* of the arm 100 have a generally rectangular shape, including one or more straight edges (e.g., the horizontal and vertical edges of the spring member 100*b* in FIG. 10) that meet at rounded corners. In other examples, the open loop portions of the spring member may have curved edges or may be elongated in the vertical (axis A) direction or in the horizontal direction (perpendicular to axis A), or in a direction that is at an obtuse angle relative to the axis A.

For example, the arm 101 in FIG. 10 has a spring member 101*b* and arm section 101*c* that is similar in shape and configuration to the spring member 100*b* and arm section 100*c* of the arm 100. However, the two open loop portions of the spring member 101*b* of the arm 101 have rounded edges. In addition, the two open loop portions of the spring member 101*b* are more elongated in the vertical direction (direction of axis A) than in a horizontal direction (perpendicular to the direction of axis A). In other examples, the open loop portions of the spring member 101*b* may be more elongated in the horizontal direction than in in the vertical direction, or in a direction at an obtuse angle relative to the axis A. Similarly, other examples of the spring member 100*b* of the arm 100 may have loop portions that are more elongated in the vertical direction, the horizontal direction, or an obtuse angled direction, relative to the axis A.

FIG. 10 shows another example of an arm 102 that includes a spring member 102b with a shape having two open loop portions arranged adjacent each other in a horizontal direction (direction generally parallel to the length dimension of the rigid bar 133), forming an "S" shape laying in that horizontal direction. However, the center of the bracket connector 102a of the arm 102 is laterally offset from the axis A, such that the bracket connector 102a is located mostly or entirely on one side of the axis A (the left side in FIG. 10). In other examples, the spring member 102b may be oriented in the opposite direction as shown, such that the bracket connector 102a is located mostly or entirely on the other side of the axis A (the right side in FIG. 10).

In the arm 102, the spring member 102b is configured such that the entire spring member 102b (or substantially the entire spring member 102b) is located vertically below the bracket connector 102a (between the bracket connector 102a and the rigid bar 133). In other examples, some or all of the spring member 102b may be located laterally offset from the bracket connector 102a (in a direction perpendicular to the axis A).

For example, the arm 103 in FIG. 10 has a spring member 103b and arm section 103c that is similar in shape and configuration to the spring member 102b and arm section 102c of the arm 102. However, the two open loop portions of the spring member 103b are spread out in the lateral direction more than the open loop portions of the spring member 102b. As a result, a substantial portion of the spring member 103b (e.g., one of the loop portions) is laterally offset from the bracket connector 103a in a direction perpendicular to the axis A.

The arm 104 has a has a spring member 104b and arm section 104c that is similar in shape and configuration to the spring member 103b and arm section 103c of the arm 103. However, the two loop portions of the spring member 104b are shaped different from the loop portions 103b. In particular, one of the open loop features of the spring member 104b has a "U" shape, with one of the sides or arms of the "U" shape loop extending to the bracket connector 104a and the other side or arm of the "U" shape loop extending from the other loop of the spring member 104b. In addition, the length of the arm section 104c is smaller than the length of the arm section 103c. In certain examples, the length of the arm section 100c-130c may be selected, to provide a desired distance between the bracket connector 100a-130a and the rigid bar 133. The arm section length may be selected to accommodate or fit a desired or particular patient tooth arrangement.

FIG. 10 shows other examples arms 105, 105', 106, 107 and 108 that include a spring member with a shape having two or more open loop portions arranged adjacent each other in a horizontal direction (direction generally parallel to the length dimension of the rigid bar 133), forming an "S" shape laying in that horizontal direction.

The arms 105 and 105' in FIG. 10 are each connected to the same (a common) bracket connector, such that the bracket connector 105a is connected to the rigid bar 133 through the two arms 105 and 105'. The arm 105 has a spring member 105b that is similar in shape to the spring member 103b, but oriented in the opposite direction. The arm 105' has a spring member 105b' that is similar in shape to the spring member 102b. In other examples, the arms 105 and 105' may have a spring member having any suitable configuration, shape and size such as, but not limited to the other examples of spring members described herein or in U.S. patent application Ser. No. 15/370,704, filed Dec. 5, 2016.

The arm 106 in FIG. 10 includes a spring member 106b having more than two (i.e., four) open loop portions. Other examples of that spring member or other spring members described herein may include any suitable number of loop portions. The spring member 107b of the arm 107 of FIG. 10 has loop portions that are elongated in a direction that is at an obtuse angle relative to the axis A. The arm 108 in FIG. 10 has a spring member 108b that is similar in shape to the spring member 103b. However, the arm 108 has an arm section 108c that is wider (in the horizontal dimension) than other sections of the arm 108. Other examples of any of the arm members described herein or in U.S. patent application Ser. No. 15/370,704, filed Dec. 5, 2016 may include an arm section (similar to arm section 108c) that is wider than other sections of the arm.

Figure 11:
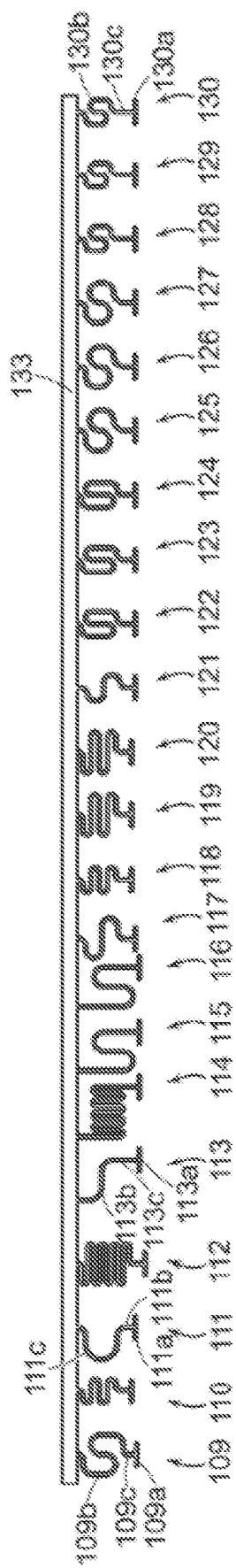
FIG. 11 is a diagram of various further examples of arms of an appliance member.

FIG. 11 shows further examples of arms 109, 114, 115 and 122-130 that include a spring member with a shape having at least two open loop portions arranged adjacent each other in a horizontal direction (direction generally parallel to the length dimension of the rigid bar 133), forming an "S" shape laying in that horizontal direction. FIG. 11 also shows examples of arms 110, 112, and 117-121 that include a spring member with a shape having at least two open loop portions arranged adjacent each other in a vertical direction (direction generally perpendicular to the length dimension of the rigid bar 133), forming one or more "S" shapes in that perpendicular direction. FIG. 11 shows a further example of an arm 111 having a "U" shaped spring member 111b. A further example of an arm 113 in FIG. 11 has a spring member 113b formed of two right angle bends along the length dimension of the arm.

In any of the examples described herein, the width dimensions of the arm or of one or more selected portions of the arm) may be selected to provide one or more of a desired flexibility, bias force magnitude, bias force direction, durability or other characteristics. For example, the arms 115 and 116 have a similar shape, but the width dimension of the arm 115 is greater than the width of the arm 116. As another example, the arms 122, 123 and 124 in FIG. 11 have a similar shape, but the width dimension of the arm 124 is greater than the width of the arm 123. Similarly, the width dimension of the arm 123 is greater than the width of the arm 122. In further examples, as an alternative or in addition to varying width dimensions, one or more of the arms (or selected portions of the arms) may have a varying thickness dimension (in the dimension into and out of the plane of the page of FIG. 11), for a desired flexibility, bias force magnitude or direction, durability or other characteristic. In certain examples, the arms may be made smaller in width or thickness dimension (or both) relative to the rigid bar 133 from which they extend, such that the rigid bar 133 may provide a more rigid anchorage, while the arms provide a desired flexibility and resilience. Width or thickness dimension variances may be provided by any suitable process, including but not limited to machining, molding, laser cutting, 3D printing, or sinker EDM (Electronic Discharge Machining) to vary thickness of portions of an appliance member cut from a sheet. Alternatively or in addition to selecting or varying width or thickness dimensions, the arm length may be selected to provide or contribute to a desired flexibility, bias force, magnitude or direction, durability or other characteristic.

As another example, the arms 125, 126 and 127 in FIG. 11 have a similar shape relative to each other, but the width dimension of the arm 127 is greater than the width of the arm 126, which is greater than the width of the arm 125. As yet another example, the arms 128, 129 and 130 in FIG. 11 have a similar shape relative to each other, but the width dimension of the arm 130 is greater than the width of the arm 129, which is greater than the width of the arm 128. Each of the example arms 109-130 shown in FIG. 11 has a uniform width dimension that is constant over the entire arm. In other examples, the width dimension of one or more portions of any of the arms 100-132 may be made greater or smaller than the width dimension of one or more other portions of the same arm.

Figure 12:
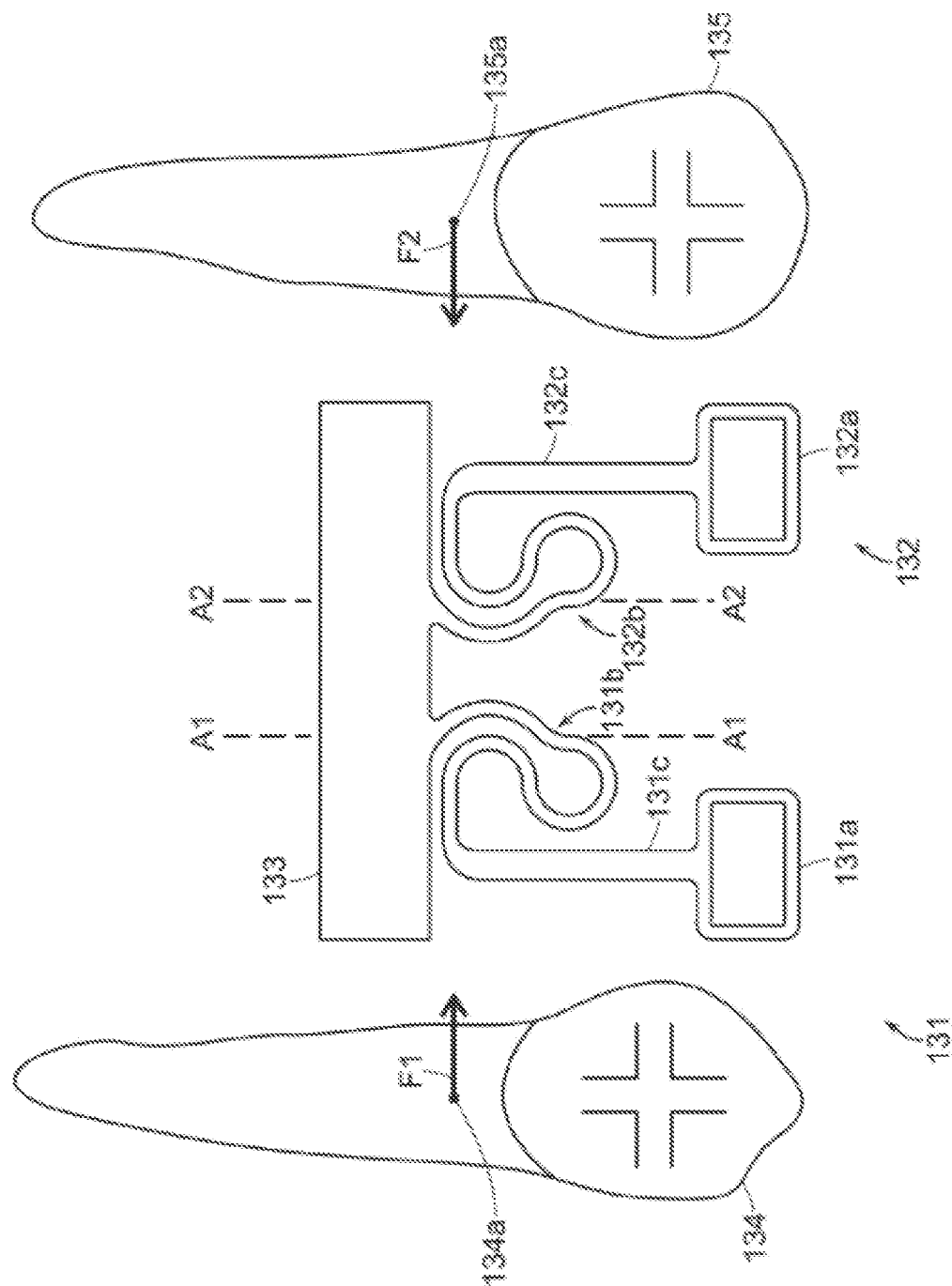
FIG. 12 is a diagram of other examples of arms of an appliance member.

FIG. 12 shows further examples of two adjacent arms 131 and 132 extending from a rigid bar 133 of an appliance, appliance member (or a portion of an appliance or appliance member). Each arm 131 and 132 extends to an associated bracket connector (or male connector element) 131a or 131b. Each of the arms 131 and 132 include a spring member 131b or 132b, and an arm section 131c or 132c extending from the spring member to the bracket connectors 131a or 132a.

The bracket connector 131a is configured to be connected to a bracket secured to a first tooth 134 in a patient's jaw, and the bracket connector 132a is configured to be connected to a bracket secured to a second tooth 135 in the patient's jaw. The first tooth 134 and the second tooth 135 may be adjacent teeth in the patient's jaw. In other examples, one or more other teeth (or extracted teeth locations) may be located between the first tooth 134 and the second tooth 135. In one example, the tooth 134 may be a canine tooth, while the tooth 135 may be a second pre-molar. In other examples, the teeth 134 and 135 may be other teeth in a patient's jaw (upper jaw or lower jaw).

In certain examples, the arm configuration may be selected to provide one or more of a desired flexibility, bias force magnitude, bias force direction, durability or other characteristics. For example, arms configured according to examples 100 and 101 may provide sufficient force (magnitude and direction) for providing some, but a limited amount of movement in occlusogingival direction or a buccolingual direction, when the appliance is installed. Arms configured according to examples 102, 103 and 104 may provide sufficient force (magnitude and direction) to move extrude or to move in occlusogingival direction. Arms configured to be relatively rigid may be employed when the tooth to be connected to the arm is not to be moved (or moved by a limited amount) and may be used for anchorage. In certain examples, arms configured according to examples 106, 107 and 108 may be used in extraction cases to apply a force closer to the center of resistance of the teeth and to prevent the teeth from tipping, as the arm section 106c, 107c and 108c in those examples is formed wider than other portions of the arm, such that the arm can act as a power arm.

In certain examples, any of the arms 100-132 in FIG. 10, 11 or 12 (or other arms described herein) may be configured to provide a bias force direction and magnitude at a desired location along the length of the arm and, thus, at a desired location relative to the tooth structure of a patient. For example, the arms shown in FIG. 12 may be configured to provide a force on one or both teeth 134 and 135 (when the bracket connectors 131a and 132a are connected to respective brackets on the teeth 134 and 135), where the force on each tooth is directed toward the adjacent tooth. In particular examples, the arms 131 and 132 are configured to apply the force on one or both teeth 134 and 135, at a location along the length dimension of each tooth corresponding to a center of resistance location. In the drawing if FIG. 12, the teeth 134 and 135 are shown laterally adjacent to the respective arms 131 and 132. However, it will be understood that, when the bracket connectors 131a and 132a are connected to brackets on the respective teeth 134 and 135, each of the bracket connectors 131a and 132a will be placed on or directly adjacent to a surface of a respective tooth 134 and 135 on which a bracket (not shown in FIG. 12) is secured, as described herein.

In the example in FIG. 12, the arm 131 is configured such that the arm section 131c extends generally parallel to, but laterally offset from an axis A1 (the axis direction perpendicular to the length dimension of the rigid bar 133 at the location at which the arm 131 connects to the rigid bar 133). Similarly, the arm 132 is configured such that the arm section 132c extends generally parallel to, but laterally offset from an axis A2 (the axis direction perpendicular to the length dimension of the rigid bar 133 at the location at which the arm 131 connects to the rigid bar 133).

More specifically, the arm section 131c is laterally offset from the axis A1, in a direction to the left of A1, such that spring member 131b of the arm 131 and the axis A1 are located between the arm section 131c and the arm 132. Similarly, the arm section 132c is laterally offset from the axis A2, in a direction to the left of A2, such that spring member 132b of the arm 132 and the axis A2 are located between the arm section 132c and the arm 131. In addition, the spring members 131b and 132b of the arms 131 and 132 are configured such that (when the arms 131 and 132 are connected to respective teeth 134 and 135) the arm 131 imparts a force F1 on the tooth 134 in a direction toward the arm 132, and the arm 132 imparts a force F2 on the tooth 135 in a direction toward the arm 133. The magnitude of the force F1 and F2 depend on one or more (or a combination of) the shape and configuration of the arms 131 and 132 (including the spring members 131b and 132b), the lateral spacing between the arms 131 and 133, and the thickness and material of the arms 131 and 132.

In the example in FIG. 12, the spring members 131b and 132b of the arms 131 and 132 are located adjacent (or relatively close to) the rigid bar 133. In addition, the length of the arm sections 131c and 132c may be configured to locate the rigid bar 133 at or near the centers of resistance 134a and 135a of the respective teeth 134 and 135. In that manner, the spring members 131b and 132b may be located at or near the centers of resistance 134a and 135a of the respective teeth 134 and 135 (to impart the force F1 or F2 on the tooth 134 or 135, at or near the center of resistance 134a or 135a of the tooth 134 or 135). In other examples, the arms 131 and 132 may be configured to impart a force F1 or F2 on a tooth 134 or 135, at a location that is spaced apart (e.g., vertically offset in the orientation of FIG. 12) from the center of resistance 134a or 135a of the tooth 134 or 135, by a specified distance. In such other examples, the force F1 or F2 can have a lever-like action on a tooth 134 or 135, where the center of resistance acts as a fulcrum. The center of resistance of a tooth may depend on various factors, including the depth and angle of the root of the tooth, type of tooth or other factors. In particular examples described herein, an appliance (or method) may include one or more arms that are configured to impart one or more forces on one or more teeth, where the direction, and magnitude of the force or forces may be selected, and the location of the force (relative to a center of resistance of the tooth) may be selected based, in part, on the configuration of the arm (including, for example, the configuration of the spring member 131b, 132b, the distance and location of the spring member relative to the rigid bar 133, and the length of the arm section 131c, 132c).

Each of the example arms 100-108 in FIG. 10 and arms 131 and 132 in FIG. 12 is shown as extending to (being formed integral with or coupled to) to a bracket connector 100a-108a that has an annular or ring shape and in particular, a square, annular shape (having a generally square-shaped outer perimeter and a generally square-shaped opening). In other examples, an annular or ring-shaped bracket connector may have a generally round or rounded shape, an oval shape (having a round or oval outer perimeter and a round or oval opening) or other suitable shape.

Each of the example arms 109-130 in FIG. 11 extends to a bracket connector 100a-108a that has a T shaped configuration. In certain examples, such T shaped bracket connectors may correspond to the T shaped male connector elements as described in U.S. patent application Ser. No. 15/370,704, filed Dec. 5, 2016 (such as those identified by reference numbers 1802, 1822, or 2500 in that publication).

In other examples, any of the arms described with regard FIGS. 10 and 12, may extend to (be formed integral with or coupled to) a T shaped bracket connector of FIG. 11, or any of the other bracket connectors (or male connector elements) described herein or in U.S. patent application Ser. No. 15/370,704, filed Dec. 5, 2016, in place of the bracket connectors 100a-108a. Similarly, in other examples, any of the arms described with regard FIG. 11, may extend to an annular or ring shaped bracket connector described in regard to the examples of FIG. 10, or any of the other bracket connectors (or male connector elements) described herein or in U.S. patent application Ser. No. 15/370,704, filed Dec. 5, 2016, in place of the bracket connectors 109a-130a.

One further example of a connector element (or male connector element) and brackets (or female connector element) is described with reference to FIGS. 13-34 herein.

Figure 13:
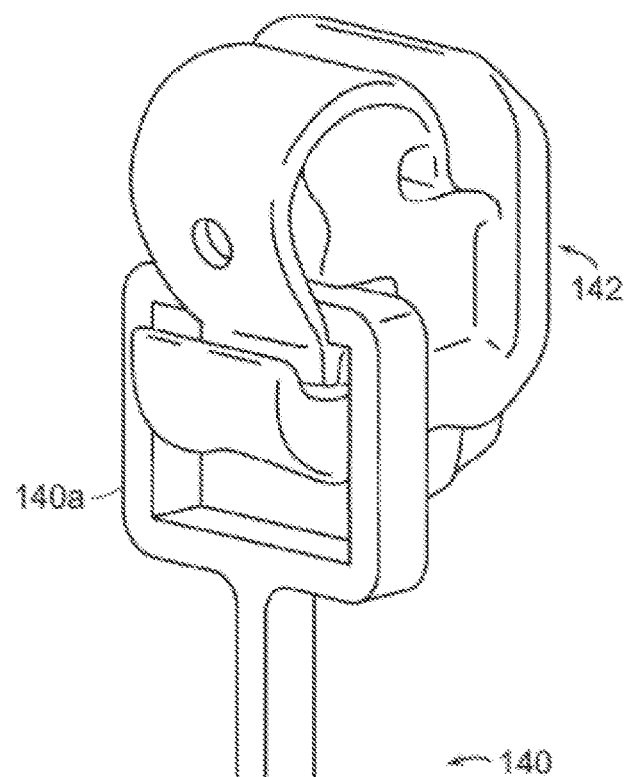
FIG. 13 is a perspective view of a bracket connector of an appliance connected to a bracket.
Figure 14:
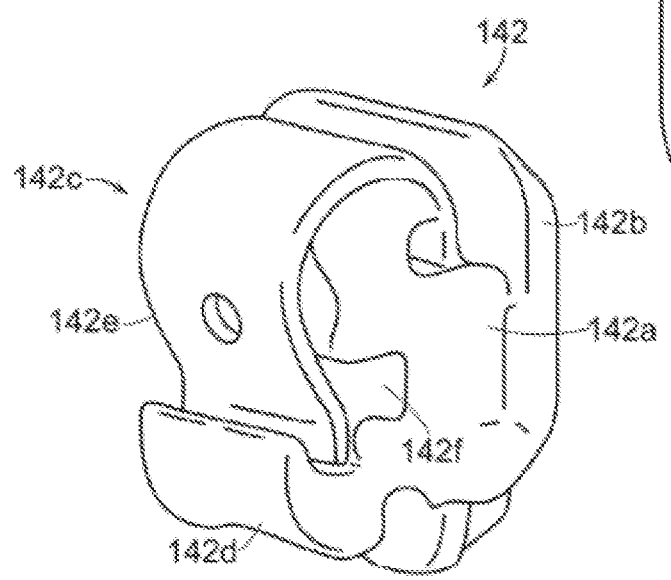
FIG. 14 is a perspective view of the bracket in FIG. 13.

In particular, FIGS. 13 and 14 show an example of a bracket connector 140a on an arm 140, and an associated bracket 142. In FIG. 13, the bracket connector 140a is shown in a connected state (connected to a bracket 142).

The bracket connector 140a has an annular or ring shape and in particular, a square, annular shape (having a generally square-shaped outer perimeter and a generally square-shaped opening). The bracket connector 140a of FIG. 13 may correspond, for example, to the bracket connectors 100a-108a in FIG. 10. The arm 140 may have a spring member, and may have a configuration corresponding to any of the arms and spring member described herein or in U.S. patent application Ser. No. 15/370,704, filed Dec. 5, 2016, including but not limited to the arms 100-130 and spring members 100b-132b in FIGS. 10, 11 and 12, or other suitable configuration.

The bracket 142 has a body portion 142a defining a back surface 142b (facing inward toward the plane of the page in FIG. 14) for securing to an outer surface of a patient's tooth. The surface 142b may be secured to a patient's tooth via direct or indirect bonding, or other suitable mechanism for fixedly securing the elements to a surface of the teeth. Bonding materials may include adhesives such as, but not limited to composite resin. In the case of indirect bonding, a clinician may use a jig to increase the accuracy of the bracket placement. In particular examples, the bracket 142 may be configured to have the lowest profile possible (to minimize the size in the dimension extending away from the tooth.

Intraoral scanning or an impression of the arches may be taken after attaching bracket elements on one or more (or all) of the patient's teeth. The impressions or scans (or both) include and, thus, provide information to help identify the position of the brackets on the teeth. That information is used by clinicians, manufacturers or technicians in the design of the appliance, for example, to help identify appropriate positions on the appliance to place or form one or more bracket connectors (or male connector elements), for proper alignment with one or more brackets on the teeth.

The bracket 142 includes a clip portion 142c that extends outward from the body portion 142a and has a clip that is configured to receive and hold the bracket connector 140a. The clip portion 142c includes a lip 142d and a flexible spring element 142e that (with the body portion 142a) form a receptacle 142f. The receptacle 142f is configured to selectively receive a portion (the upper edge) of the annular or ring shaped bracket connector 140a, as shown in FIG. 13.

Before and after receiving the bracket connector 140a by the clip portion 142c, the spring element 142e has one end that engages (but is not attached to) the lip 142d at an interface, to enclose or partially enclose a volume defining the receptacle 142f. The spring element 142e (or the lip 142d, or both) is sufficiently flexible to flex and allow the bracket connector 140a to be passed between the spring element 142e and the lip 142d from a location outside of the receptacle 142f, to a location inside of the receptacle 142f. For example, the spring element 142e or the lip 142d (or both) may flex away from each other, when engaged and pressed with sufficient force (for example, by pressing a bracket connector 140a into the interface of spring element 142e and the lip 142d). The spring element 142e or the lip 142d (or both) may be made of sufficiently resilient material so as to return to or toward a pre-flexed state, after the bracket connector 140a is received within the receptacle 142f, to retain (and hold) the bracket connector 140a within the receptacle 142f. In particular examples, the clip portion 142c may be configured to selectively release a bracket connector 140a from the receptacle 142f, for example, by a clinician, doctor or other trained personnel using a tool to flex the spring element 142e or the lip 142d (or both), while withdrawing the bracket connector 140a from the receptacle 142f.

In particular examples, the receptacle 142f (and portions of the lip 142d that define the receptacle 142f) has a generally linear or straight surface on which a linear or straight edge of the bracket holder 140a engages, when the bracket holder 140a is connected to the bracket 142, as shown in FIG. 13. In other examples, the lip 142d may have a curved surface for engaging a curved edge of a bracket holder (for example, where the bracket holder has an annular or ring shape that is circular or oval.

The bracket 142 may be made of any suitable material or materials, such as, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in single structure.

FIGS. 15-28 show further examples of bracket connectors (or male connector elements) and associated brackets (or female connector elements), where the bracket connectors have a squeezable configuration that, during installation, is squeezed to compress in at least one dimension, and then resiliently expanded to connect with a bracket upon release of the squeezing force.

Each of the bracket connectors shown in FIGS. 15, 17, 19, 21, 23 and 28 is on one end of an arm. The arm may have a spring member having a configuration as shown in the drawings. In other examples, the arm and the spring member associated with any of those bracket connector examples of FIGS. 15, 17, 19, 21, 23 and 28, may be configured to correspond to any of the other arms and spring members described herein or in U.S. patent application Ser. No. 15/370,704, filed Dec. 5, 2016, including but not limited to the arms 100-132 and spring members 100b-132b in FIGS. 10, 11 and 12, or other suitable configuration. In particular examples, each of the bracket connectors shown in FIGS. 15, 17, 19, 21, 23 and 28 is on one end of arm that extends from a rigid bar of an appliance, in accordance with a X embodiment feature. In other examples, a bracket connector as described with regard to any of those drawings may be included as one or more of the bracket connectors on a rigid bar of an Z embodiment feature.

Figure 17:
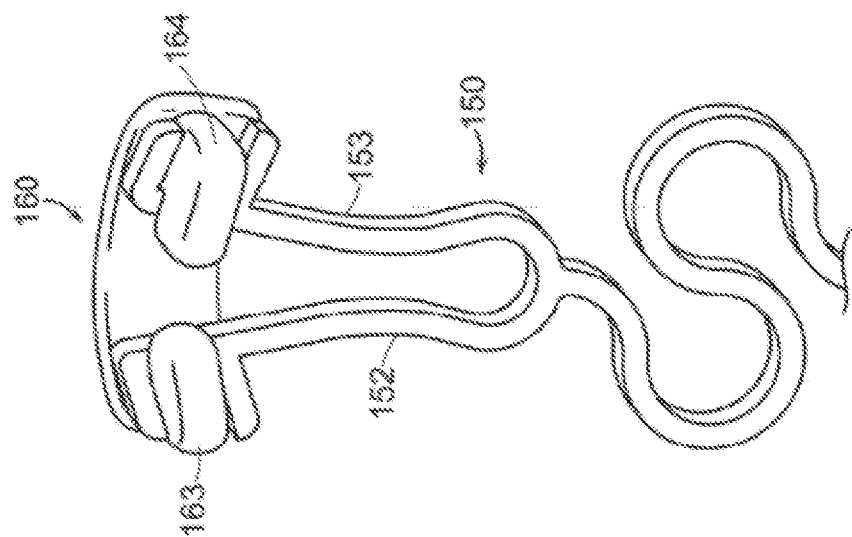
FIG. 17 is a perspective view of the bracket connector of FIG. 15 connected to the bracket of FIG. 16.
Figure 16:
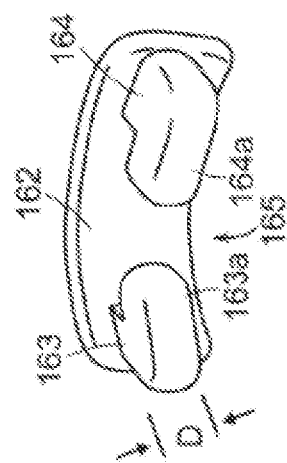
FIG. 16 is a perspective view of a bracket.
Figure 15:
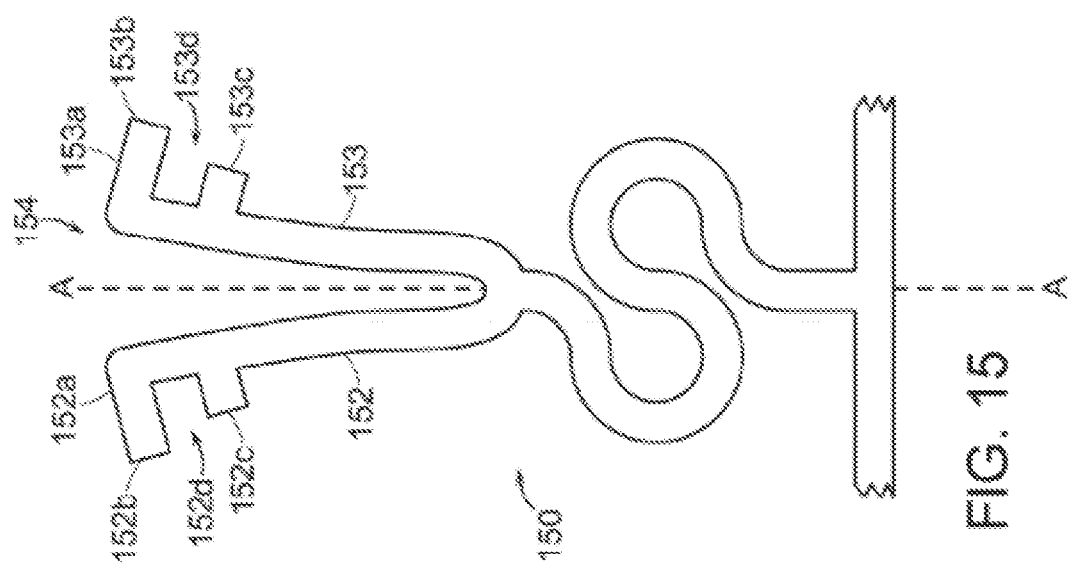
FIG. 15 is a diagram of a bracket connector.

A bracket connector 150 and associated bracket 160 is shown in FIGS. 15-17. In FIG. 15, the bracket connector 150 is shown in a disconnected state (not connected to a bracket 160). In FIG. 16, the bracket 160 is shown in a disconnected state (not connected to a bracket connector 150). In FIG. 17, the bracket connector 150 and the bracket 160 are shown in a connected state (with the bracket connector 150 connected to a bracket 160).

The bracket connector 150 in FIG. 15 includes a shaped body portion having first and second arm sections 152 and 153. The arm sections 152 and 153 connect to each other at a U-shaped interface (having a central axis A). Each arm section 152 and 153 has a free end 152a and 153a, respectively, and one or more (or a plurality of) projections extending from the arm section at or near the free end.

In the example of FIG. 15, the arm section 152 has two projections 152b and 152c facing outward relative to the U-shape (or axis A). Similarly, the arm section 153 has two projections 153b and 153c facing outward relative to the U-shape (or axis A). The two projections 152b and 152c are spaced apart from each other by a specified distance to define a gap 152d between the projections. Similarly, the two projections 153b and 153c are spaced apart from each other by a specified distance to define a gap 153d between the projections. In other examples, each arm section 152 and 153 may have more than two projections. In certain examples, the number of projections on the arm section 152 is equal to the number of projections on the arm 153. In other examples, the number of projections on the arm section 152 is greater or less than the number of arms on the arm section 153. In yet other examples, one of the arm sections may have no projections.

In the example in FIG. 15, the arm sections 152 and 153 are spaced apart from each other (except at the U shaped connected end), to form a gap 154 between the arm sections and extending along a portion of the length of each arm section. The bracket connector 150 is made of a sufficiently flexible and resilient material that allows the free ends 152a and 153a of the arm sections 152 and 153 to be forced to move toward each other when a sufficient squeezing force is applied to the arm sections (in a direction toward the axis A), and then resiliently move back to their original state when the force is removed. When the arm sections 152 and 153 are forced toward each other, the width dimension of the gap 154 between the arm sections 152 and 153 decreases, resulting in a decrease in the width dimension of the bracket connector 150 (at least along a portion of the length of each arm section 152 and 153). In that state (a squeezed or compressed state), the bracket connector 150 is received by the bracket 160. When the bracket connector 150 is received by the bracket 160, the force on the arm sections 152 and 153 is released to allow the arm sections to resiliently move outward, toward a second state (such as an un-forced or passive state, or a partially released state), to lock or secure the bracket connector 150 to the bracket 160.

The bracket (or female connector element) 160 shown in FIG. 16 includes a base or body portion 162 having a back surface (surface facing inward toward the plane of the page in FIG. 16) for securing to an outer surface of a patient's tooth. The back surface of the body portion 162 may be secured to a patient's tooth in any suitable manner including those described with regard to the bracket 142.

The bracket 160 includes two projections or wing members 163 and 164, extending from the base or body portion 162. The projections 163 and 164 are spaced apart from each other, to form a gap 165 between the projections. The gap 165 is wide enough to allow the bracket connector 150 to be received between the projections 163 and 164, when the bracket connector 150 is squeezed (or compressed) to a compressed state for installation. In some examples, the gap 165 is also sufficient to allow an installed bracket connector 150 to be squeezed (or compressed) to a compressed state (or further compressed state) and removed from the bracket 160, through the gap 165.

The projections 163 and 164 of the bracket 160 may have a dimension (the height or vertical dimension D of FIG. 16) that is no greater than the corresponding dimension (the height or vertical dimension of FIG. 15) of the gap 152d and the gap 153d, respectively, in the associated bracket connector 150. More specifically, the dimension D of the projections 163 and 164 is sufficiently small to allow the projections 163 and 164 to fit within the gaps 152d and 153d, respectively, of the bracket connector 150, when the bracket connector 150 is connected to the bracket 160 as shown in FIG. 17.

In certain examples, one or both of the projections 163 and 164 has an extension portion (such as extension portions 163a and 164a in FIG. 16) that extends over a portion of the gap 165 in a direction toward the other projection. The extension portion 163a and 164a can help hold and retain the arm sections 152 and 153 of the bracket connector 150, when the bracket 150 is connected to the bracket 160 as shown in FIG. 17. In other examples, the extension portions 163a and 164a may be omitted.

In certain examples, the bracket 160 may have a relatively small form factor or dimension (in the height or vertical dimension of FIG. 16), to increase bonding placement options and to provide or increase space between the bracket and the gingival. The gingival-facing edge of the bracket may be curved as shown in the drawings, or straight.

Figure 19:
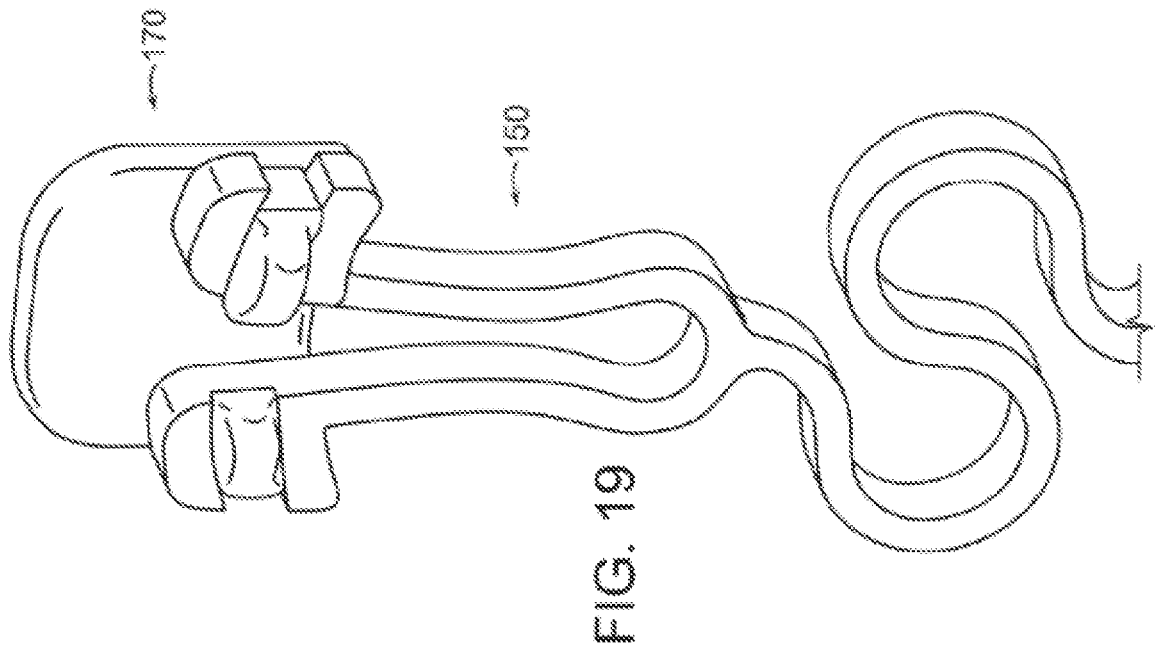
FIG. 19 is a perspective view of the bracket connector of FIG. 15 connected to the bracket of FIG. 18.
Figure 18:
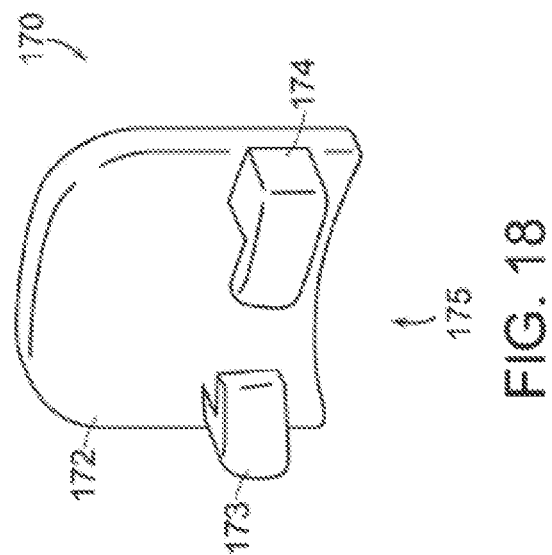
FIG. 18 is a perspective view of another bracket.

In other examples, the bracket may have a larger form factor. For example, the bracket 170 in FIGS. 18 and 19 may be configured (and operate) similar to the bracket 160 of FIG. 16, but has a larger base or body portion. In FIG. 18, the bracket 170 is shown, alone. In FIG. 19, the bracket 170 is shown in a connected state (connected with a bracket connector corresponding to bracket connector 150 of FIG. 15).

The bracket 170 includes two projections or wing members 173 and 174 (corresponding in structure and operation to the projections or wings 163 and 164 of the bracket 160) extending from a base or body portion 172. The base or body portion 172 may correspond to the base or body portion 162 in FIGS. 16 and 17. However, the base 172 in FIGS. 18 and 19 is larger in the occlusogingival dimension (in the height or vertical dimension of FIG. 18) than the base 162 in FIGS. 16 and 17. A larger base 172 can provide a larger bonding surface and, thus, a stronger bond to the patient's tooth.

Figure 21:
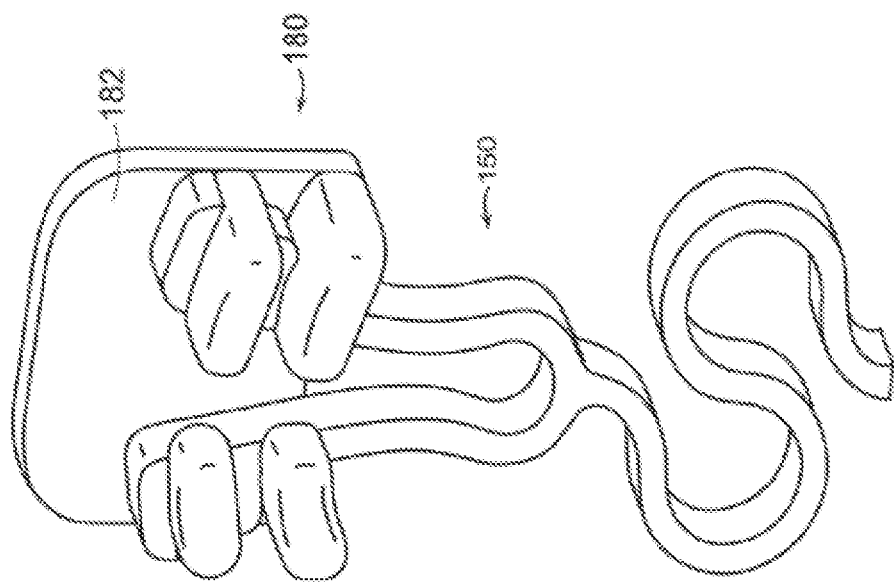
FIG. 21 is a perspective view of the bracket connector of FIG. 15 connected to the bracket of FIG. 20.
Figure 20:
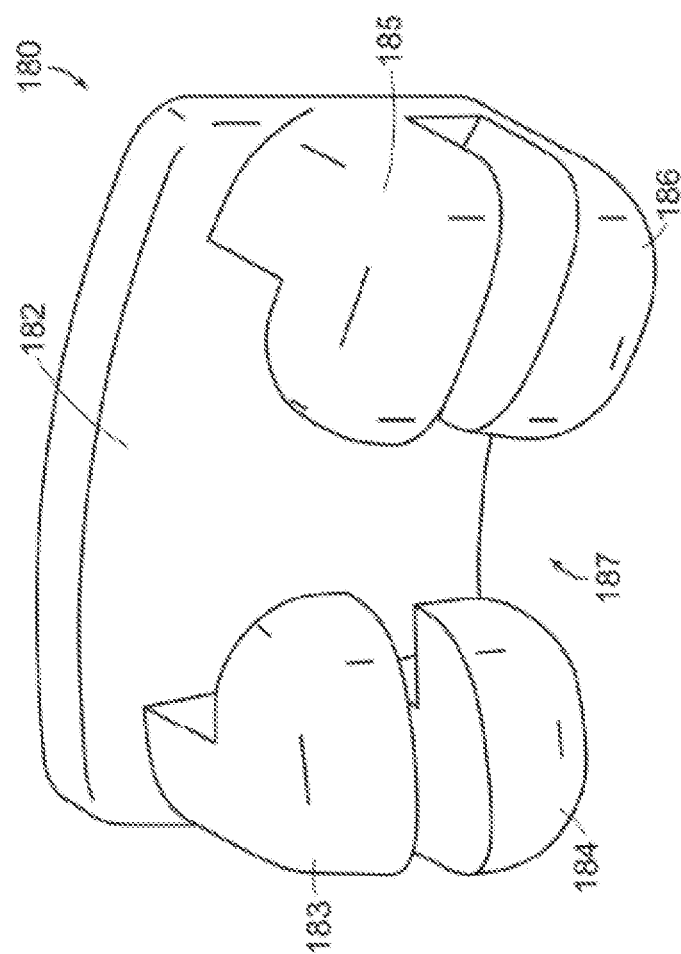
FIG. 20 is a perspective view of another bracket.

In other examples, the bracket may have more than two projections or wings. For example, the bracket 180 in FIGS. 20 and 21 may be configured (and operate) similar to the bracket 160 of FIG. 16, but has more than two projections or wings. In FIG. 20, the bracket 180 is shown, alone. In FIG. 21, the bracket 180 is shown in a connected state (connected with a bracket connector corresponding to bracket connector 150 of FIG. 15).

The bracket 180 includes four projections or wing members 183, 184, 185 and 186 extending from a base or body portion 182. The base or body portion 182 may correspond to the base or body portion 162 in FIGS. 16 and 17. Each of the projections or wing members 183, 184, 185 and 186 may correspond in structure and operation to the projections or wings 163 and 164 of the bracket 160. The projections or wing members are arranged such that two of the projections or wing members 183 and 184 are on one side of a gap 187, and two of the projections or wing members 185 and 186 are on an opposite side of the gap 187 (where the gap 187 corresponds to the gap 165 between the projections or wing members in FIG. 17). In addition, the projection or wing members of the bracket 180 are arranged such that the projection or wing members 183 and 184 are spaced apart from each other (in the height or vertical dimension of FIG. 20), and the projection or wing members 185 and 186 are spaced apart from each other in the occlusogingival dimension (in the height or vertical dimension of FIG. 20) such that a further gap is formed between those pairs of projections or wing members.

The gap 187 is wide enough to allow the bracket connector 150 to be received between the projections 183 and 184, and between the projections 185 and 186, when the bracket connector 150 is squeezed (or compressed) to a compressed state for installation. In addition, the gap between the projections 183 and 184 is larger than (or of sufficient size to receive) the projection 152c of the bracket connector 150, when the bracket connector 150 is connected to the bracket 180 as shown in FIG. 21. Similarly, the gap between the projections 185 and 186 is larger than (or of sufficient size to receive) the projection 153c of the bracket connector 150, when the bracket connector 150 is connected to the bracket 180 as shown in FIG. 21.

Alternatively, or in addition, the gap between the projections 183 and 184 may be configured to be larger than (or of sufficient size to receive) the projection 152b (instead of 152c), and the gap between the projections 185 and 186 may be configured to be larger than (or of sufficient size to receive) the projection 153b (instead of 153c), when the bracket connector 150 is connected to the bracket 180. In that case, the bracket connector 150 may connect to the bracket 180 in a lower position than shown in FIG. 21 (or in either the position shown in FIG. 21 or a lower position, for example, at the discretion of a clinician, doctor or other trained personnel).

Figure 23:
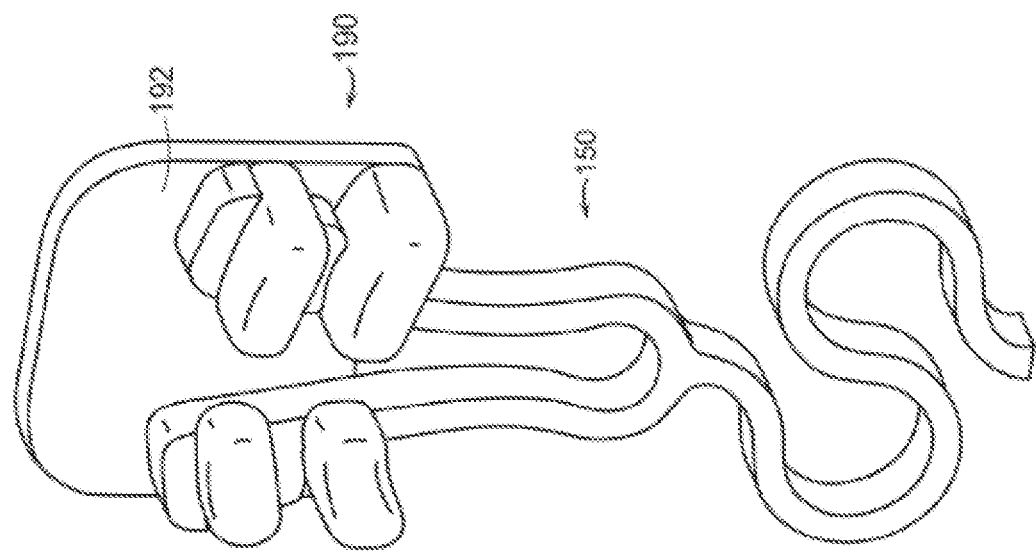
FIG. 23 is a perspective view of the bracket connector of FIG. 15 connected to the bracket of FIG. 22.
Figure 22:
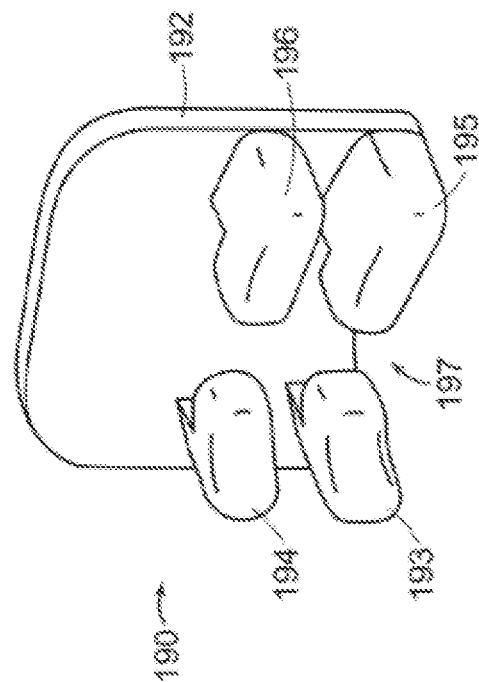
FIG. 22 is a perspective view of another bracket.

In other examples, the bracket may be configured with four (or more) projections or wing members, but have a larger form factor. For example, the bracket 190 in FIGS. 22 and 23 may be configured (and operate) similar to the bracket 180 of FIGS. 20 and 21, but has a larger base or body portion. In FIG. 22, the bracket 190 is shown, alone. In FIG. 23, the bracket 190 is shown in a connected state (connected with a bracket connector corresponding to bracket connector 150 of FIG. 15).

The bracket 190 includes four projections or wing members 193, 194, 195 and 196 (corresponding in structure and operation to the projections or wings 183, 184, 185 and 186 of the bracket 180) extending from a base or body portion 192. The base or body portion 192 may correspond to the base or body portion 182 in FIGS. 20 and 21. However, the base 192 in FIGS. 22 and 23 is larger (in the height or vertical dimension of FIG. 22) than the base 182 in FIGS. 20 and 21 and, thus, can provide additional benefits as described herein.

In each of the examples described with regard to FIGS. 16-23, one or more projections or wing members are arranged on one side (e.g., the left side in the drawings) of a centrally-located gap 165, 175, 187, 197, and one or more projections or wing members are arranged on the opposite side (e.g., the right side in the drawings).

In any of the examples described with regard to FIGS. 16-23 or other examples, the bracket may include one or more further projections or wings arranged above or below the gap 165, 175, 187 or 197 (for example, centered on a vertical axis located between the one or more projections or wing members located on the left side of the gap, and the one or more projections or wing members located on the right side of the gap).

Figure 24:
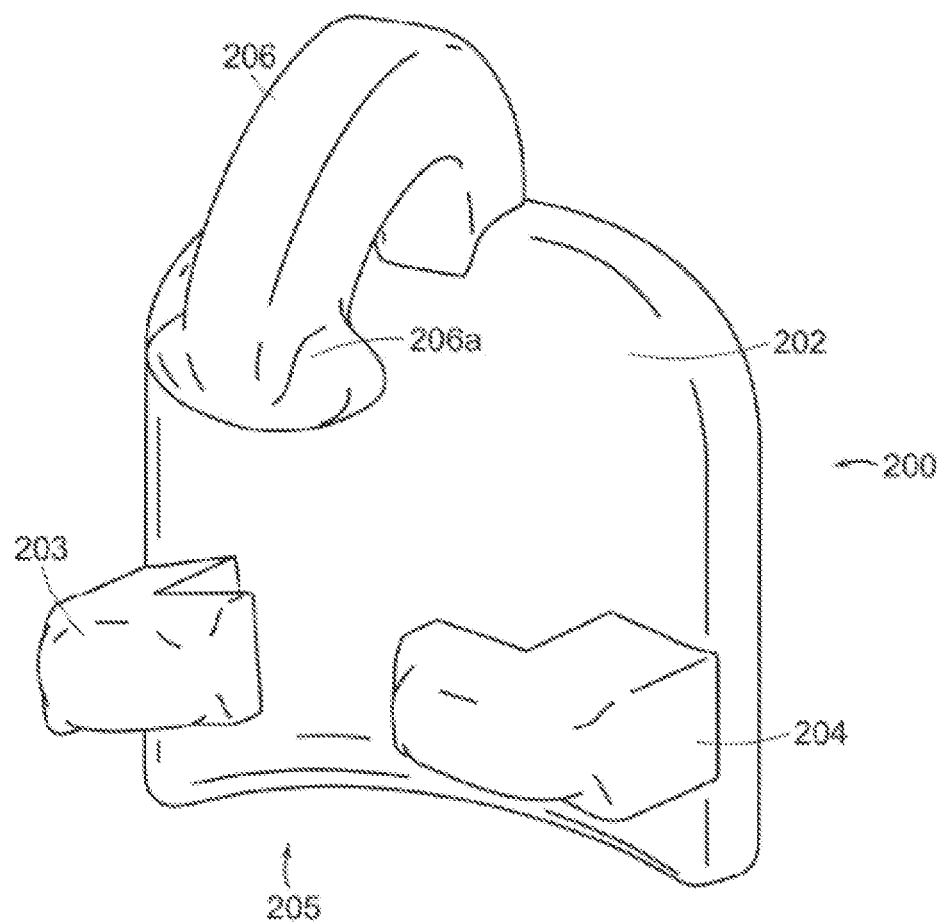
FIG. 24 is a perspective view of another bracket.

For example, the bracket 200 in FIG. 24 is configured similar to the bracket 170 of FIG. 18, but includes a further projection or wing arranged above the gap between the left and right side projection or wing members. More specifically, the bracket 200 includes a base or body portion 202 (corresponding to the base or body portion 172 of the bracket 170), and two projections or wing members 203 and 204 (corresponding in structure and operation to the projections or wing members 173 and 174 of the bracket 170), defining a gap 205 between the projections or wing members. The bracket 200 includes a further projection or wing 206 arranged above the gap 205.

The further projection or wing member 206 extends outward from the base or body portion 202 (in the same direction that the projections or wing members 203 and 204 project). In the example in FIG. 24, the further projection or wing member 206 extends from a side edge of the base or body portion 202 (the edge, in the FIG. 24 orientation, forming a top side edge extending between the rear-facing bonding surface, and the front or outward facing surface from which the projections or wing members 203 and 204 extend). In other examples, the further projection or wing member 206 may extend outward directly from the front or outward facing surface of the base or body portion 202.

In the example in FIG. 24, the further projection or wing member 206 curves downward toward the gap 205 or has a portion that extends downward toward the gap 205. In certain examples, the further projection or wing member 206 may have an overall curved or hook shape (as shown in the example in FIG. 24). The further projection or wing member 206 has a free or distal end portion 206a. In certain examples, the free end portion 206a of the further projection or wing member 206 may include one or more features for holding or retaining one or more bands, wires, ties or other connection structure. In the example in FIG. 24, the distal end portion 206a of the further projection or wing member 206 has a widened shape (relative to other portions or the rest of the further projection or wing member 206). Other examples include other suitable shapes or features for assisting with retaining one or more bands, wires, ties or other connection structure.

Figure 25:
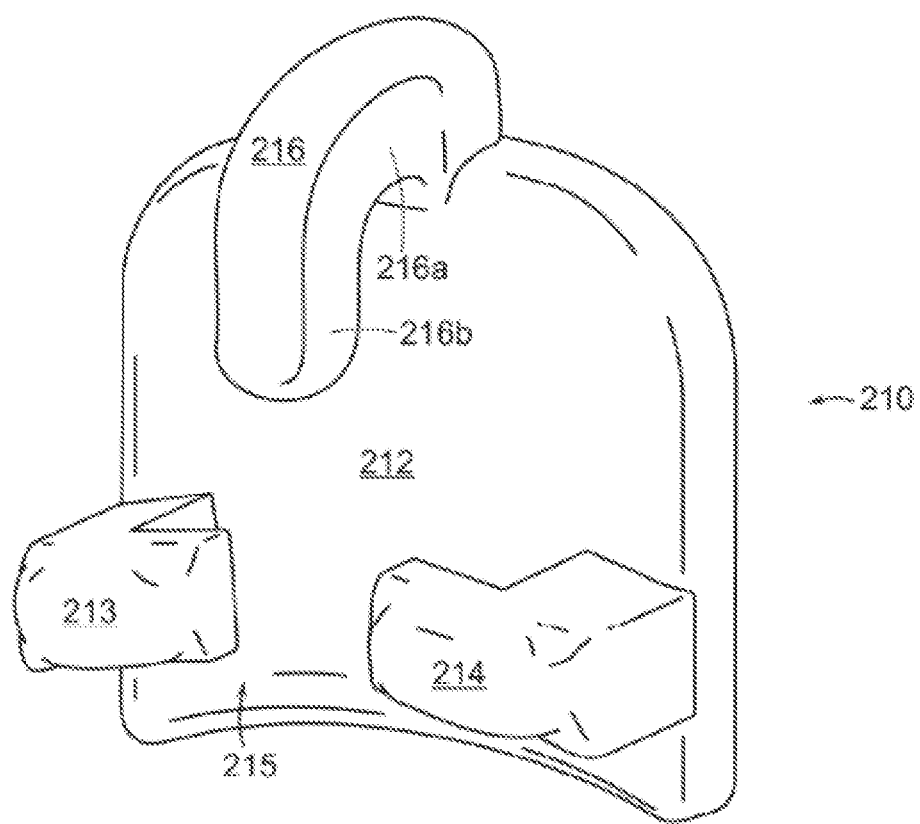
FIG. 25 is a perspective view of another bracket.

Another example of a bracket 210 in FIG. 25 is configured similar to the bracket 200 in FIG. 24. The bracket 210 includes a base or body portion 212 (corresponding to the base or body portion 202 of the bracket 200), and two projections or wing members 213 and 214 (corresponding in structure and operation to the projections or wing members 203 and 204 of the bracket 200), defining a gap 215 between the projections or wing members. The bracket 210 includes a further projection or wing member 216 arranged above the gap 215. The further projection or wing member 216 extends outward from the base or body portion 212 and includes a first section 216a that extends generally linearly and perpendicular relative to the plane of the bonding surface of the base or body portion 212. In the example in FIG. 25, the further projection or wing member 216 extends from a side edge of the base or body portion 212 (the edge, in the FIG. 25 orientation, forming a top side edge extending between the bonding surface that faces inward of the page, and the outward facing surface from which the projections or wing members 213 and 214 extend). In other examples, the further projection or wing member 216 may extend outward directly from the front or outward facing surface of the base or body portion 212.

The further projection or wing member 216 includes a second section 216b that extends downward from the first section 216a, toward the gap 215. In the example in FIG. 26, the distal end portion of the further projection or wing member 216 is not widened relative to other portions of the further projection or wing member 216. However, in other examples, the distal end portion of the further projection or wing member 216 may include one or more features for holding or retaining one or more bands, wires, ties or other connection structure as described above, for example, with regard to the further projection or wing member 206 in FIG. 24.

Figure 26:
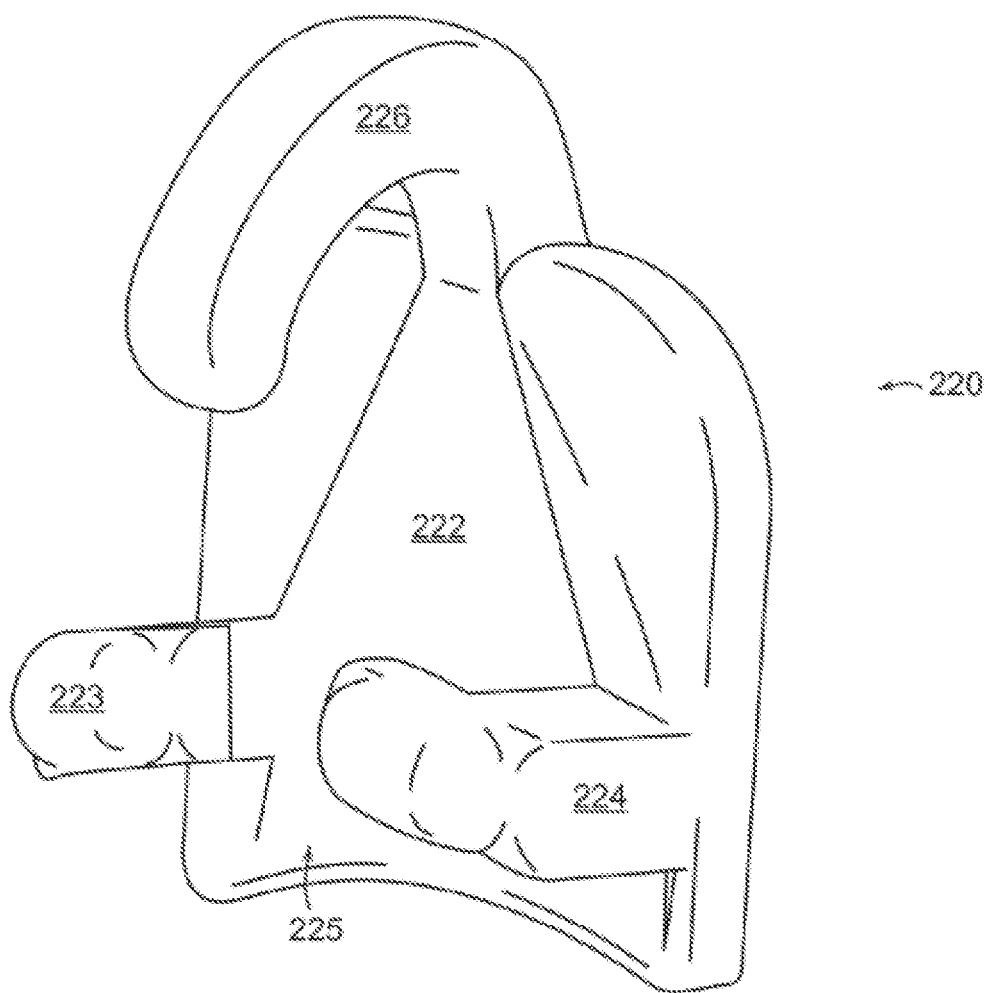
FIG. 26 is a perspective view of another bracket.

Another example of a bracket 220 in FIG. 26 is configured similar to the bracket 200 in FIG. 24 and the bracket 210 in FIG. 25. The bracket 220 includes a base or body portion 222 (corresponding to the base or body portions 202 and 212 of the brackets 200 and 210), and two projections or wing members 223 and 224 (corresponding in structure and operation to the projections or wing members 203 and 204 of the bracket 200 or the projections or wing members 213 and 214 of the bracket 212), defining a gap 225 between the projections or wing members. The bracket 220 includes a further projection or wing member 226 arranged above the gap 225.

In FIG. 26, the further projection or wing member 226 extends outward from the base or body portion 222 and has a curved or a hook shape, similar to the shape of the further projection or wing member 206 in FIG. 24. However, in the example in FIG. 26, the distal end portion of the further projection or wing member 226 is not widened relative to other portions of the further projection or wing member 226.

In any of the examples described with regard to FIGS. 16-26 or other examples, the bracket may include a shield portion arranged above or below the gap 165, 175, 187 or 197 (for example, centered on a vertical axis located between the one or more projections or wing members located on the left side of the gap, and the one or more projections or wing members located on the right side of the gap).

Figure 27:
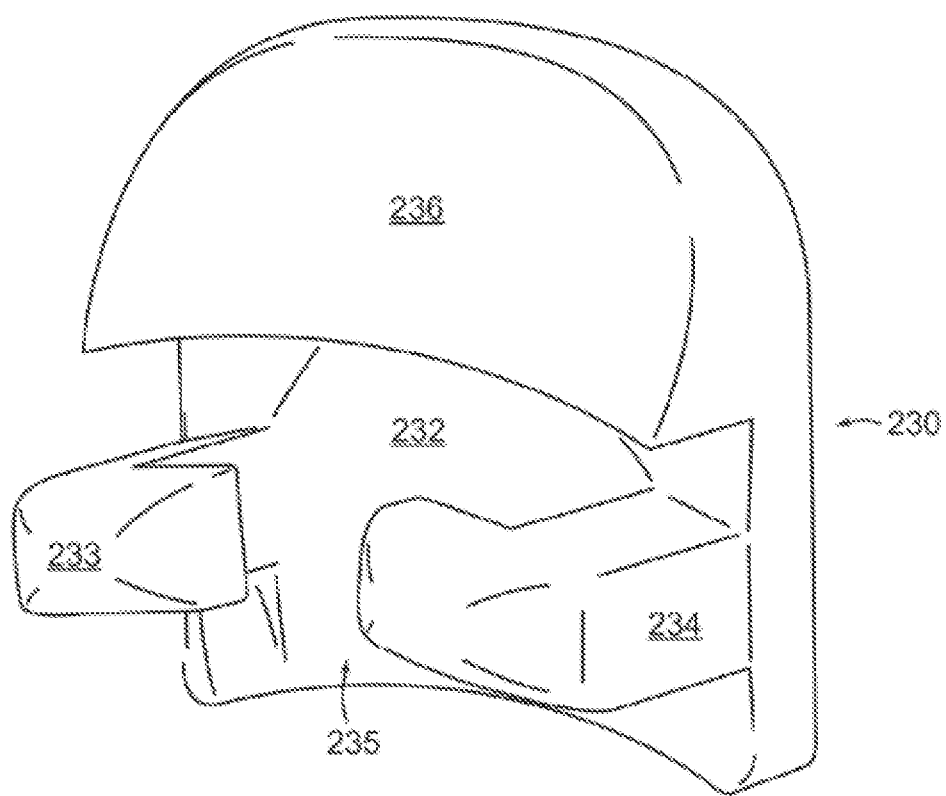
FIG. 27 is a perspective view of another bracket.

For example, the bracket 230 in FIG. 27 is configured similar to the bracket 170 of FIG. 18, but includes a shield member above the gap between the left and right side projection or wing members. More specifically, the bracket 230 includes a base or body portion 232 (corresponding to the base or body portion 172 of the bracket 170), and two projections or wing members 233 and 234 (corresponding in structure and operation to the projections or wing members 173 and 174 of the bracket 170), defining a gap 235 between the projections or wing members. The bracket 230 includes a shield member 236.

The shield member 236 extends from the base or body portion 232, at a location above the gap 235. In particular examples, the shield member 236 extends an entire width dimension of the base or body portion 232 (from the right to the left sides of the base or body portion 232 in the orientation of FIG. 27) and is adjacent but spaced from the projections or wing members 233 and 234 (above the projections or wing members 233 and 234 in the orientation of FIG. 27). The shield member 236 can deflect forces from the bracket when the patient bites down onto food, to decrease the chance of the bracket becoming de-bonded from the patient's tooth. Additionally, or alternatively, the shield member 236 may provide a relatively smooth surface or canopy adjacent the projections or wing members 233 and 234 and the gap 235, which can feel smoother and more comfortable to the patient, and can provide a more favorable appearance.

In the examples described with reference to FIGS. 16-27, the bracket includes one or more projections or wing members arranged on one side of a gap (e.g., gap 165, 175, 187, 197, 205, 215, 225 or 235) and one or more projections or wing members are on an opposite side of the gap, separated in a horizontal direction relative to the orientation in the drawings. In any of those or other examples, the one or more projections or wing members may be arranged on opposite sides of the gap, in a vertical direction.

Figure 28:
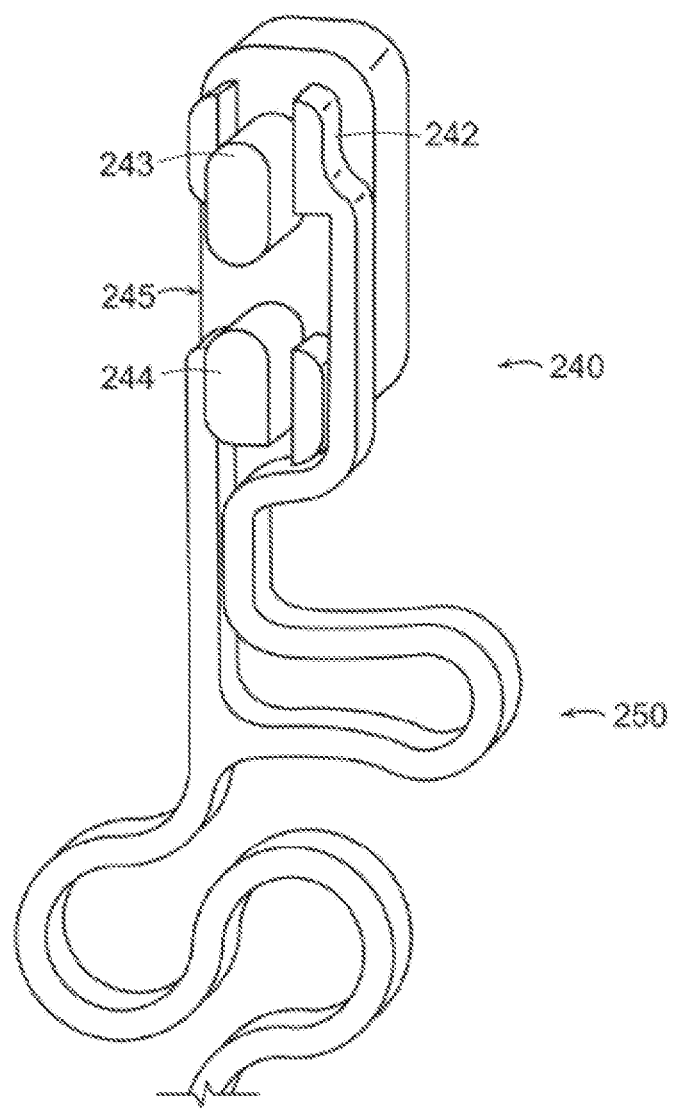
FIG. 28 is a perspective view of another bracket connector connected to another bracket.

For example, the bracket 240 in FIG. 28 is configured similar in some ways to the bracket 160 of FIG. 16, but includes a pair of projection or wing members separated by a gap in a vertical direction. More specifically, the bracket 240 includes a base or body portion 242 (corresponding to the base or body portion 162 of the bracket 160), and two projections or wing members 243 and 244 (corresponding in structure and operation to the projections or wing members 163 and 164 of the bracket 160), defining a gap 245 between the projections or wing members.

However, the projections or wing members 243 and 244 are arranged adjacent each other in the vertical direction (such that one of the projections or wing members is above the other projection or wing member) in the orientation of FIG. 28. In that example, a bracket connector (or male connector element) 250 is configured with arm sections that flex together (to compress in at least the vertical dimension), similar to the resilient flexing function and operation described with regard to the arms 152 and 153 of the bracket connector 150 in FIG. 15, but in a vertical direction. A vertical connection configuration (as provided with bracket connector 250 and bracket 240) can be beneficial in certain contexts, such as where minimal space in a widthwise or horizontal direction is limited or other contexts in which a bracket having a relatively narrower width is desired.

Any of the brackets described in any of the examples of FIGS. 16-28 may be made of any suitable material or materials, such as, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in single structure.

The bracket connectors (or male connector elements) described in any of the examples of FIGS. 15. 17, 19, 21, 23 and 28 may be made of any suitable material or materials, such as, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in single structure. However, in particular examples, the bracket connectors described in those examples are made by cutting a two dimensional (2D) form of the appliance from a 2D sheet of material and bending the 2D form into a desired 3D shape of the appliance, according to processes as described in U.S. patent application Ser. No. 15/370,704, filed Dec. 5, 2016 or other suitable processes.

Such bracket connectors can be beneficial in certain contexts, such as where space is limited, as the bracket connectors can be made relatively small. Additionally, or alternatively, brackets and bracket connectors as described in FIGS. 15-28 can be made to be relatively comfortable, easy to install and remove (using a squeezing action).

Further examples of bracket connectors (or male connector elements) that may be employed with any of the appliance or method examples described herein or in U.S. patent application Ser. No. 15/370,704, filed Dec. 5, 2016. Also, any of the appliance or appliance member examples described herein, one or more (or all) of the bracket connectors (or male connector elements) may be replaced by one or more cap connector elements configured to fit over a single tooth (or a plurality of teeth), such as but not limited to the cap connector elements described in U.S. patent application Ser. No. 15/370,704, filed Dec. 5, 2016.

Certain appliances (and methods of making an appliance) according to examples described herein may be configured with Z embodiment features or a combination of X and Z embodiment features. Further examples of certain Z embodiment features are described herein, with reference to FIGS. 29-38. Any of the appliances (or methods of making an appliance) according to examples described herein may be configured with Z embodiment features (or Z embodiment features in combination with X embodiment features) as shown and described with regard to FIGS. 29-38. Other appliances according (or methods) according to examples described herein may include other suitable Z embodiment features.

Figure 29:
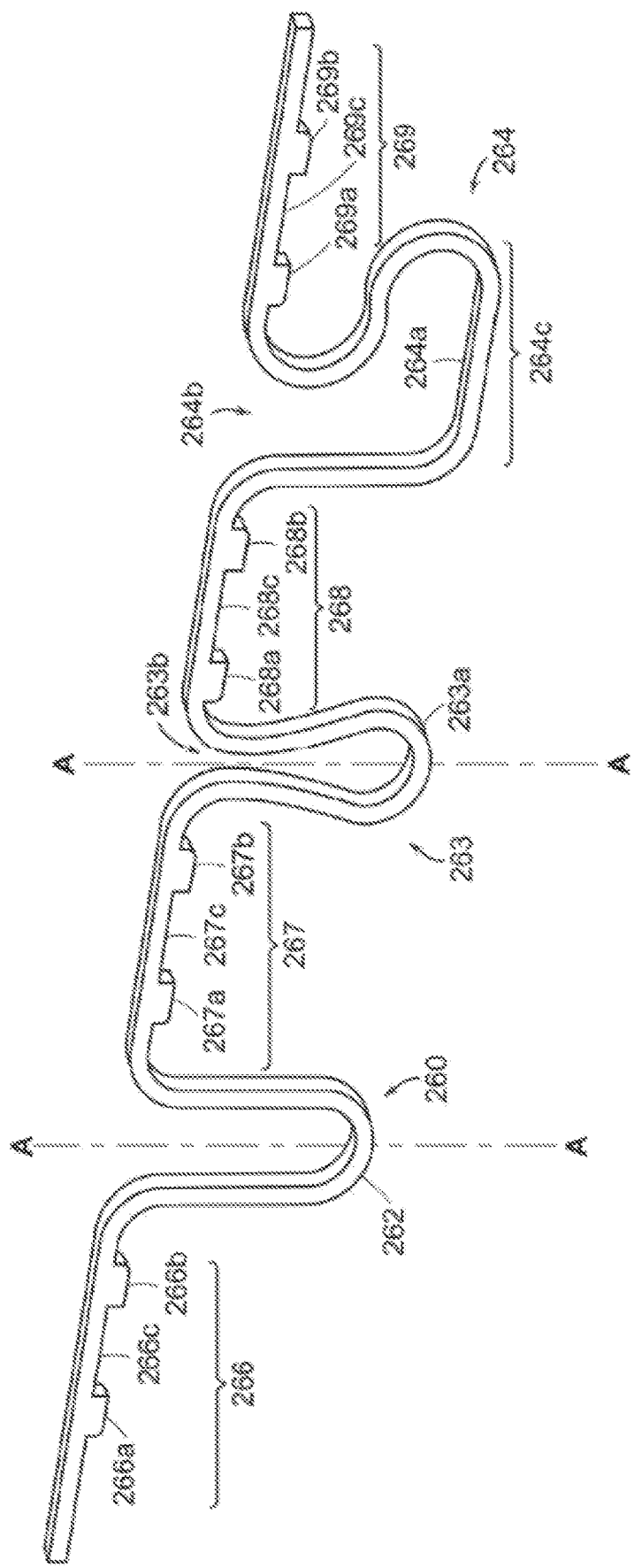
FIG. 29 is a diagram of examples of loop or curved features and bracket connectors of an appliance.

FIG. 29 shows certain examples of Z embodiment features, including a rigid bar 260 having loop or curved features and bracket connectors (or male connector elements). A rigid bar as described with regard to the rigid bar 260 (or features thereof) may be included in Z embodiment features on any of the appliances described herein, such as, but not limited to, the Z embodiment features in the rigid bars 26 or 27 in FIGS. 2 and 3, or in the rigid bars 53 and 54 in FIG. 5, or in the rigid bars 66, 76, 86, 96 of FIGS. 6-9. In other examples, a rigid bar as described with regard to the rigid bar 260 (or features thereof) may be included in Z embodiment features of other suitable appliances (or methods).

The rigid bar 260 includes various examples of loop or curved features 262, 263 and 264 that may be included in Z embodiment features of any of the appliances described herein. The loop or curved feature 262 has a U shape configuration that is generally symmetrical about an axis A extending through the center of the U shape. The loop or curved feature 263 also has a generally U shape configuration (symmetrical about an axis A), but is wider at the closed or loop end 263*a* relative to the open end 263*b* of the general U shape. In other examples, the loop or curved feature 262 or 263 may be asymmetrical about a central axis and, thus, may extend to one side of the axis a greater distance or in a different curvature or shape, than on the other side of the axis.

The loop or curved feature 264 has a generally L shape loop configuration, which is also wider at its closed or loop end 264*a* relative to its open end 264*b*. The loop or curved feature 264 includes a section (264*c*) that extends laterally (to one side) relative to the width of the open end 264*b*. In the example in FIG. 29, the section 264*c* extends to the left, relative to the width of the open end 264*b*. In other examples, the section 264*c* may extend to the right, relative to the width of the open end 264*b*. In yet other examples, the loop or curved feature 264 may include a section 264*c* extending to the left of the open end 264*b*, and a further section (similar to section 264*c*) extending to the right of the open end 264*b*, to form a T shaped loop. In other examples, the rigid bar 260 may include loop or curved features having other suitable shapes or configurations.

In the examples shown in FIG. 29, each of the loop or curved features 262, 263 and 264 is formed of a curved or bent portion of the rigid bar 260 (curved or bent in the shape shown and described). In other examples, one or more (or each) of the loop or curved features may be formed separately of other sections of the rigid bar 260 and then coupled to the other sections of the rigid bar 260 to form the overall length dimension of the rigid bar 260.

Figure 38:
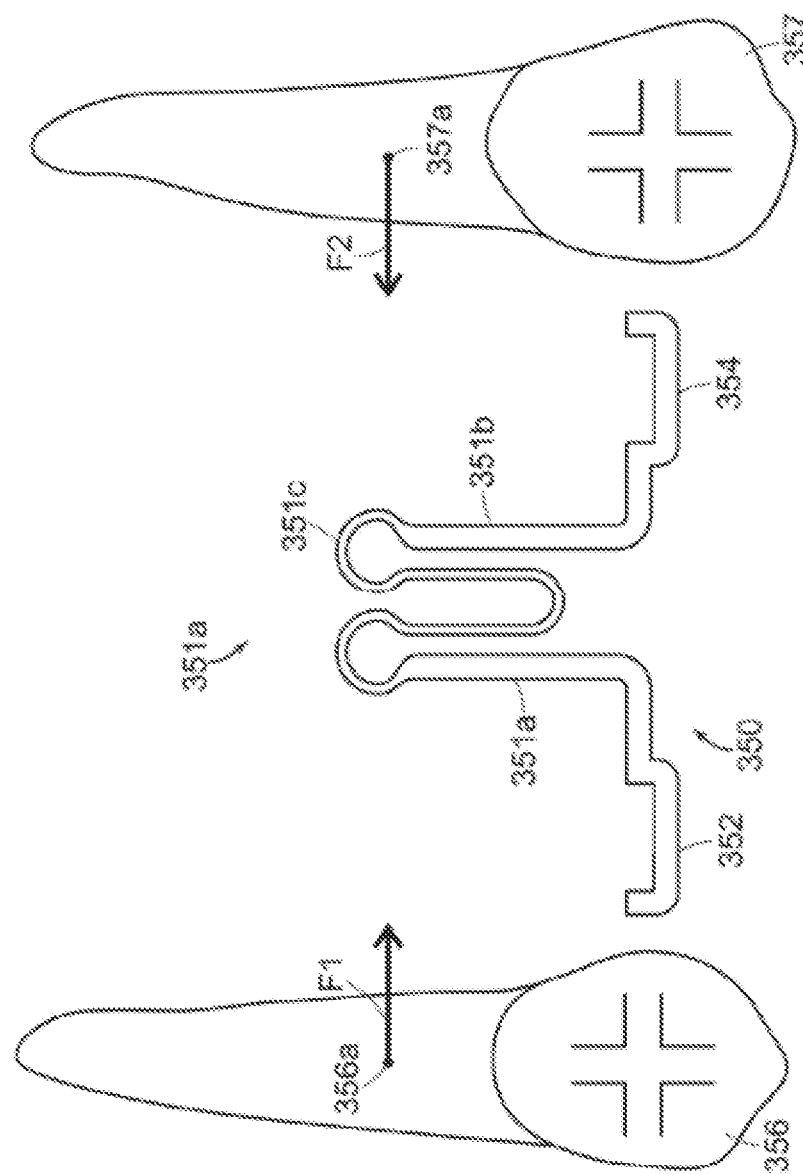
FIG. 38 is a diagram of a further example of a loop or curved feature and bracket connectors of an appliance.

In the examples shown in FIG. 29, the section of the rigid bar 260 that forms each of the loop or curved features 262, 263 and 264 has a width dimension (in the right-left horizontal direction of FIG. 29) and a thickness dimension (in the direction into the page of FIG. 29) that remains constant over the entire length of the loop or curved feature. In other examples, one or more (or each) of the loop or curved features 262, 263 and 264 has a width dimension or a thickness dimension (or both) that varies over some (or all) of the length of the loop or curved feature, such that one or more portions of the rigid bar along the loop or curved feature are wider or thicker than one or more other portions of the rigid bar along the same loop or curved feature. The shape and dimension (and other aspects of the configuration) of each loop or curved feature can affect or provide certain characteristics, including, but not limited to flexibility, bias force magnitude, bias force direction, durability and other characteristics. For example, a loop or curved feature having a generally U shape (such as the loop or curved feature 262) may provide sufficient forces for typical tooth aligning. A loop or curved feature having a compressed U shape (such as the loop or curved feature 263 may be useful tooth aligning, in contexts in which space is limited (such as tooth crowding). A loop or curved feature having an L shaped loop (such as the loop or curved feature 264 may be useful in contexts in which an extrusion or intrusion is needed. A loop or curved feature having a shape of feature 351 as shown in FIG. 38 (discussed below) may be useful in extraction cases, for example, where the arm sections are wider or thicker in a dimension, to act as power arms and apply sufficient force on a center of resistance of one or two teeth, to help move a tooth without tipping the tooth. Accordingly, in certain examples of appliances and methods, the shape, dimension and other aspects of one or more (or each) loop or curved feature in the appliance is selected or configured to provide one or more of a desired flexibility, bias force magnitude, bias force direction, durability or other characteristics. Loop or curved feature configurations as shown at 262, 263 and 264 in FIG. 29 or other examples of loop or curved features may be included in any appliances (or methods) having one or more Z embodiment features. Some of such other examples of loop or curved features are described below, with regard to FIGS. 36-38.

Referring again to FIG. 29, the rigid bar 260 includes examples of bracket connectors (or male connector elements) that may be included in any of the Z embodiment features of example appliances or methods described herein. Other appliances or methods examples as described herein may include other suitable bracket connectors (or male connector elements) including, but not limited to other examples described herein or in U.S. patent application Ser. No. 15/370,704, filed Dec. 5, 2016.

In FIG. 29, rigid bar 260 includes a respective bracket connector 266, 267, 268 and 269 on each respective side (right and left side) of each loop or curved feature 262, 263 and 264, such that one respective loop or curved feature is located between each pair bracket connectors along the length dimension of the rigid bar 260. In other examples, two or more loop or curved features are located between one or more (or each) pair of adjacent bracket connectors. In other examples, two or more bracket connectors are located between one or more (or each) pair of adjacent loop or curved features along the length dimension of the rigid bar 260.

In the example in FIG. 29, the bracket connectors 266, 267, 268 and 269 have a similar configuration. In other examples, one or more (or each) bracket connector on an appliance may have a different configuration than one or more (or each) other bracket connector on the same appliance. Each of the bracket connectors 266, 267, 268 and 269 includes a first extension portion and a second extension portion (represented by the first extension portion 266a and the second extension portion 266b of the bracket connector 266) that are separated by a length section (represented by 266c of the bracket connector 266) of the rigid bar located between the first and second extension portions. In certain examples, the first and second extension portions (e.g., 266a and 266b) are formed integral and unitary with the rigid bar 260 (e.g., as raised, thickened or widened portions of the rigid bar). In other examples, the first and second extension portions (e.g., 266a and 266b) are formed separate from, and then coupled to the rest of the rigid bar 260 by any suitable coupling mechanism such as, but not limited to adhesive, welding, soldering, or the like.

In the example in FIG. 29, the extension portions of each of the bracket connectors 266, 267, 268 and 269 extends or projects from the rigid bar 260 in a direction toward the patient's gums (the gingival direction), when the appliance is installed. In other examples, such as shown in FIG. 30, one or more (or all) of the extension portions of each of the bracket connectors may extend or project from the rigid bar in a direction away the patient's gums (the occlusal direction), when the appliance is installed.

Figure 30:
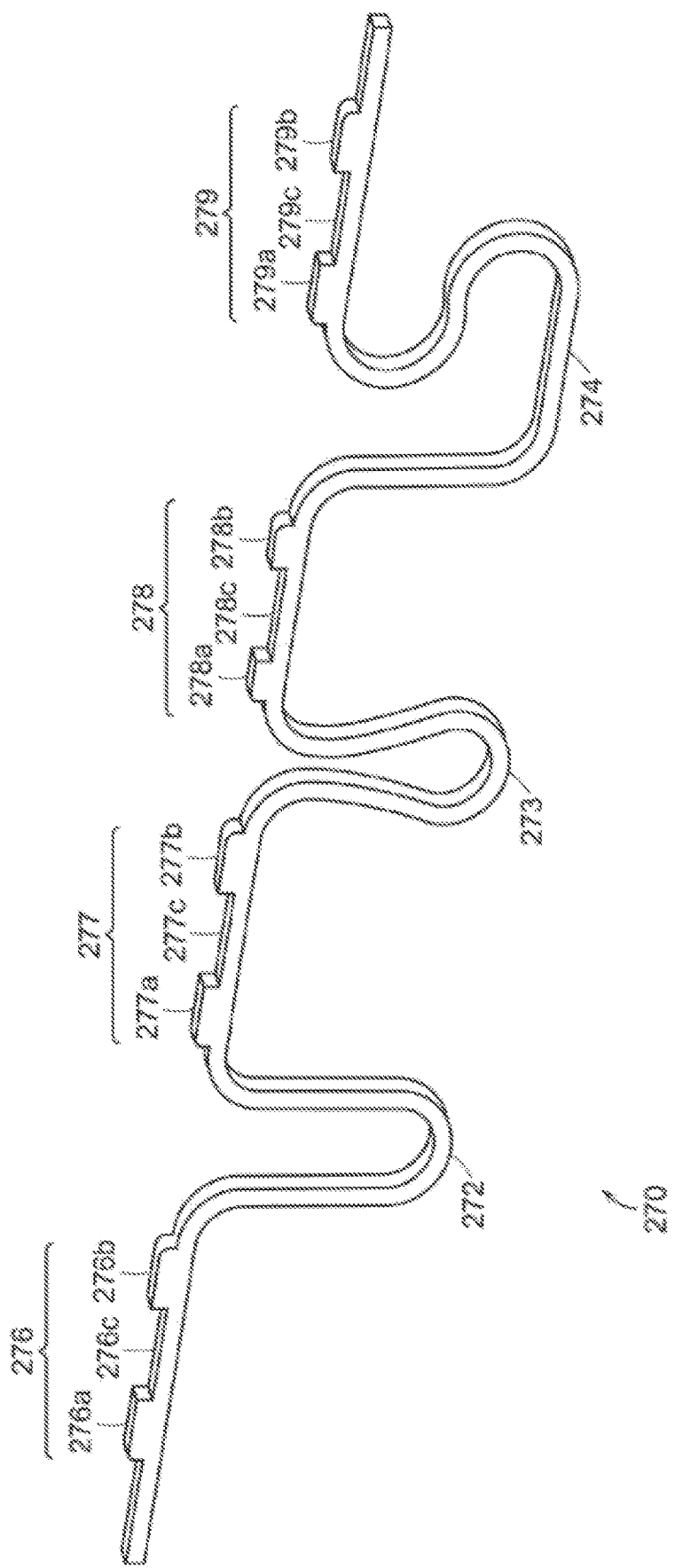
FIG. 30 is a diagram of additional examples of loop or curved features and bracket connectors of an appliance.

More specifically, the example in FIG. 30 includes a rigid bar 270 having loop or curved features 272, 273 and 274 (corresponding to the rigid bar 260 and loop or curved feature 262, 263 and 264 of FIG. 28). A plurality of bracket connectors 276, 277, 278 and 279 are provided on the rigid bar 270, for example, in a manner similar to that described for the bracket connectors 266, 267, 268 and 269 in FIG. 29). However, each of the bracket connectors 276, 277, 278 and 279 in FIG. 30 is formed of first and second extension portions (such as the first extension portion 276a and the second extension portion 276b) that extend in the occlusal direction, when the appliance is installed. Similar to the bracket connectors described with regard to FIG. 29, the bracket connectors 276, 277, 278 and 279 in FIG. 30 include a length section (represented by 276c of the bracket connector 276) of the rigid bar located between the first and second extension portions.

Figure 31:
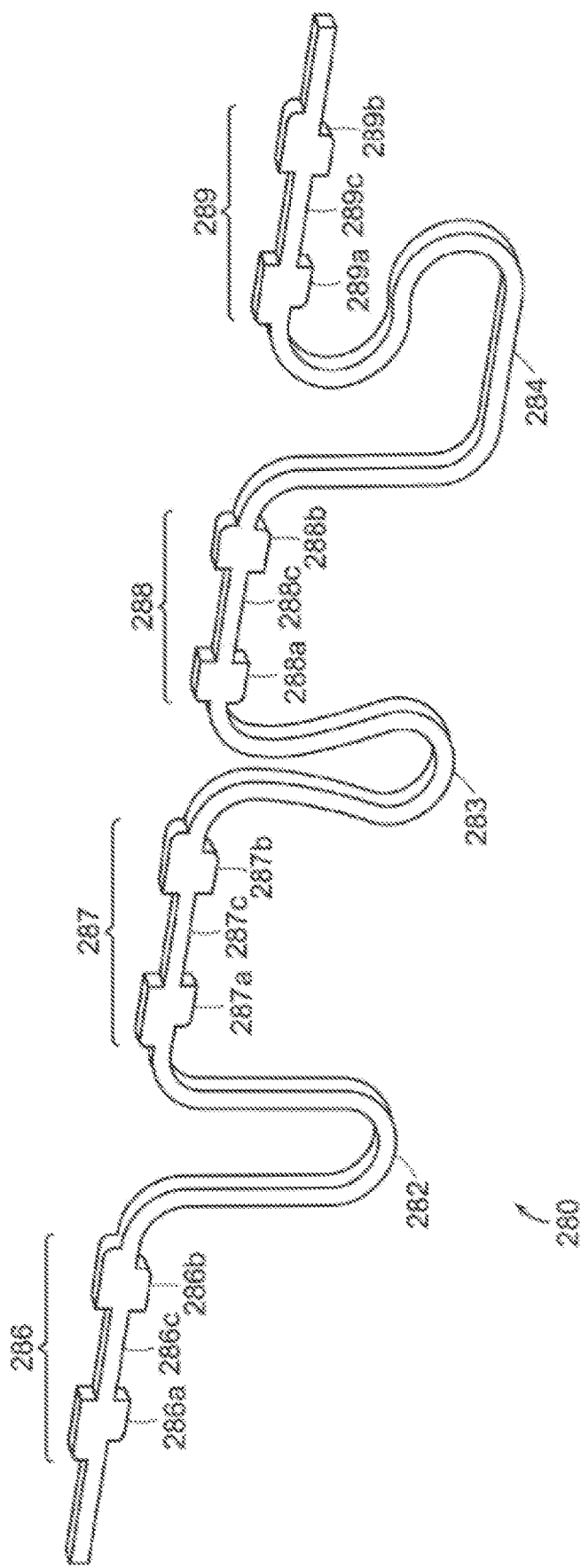
FIG. 31 is a diagram of examples of loop or curved features and bracket connectors of an appliance.

In other examples, such as shown in FIG. 31, one or more (or all) of the extension portions of each of the bracket connectors may extend or project from the rigid bar in two directions, both toward and away the patient's gums (the gingival and the occlusal directions), when the appliance is installed. More specifically, the example in FIG. 31 includes a rigid bar 280 having loop or curved features 282, 283 and 284 (corresponding to the rigid bar 260 and loop or curved feature 262, 263 and 264 of FIG. 29). A plurality of bracket connectors 286, 287, 288 and 289 are provided on the rigid bar 280, for example, in a manner similar to that described for the bracket connectors 266, 267, 268 and 269 in FIG. 29). However, each of the bracket connectors 286, 287, 288 and 289 in FIG. 29 is formed of first and second extension portions (such as the first extension portion 286a and the second extension portion 286b) that extend in both the gingival direction and the occlusal direction, when the appliance is installed. Similar to the bracket connectors described with regard to FIG. 29, the bracket connectors 286, 287, 288 and 289 in FIG. 29 include a length section (represented by 286c of the bracket connector 286) of the rigid bar located between the first and second extension portions.

In other examples, one or more (but not all) of the bracket connectors on an appliance have a configuration as described with regard to FIG. 29 with extension portions that extend in the gingival direction, while one or more (but not all) of the bracket connectors on an appliance have a configuration as described with regard to FIG. 30 with extension portions that extend in the occlusal direction, when the appliance is installed. In other examples, one or more (but not all) of the bracket connectors on an appliance have a configuration as described with regard to FIG. 29 with extension portions that extend in the gingival direction, while one or more (but not all) of the bracket connectors on an appliance have a configuration as described with regard to FIG. 31 with extension portions that extend in the two direction, when the appliance is installed. In yet other examples, one or more (but not all) of the bracket connectors on an appliance have a configuration as described with regard to FIG. 30 with extension portions that extend in the gingival direction, while one or more (but not all) of the bracket connectors on an appliance have a configuration as described with regard to FIG. 31 with extension portions that extend in the two directions, when the appliance is installed. In yet other examples, one or more (but not all) of the bracket connectors on an appliance have a configuration as described with regard to FIG. 29 with extension portions that extend in the gingival direction, while one or more (but not all) of the bracket connectors on an appliance have a configuration as described with regard to FIG. 30 with extension portions that extend in the occlusal direction, when the appliance is installed, and while one or more (but not all) of the bracket connectors on an appliance have a configuration as described with regard to FIG. 31 with extension portions that extend in the two directions, when the appliance is installed.

Figure 32:
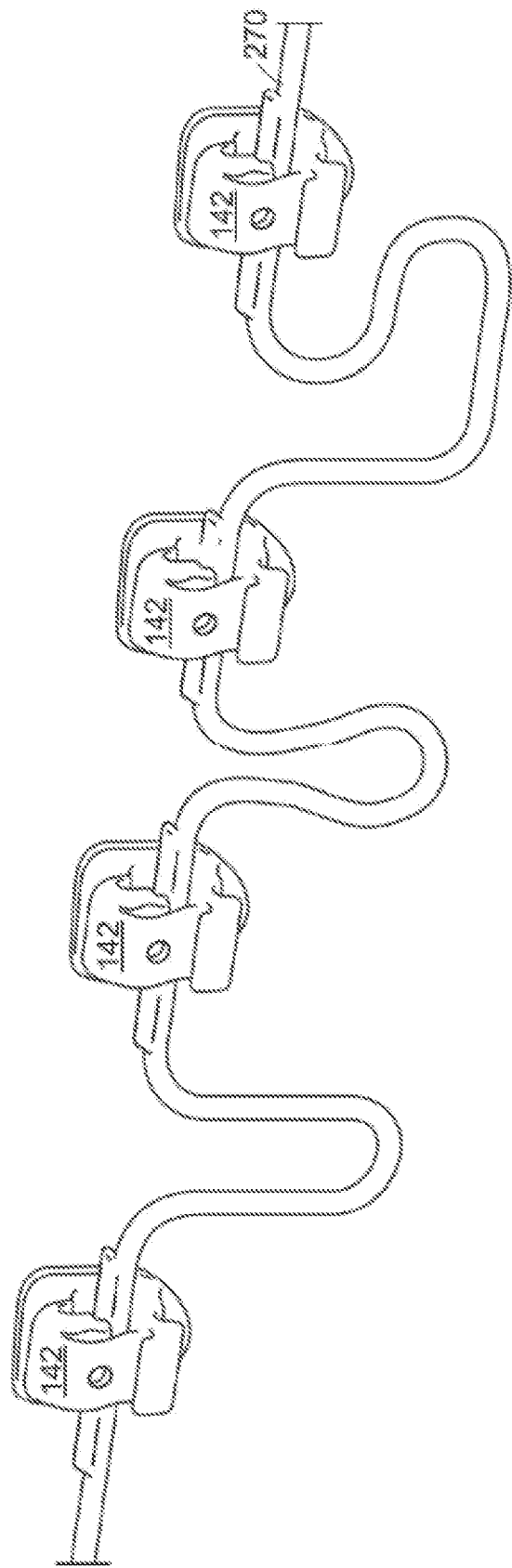
FIG. 32 is a diagram of loop or curved features and bracket connectors of FIG. 30, connected to brackets.

Bracket connectors (or male connector elements) as shown in the examples in FIGS. 29-31 may be configured to selectively connect with a bracket having any suitable configuration to which the bracket connect can secure. In certain examples, the bracket connectors (or male connector elements) in the examples in FIGS. 29-31 may be configured to selectively connect with a bracket as described with reference to the bracket 142 example in FIG. 14. In such examples, the receptacle 142f of the bracket 142 is configured to receive at least a portion of a length section of the rigid bar located between the first and second extension portions of a bracket connector (e.g., one of the length sections 266c, 276c and 286c of the bracket connectors 266, 276 and 286 of FIGS. 29-31), when the bracket connector is connected to the bracket 142. For example, FIG. 32 shows the rigid bar 270 (from the example in FIG. 30), connected to four brackets (each corresponding to a bracket 142 as shown in the example in FIG. 14). In the example in FIG. 32, each of the brackets 142 may be secured to (e.g., bonded to) a different respective one of the patient's teeth (not shown).

In the examples of FIGS. 29-32, the bracket connectors (or male connector elements) may be configured to prevent lateral (mesiodistal) movement of the appliance, relative to the brackets, when the appliance is installed (connected to the brackets). Accordingly, the first and second extension portions of the bracket connectors 266, 276 and 286 of FIGS. 29-31 may be configured to be larger in one or more cross-section dimension than the cross section dimension of the receptacle 142f of the bracket 142, such that the first and second extension portions are sufficiently adjacent or abutted against the bracket 142 to inhibit lateral movement of the bracket connector (and the appliance) relative to the bracket 142, when the bracket connector is connected to the bracket 142. In other examples, the extension portions of the bracket connectors may have any suitable shape that inhibits lateral movement of the bracket connector (and the appliance) relative to the bracket 142, when the bracket connector is connected to the bracket 142.

Figure 33:
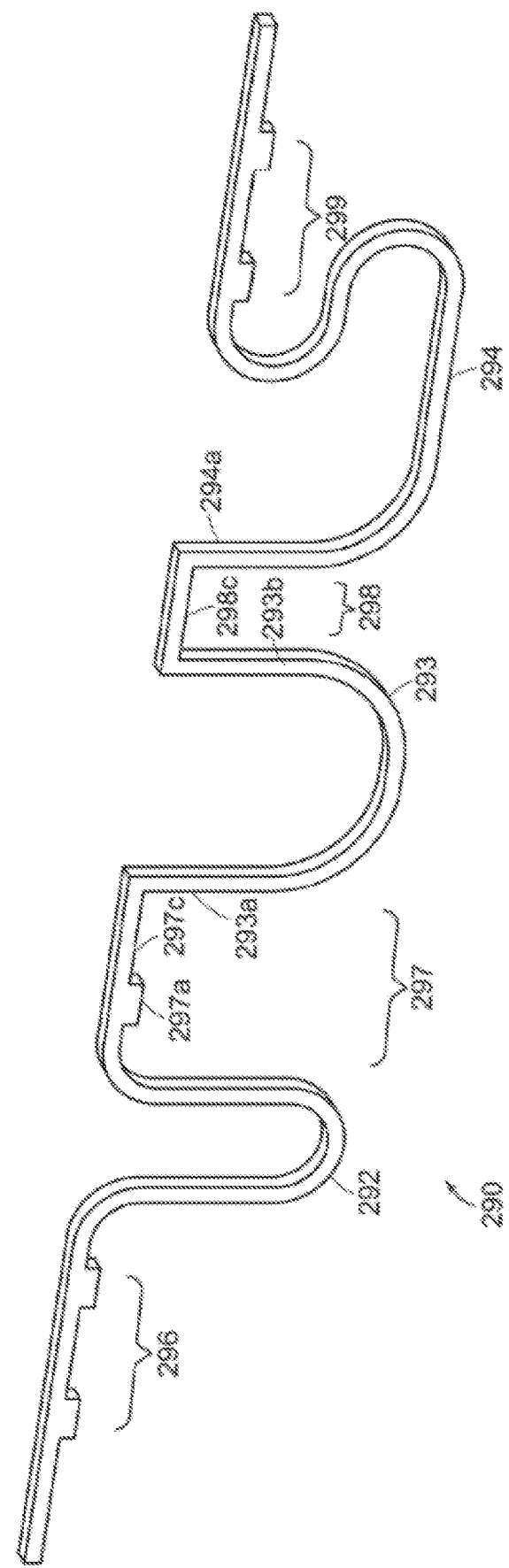
FIG. 33 is a diagram of further examples of loop or curved features and bracket connectors of an appliance.
Figure 34:
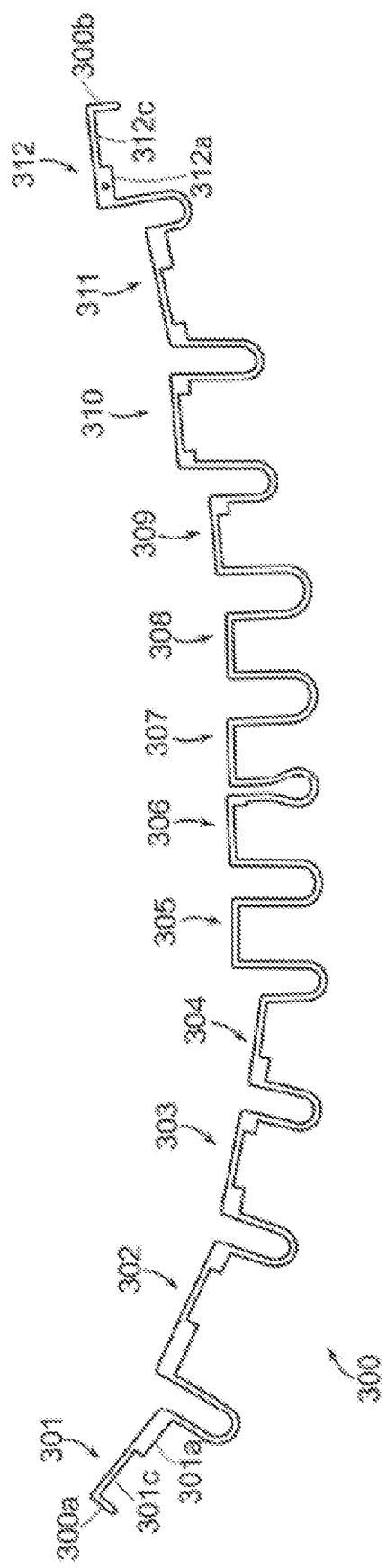
FIG. 34 is a diagram of further examples of loop or curved features and bracket connectors of an appliance

In further examples, such as shown in FIGS. 33 and 34, a bracket connector (or male connector element) may include one or more other features on the rigid bar of the appliance that are configured to inhibit such lateral movement, or that cooperate with one or more extension portions of a bracket connector to inhibit lateral movement of the bracket connector (and the appliance) relative to the bracket 142, when the bracket connector is connected to the bracket 142. For example, in FIG. 33, a rigid bar 290 (which may correspond to the rigid bars 260, 270 or 280 of FIGS. 29-31) has loop or curved features 292, 293 and 294 and a plurality of bracket connectors 296, 297, 298 and 299. In FIG. 33, the bracket connectors 296 and 299 correspond to the bracket connectors 266 and 269 described with regard to FIG. 29.

In FIG. 33, the bracket connector 297 includes a first extension portion 297a, similar to the extension portion 266a described with regard to FIG. 29. The bracket connector 297 also includes a section 297c (corresponding to the section 266c described in FIG. 29) configured to be received in a receptacle 142f of the bracket 142. However, the bracket connector 297 employs an arm section 293a of the loop or curved feature 293 as (or in place of) a second extension portion. In that example, the arm section 293a extends from the section 297c of the bracket connector 297 at a sufficiently large angle (such as, but not limited to 90 degrees) to inhibit lateral movement of the rigid bar 290 relative to a bracket 142, when installed.

In FIG. 33, the bracket connector 298 includes a section 298c (corresponding to the section 266c in FIG. 29) configured to be received in a receptacle 142f of the bracket 142. However, the bracket connector 298 employs an arm section 293b of the loop or curved feature 293 as (or in place of) a first extension portion, and an arm section 294a as (or in place of) a second extension portion. In that example, each of the arm sections 293b and 294a extend from the section 298c of the bracket connector 298 at a sufficiently large angle (such as, but not limited to 90 degrees) to inhibit lateral movement of the rigid bar 290 relative to a bracket 140, when installed. While the examples shown in FIG. 33 include arm sections 293a, 293b and 294a that extend from respective bracket connector sections 297c and 298c at an angle of about 90 degrees, in other examples, the angle may be smaller or greater (such as, but not limited to an angle within the range of about 30-150 degrees).

Figure 35:
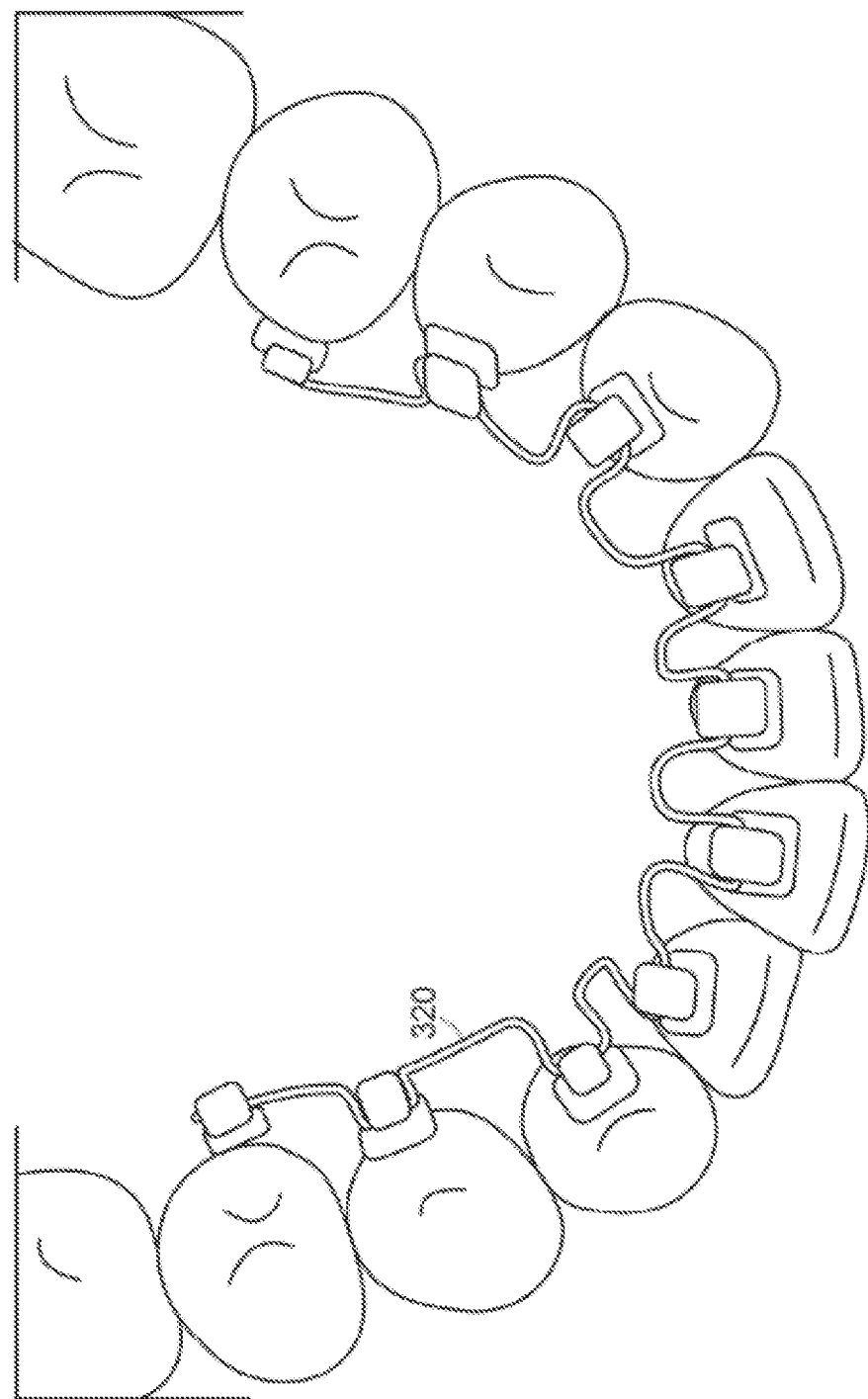
FIG. 35 is a diagram of an appliance having examples of loop or curved features and bracket connectors, installed in a patient's mouth.

FIG. 34 shows a rigid bar 300 having other examples of bracket connectors 301-312 along its length dimension. The rigid bar 300 also includes loop or curved sections, shown between adjacent pairs of bracket connectors. The example bracket connectors in FIG. 34 include bracket connectors 302, 303, 304, 310 and 311 having first and second extension portions and a length section between the extension portions (e.g., corresponding to the first and second extension portions 266a and 266b and the length section 266c of the bracket connector 266 in FIG. 29). However, the extension portions of the bracket connectors 302, 303, 310 and 311 extend all of the way to the leg portion of the adjacent loop or curved section (i.e., extend from the length section between the extension portions to the leg of the adjacent loop or curved section). The example bracket connectors 301 and 312 include a single extension portion (e.g., extension portion 301a or 312a), and a length section (e.g., length section 302c or 312c) extending from the extension portion to a terminal end of the rigid bar 300 (e.g., terminal end 300a or 300b). In the example in FIG. 34, the terminal ends 300a and 300b of the rigid bar 300 include (or are provided in place of) a second extension portion that extends at a sufficiently large angle (such as, but not limited to 90 degrees, or between 30-150 degrees) to inhibit lateral movement of the rigid bar 290 relative to a bracket 140, when installed. The example bracket connectors 305, 306, 307 and 309 in FIG. 34 each have a first extension portion and employ a leg of an adjacent loop or curved feature as (or in place of) a second extension. FIG. 35 shows an example of an appliance 320 having a configuration similar to the appliance 300 (including a rigid bar having loop or curved features and bracket connectors along its length dimension), installed on the teeth of a patient.

While an appliance (or method) having Z embodiment features as described herein may include one or more bracket connectors (or male connector elements) as described with regard to FIGS. 29-35, other examples of appliances (or methods) having Z embodiment features may include other suitable bracket connectors, including, but not limited to annular or ring shape bracket connectors as described with regard to bracket connectors 68, 78, 88 and 98 in FIGS. 6-9D, T shape as described with regard to bracket connectors in FIG. 11, a squeezable configuration as described with regard to the bracket connector in FIG. 15 or 28, other bracket connectors (or male connector elements) described in U.S. patent application Ser. No. 15/370,704, filed Dec. 5, 2016, or yet other suitable bracket connectors (or male connector elements). Also, in any of the example appliance or appliance portions described herein as having Z embodiment features, one or more (or all) of the bracket connectors (or male connector elements) may be replaced by one or more cap connector elements configured to fit over a single tooth (or a plurality of teeth), such as but not limited to the cap connector elements described in U.S. patent application Ser. No. 15/370,704, filed Dec. 5, 2016.

While an appliance (or method) having Z embodiment features as described herein may include one or more loop or curved features as described with regard to FIGS. 29-35, other examples of appliances (or methods) having Z embodiment features may include other suitable curved or loop features, including, but not limited to examples described with regard to FIGS. 36-38. In particular, FIGS. 36 and 37 show certain examples of Z embodiment features, including a rigid bar (330 in FIGS. 36 and 340 in FIG. 37) having loop or curved features (331-338 in FIGS. 36 and 341-348 in FIG. 37) according to various examples, between associated pairs of bracket connectors (or male connector elements).

Each of the loop or curved features 331-338 and 341-348 in FIGS. 36 and 37 includes a pair of linear arm sections coupled by one or more curved sections. For example, the loop or curved feature 331 in FIG. 36 includes first and second linear arm sections 331a and 331b that extend from the rest of the rigid bar 330 to a curved section 331c. In each of the examples in FIGS. 36 and 37, both of the first and second arm sections of the loop or curved feature is larger (e.g., wider) in at least one dimension than the corresponding dimension of the curved section of that feature. For example, each of the linear arm sections 331a and 331b of the loop or curved feature 331 in FIG. 36 has a larger (e.g., wider) dimension than the corresponding dimension (width) of the curved section 331c of that feature 331.

In other examples, one, but not both of the first and second arm sections of any of the loop or curved features 331-338 or 341-348 may be formed larger (e.g., wider) in at least one dimension than the corresponding dimension of the curved section. In other examples, the curved section of any of the features 331-338 or 341-348 may be formed to be larger (e.g., wider) in at least one dimension than the corresponding dimension of one or both of the arm sections. This can allow the appliance to apply a force closer to the center of resistance of the tooth (or any desired location along the length of the tooth, based on the location of the larger or wider section). In yet other examples, the first and second linear arm sections and the curved section of any of the features 331-338 or 341-348 may be formed to have a uniform or constant corresponding dimension (e.g., width).

The loop or curved feature 331 includes a curved section 331c having a generally U shaped portion 331d (an inverted U in the orientation of FIG. 36), and two laterally extended curved loop portions 331e and 331f (located on the two respective sides of the U shaped portion 331d). The U shaped portion 331d extends along and between the first and second arm sections 331a and 331b. The curved loop portion 331e connects one end of the U shaped portion 331d to the first arm section 331a, while the curved loop portion 331f connects the other end of the U shaped portion 331d to the second arm section 331b. Each of the curved loop portions 331e and 331f has a rounded closed end that is wider (in the horizontal dimension of FIG. 36) than the rest of the curved loop portion of the feature 331. The wider, rounded end (331e' and 331f) can provide increased flexibility while decreasing risk of fracture.

The loop or curved feature 332 has a configuration that is similar to the configuration described with regard to feature 331. For example, the loop or curved feature 332 may include first and second linear arm sections 332a and 332b, and a curved section 332c having a U shaped portion 332d and curved loop portions 332e and 332f (corresponding to sections 331a, 331b and 332c and portions 331d, 331e and 331f of feature 331). However, the U shaped portion 332d of the loop or curved feature 332 is smaller than the U shaped portion 331d of the loop or curved feature 331. In the examples in FIG. 36, the U shaped portion 331d extends along about seventy-five percent of the length of the first and second arm sections 331a and 331b, while the U shaped portion 332d extends along about twenty-five percent of the length of the first and second arm sections 332e and 332f. In other examples, the U shaped portion 331d or 332d may extend along any suitable portion of the length of the first and second arm sections. A longer U shaped portion (such as shown at 331d) may be more flexible than a shorter U shaped portion (such as shown at 332d).

Another example of a loop or curved feature 333 also includes first and second linear arm sections 333a and 333b and a curved section 333c (for example, corresponding to the arm sections 331a and 331b and curved section 331c of the feature 331). However, the linear arm sections 333a and 333b are smaller in length than the linear arm sections 331a and 331b of feature 331. The linear arm sections of any of the loop or curved features 331-338 or 341-348 may be of any suitable length (or have different lengths for first and second arm sections). The length of the linear arm section of a loop or curved feature can at least partially determine an amount of force applied to adjacent teeth.

The curved section 333c of the loop or curved feature 333 has a generally U shaped portion 333d (an inverted U in the orientation of FIG. 36), and two laterally extended curved loop portions 333e and 333f (located on the two respective sides of the U shaped portion 333d). However, the generally U shaped portion 333d has an enlarged section 333d' adjacent where the curved loop portions 333e and 333f connect to the generally U shaped portion 333d. The enlarged section 333d' is larger (e.g., wider) in at least one dimension (the horizontal dimension in the orientation of FIG. 36) than the rest of the generally U shaped portion 333d. The curved loop portions 333e and 333f correspond, generally to the curved loop portions 331e and 331f of feature 331. However, the curved loop portion 333e does not extend laterally beyond the left side of the first arm section 333a, and the curved loop portion 333f does not extend laterally beyond (or as far beyond) the right side of the second arm section 333b, relative to lateral extension of the curved or loop portions 331e and 331f. The narrower profile provided by the curved loop portions 333e and 333f (relative to the curved or loop portions 331e or 331f) can be beneficial in contexts in which bracket connectors are closer together (for example, for anterior teeth or other contexts in which space in the mesiodistal dimension or lateral width dimension is limited).

Another example of a loop or curved feature 335 also includes first and second linear arm sections 335a and 335b and a curved section 335c. The linear arm sections 335a and 335b are similar to the linear arm sections 333a and 333b of the feature 333. However, the curved section 335c has a C shape or an open circle shaped portion 335d (having a shape of a circle with an open edge), instead of a U shape described for feature 333. The curved section 335c also has two laterally extended curved loop portions 335e and 335f (corresponding to curved loop portions 333e and 333f of feature 333) located on the two respective sides of the C shape portion 335d.

Another example of a loop or curved feature 334 also includes first and second linear arm sections 334a and 334b and a curved section 334c. The linear arm sections 334a and 334b are similar to the linear arm sections 333a and 333b of the feature 333. However, the curved section 334c has a C shape or an open circle shape (shape of a circle, with an open edge). The radius of the circle shape of the curved section 334c may be selected to provide a desired performance characteristic. For example, each of the loop or curved features 336, 337 and 338 has a shape and configuration similar to that of the loop or curved feature 334, but with a circle shape having a different diameter. More specifically, the loop or curved feature 336 includes first and second linear arm sections 336a and 336b and a curved section 336c that has a smaller diameter than the curved section 334c of feature 334. Similarly, the loop or curved feature 337 includes first and second linear arm sections 337a and 337b and a curved section 337c that has a smaller diameter than the curved section 336c of feature 336. Similarly, the loop or curved feature 338 includes first and second linear arm sections 338a and 338b and a curved section 338c that has a smaller diameter than the curved section 337c of feature 337. A smaller diameter may be beneficial in certain contexts, for example, for certain types of teeth or where space in the lateral width dimension is limited.

Another example of a loop or curved feature 341 in FIG. 37 has a configuration having some similarities to the configuration of the loop or curved feature 331 in FIG. 36. In particular, the loop or curved feature 341 includes first and second linear arm sections 341a and 341b and a curved section 341c. The linear arm sections 341a and 341b are similar to the linear arm sections 331a and 331b of the feature 331. Also, the curved section 341c has a generally U shaped portion 341d (similar to the generally U shaped portion 331d of feature 331). However, the curved section 341c of the feature 340 has two laterally extended curved loop portions 341e and 341f that each have a C shape or an open circle shape (shape of a circle, with an open edge), instead of a curved loop shape of feature 331. The loop or curved feature 348 has a similar configuration as the loop or curved feature 341.

Another example of a loop or curved feature 345 in FIG. 37 has a configuration having some similarities to the configuration of the loop or curved feature 331 in FIG. 36. In particular, the loop or curved feature 345 includes first and second linear arm sections 345a and 345b and a curved section 345c. The linear arm sections 345a and 345b are similar to the linear arm sections 331a and 331b of the feature 331. Also, the curved section 345c has a generally U shaped portion 345d (corresponding to the generally U shaped portion 331d of feature 331). However, the generally U shaped portion 345d has an enlarged section 345d' at the closed end of the U shaped portion 345d, and a second enlarged section 345d" where curved loop portions 345e and 345f connect to the generally U shaped portion 345d. The enlarged sections 345d' and 345d" are each larger (e.g., wider) in at least one dimension (the horizontal dimension in the orientation of FIG. 37) than other sections of the generally U shaped portion 345d. The curved loop portions 345e and 345f correspond, generally to the curved loop portions 331e and 331f of feature 331.

Another example of a loop or curved feature 346 in FIG. 37 has a configuration corresponding to the configuration of feature 345 (including first and second arm sections 346a, 346b and a curved section 346c having a generally U shaped portion 346d similar to corresponding parts of the feature 345). However, the loop or curved feature 346 has curved loop portions 346e and 346f that correspond in shape to the curved loop portions 341e and 341f of feature 341.

Another example of a loop or curved feature 347 in FIG. 37 has a configuration corresponding to the configuration of feature 341 (including first and second arm sections 347a, 347b and a curved section 347c having curved loop portions 347e and 347f that correspond in shape to the curved loop portions 341e and 341f of feature 341). However, the curved section 347c of the loop or curved feature 347 has a C shape or an open circle shaped portion 347d (having a shape of a circle with an open edge), instead of a generally U shape described for feature 341d.

Other examples of loop or curved features 342, 343 and 344 in FIG. 37 also include first and second linear arm sections and a curved section. The curved sections of each of the loop or curved features 342, 343 and 344 include various combinations of generally U shaped portions and C or open circle shaped portions, configured to provide a desired flexibility, a bias or spring force in one or more directions (or both), a force magnitude, durability, or other characteristics.

In particular examples, the configuration of one or more (or each) of the loop or curved features on any of the example appliance (or method) described herein may be selected and designed to provide a desired bias or spring force in one or more directions (or both) and magnitude, for moving one or more teeth in a patient's jaw. For example, in FIG. 38, a rigid bar 350 includes a loop or curved feature 351 (which may correspond to the rigid bar 340 and the loop or curved feature 341 described with regard to FIG. 37). The rigid bar 350 also includes bracket connectors 352 and 354, for selectively connecting to brackets (not shown) that are secured to the teeth 356 and 357, respectively, as described herein. In certain examples, the loop or curved feature 351 may be configured to provide a force on one or both teeth 356 and 357 (when the bracket connectors 352 and 354 are connected to respective brackets on the teeth 356 and 357), where the force on each tooth is directed toward the adjacent tooth. In one example, the tooth 356 may be a canine tooth, while the tooth 357 may be a second pre-molar. In other examples, the teeth 356 and 357 may be other teeth in a patient's jaw (upper jaw or lower jaw).

In particular examples, the loop or curved feature 351 is configured to apply the force on one or both teeth 356 and 357, at a location along the length dimension of each tooth corresponding to a center of resistance location. In the drawing if FIG. 38, the teeth 356 and 357 are shown laterally adjacent to the bracket connectors 352 and 354. However, it will be understood that, when the bracket connectors 352 and 354 are connected to brackets on the respective teeth 356 and 357, each of the bracket connectors 352 and 354 will be placed on or directly adjacent to a surface of a respective tooth 356 and 357 on which a bracket (not shown in FIG. 38) is secured, as described herein.

In the example in FIG. 38, the loop or curved feature 351 is configured such that (when the bracket connectors 352 and 354 are connected to respective teeth 356 and 357) the loop or curved feature 351 imparts a force F1 on the tooth 356 in a direction toward the tooth 357, and also imparts a force F2 on the tooth 357 in a direction toward the tooth 356. The magnitude of each force F1 and F2 depend on one or more (or a combination of) the shape and configuration of the loop or curved feature 351, the lateral spacing between the bracket connectors 352 and 354, and the thickness and material of the loop or curved feature 351.

In the example in FIG. 38, the loop or curved feature 351 includes linear arm sections 351a and 351b that have a selected length dimension. The length of the linear arm sections 351a and 351b may be selected to locate one or more curved sections 351c of the loop or curved feature 351 adjacent (or relatively close to) the location (along the arch or horizontal dimension of the jaw) of the centers of resistance 356a and 357a of the respective teeth 356 and 357.

In that manner, the loop or curved feature 351 (or the one or more curved sections 351c) may be located at or near an alignment with the centers of resistance 356a and 357a of the respective teeth 356 and 357 (to impart the force F1 or F2 on the tooth 356 or 357, at or near the center of resistance 356a or 357a of the tooth 356 or 357, for example, along an imaginary dimension line that extends from one center of resistance 356a to the other center of resistance 357a). In other examples, the loop or curved feature 351 (or the one or more curved sections 351c) may be configured to impart a force F1 or F2 on a tooth 356 or 357, at a location that is spaced apart (e.g., vertically offset in the orientation of FIG. 38) from the center of resistance 356a or 357a (or from the imaginary dimension line), by a specified distance. In such other examples, the force F1 or F2 can have a lever-like action on a tooth 356 or 357, where the center of resistance acts as a fulcrum. In particular examples described herein, an appliance (or method) may include one or more loop or curved features that are configured to impart one or more forces on one or more teeth, where the direction, and magnitude of the force or forces may be selected, and the location of the force (relative to a center of resistance of one or more of the teeth) may be selected based, in part, on the configuration of the loop or curved feature, the lengths of the arm sections of the loop or curved feature, and the width or thickness dimension and material of the loop or curved feature).

Any of the example appliances or appliance portions (including rigid bars, bracket connectors, and loop or curved features) having Z embodiment features as described in any of the examples of FIGS. 29-38 may be made of any suitable material or materials, such as, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in single structure. However, in particular examples, the rigid bars, bracket connectors and loop or curved features of an appliance (or portion of an appliance) described in those examples are made by cutting a two dimensional (2D) form of the appliance from a 2D sheet of material and bending the 2D form into a desired 3D shape of the appliance, according to processes as described in U.S. patent application Ser. No. 15/370,704, filed Dec. 5, 2016 or other suitable processes.

Figure 39:
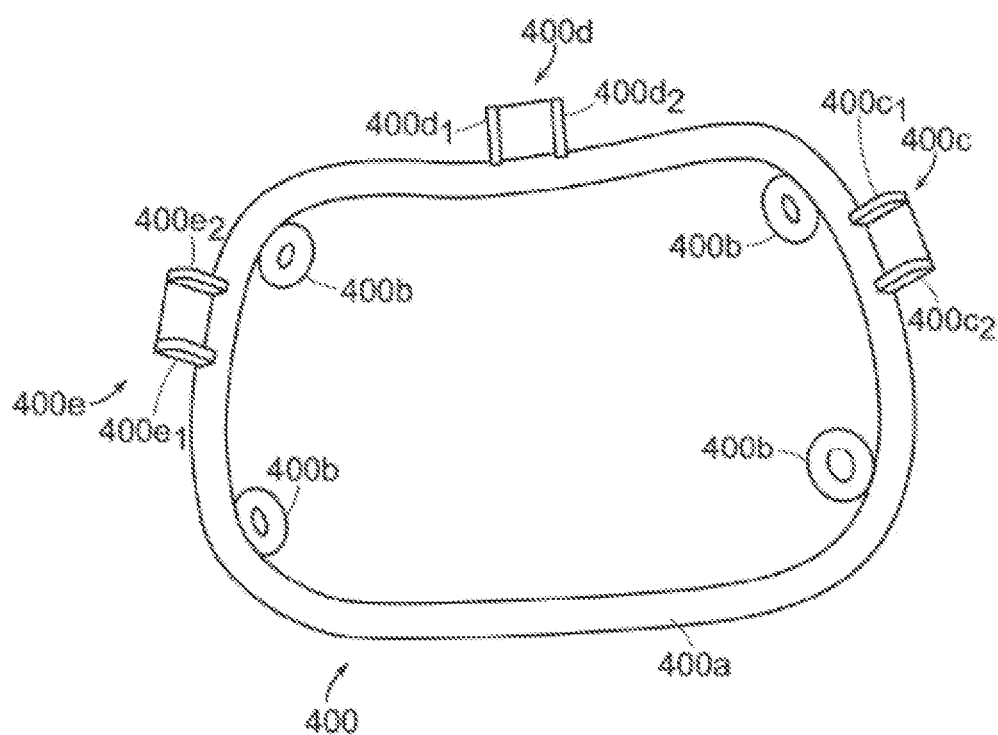
FIG. 39 is a perspective view of a platform for an appliance.
Figure 40:
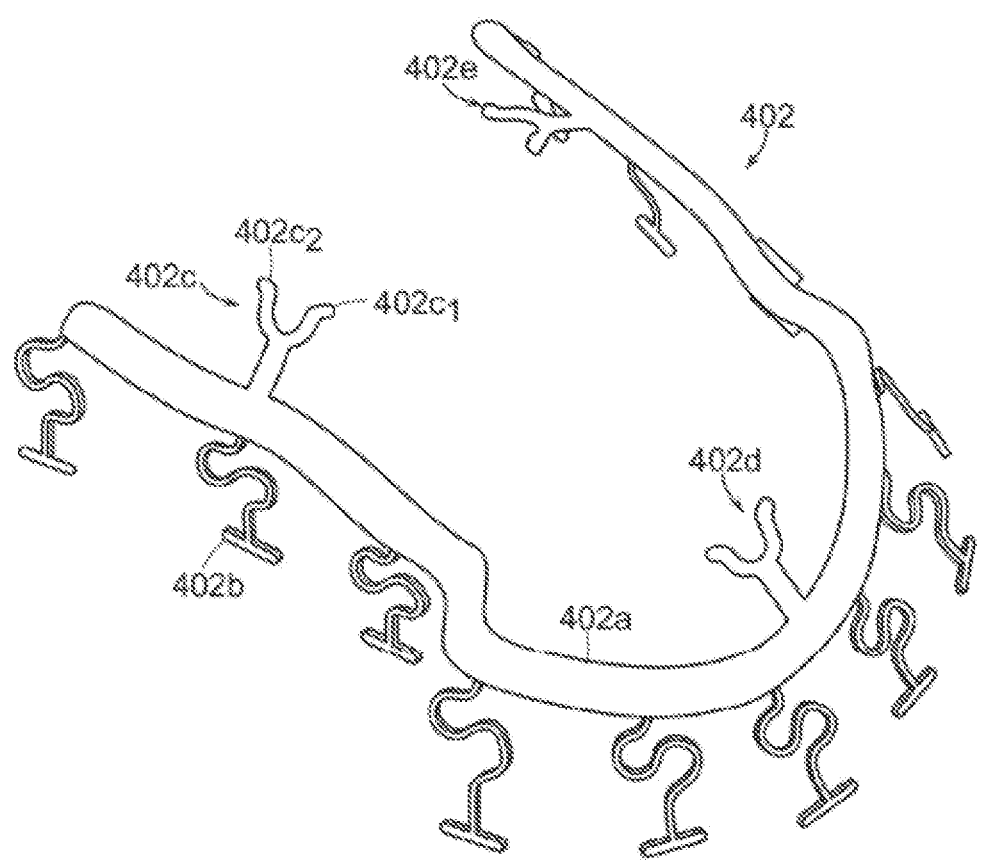
FIG. 40 is a perspective view of an appliance configured to connect with the platform of FIG. 39.

Any of the example appliances described herein (or other suitable appliances) may include or connect with an anchoring platform, for engaging or securing the appliance to a maxilla or a mandible bone of a patient. Examples of anchoring platforms are shown and described with regard to FIGS. 39-42, 63 and 64. In FIG. 39, a platform 400 for securing to a palate or maxilla bone of a patient is shown, detached from a rigid bar of an appliance. In FIG. 40, an appliance 402 includes platform connection arms 402a, 402b and 402c, to be selectively connected with an anchoring platform (such as platform 400). Further examples of anchoring platforms having various different platform configurations are shown in FIGS. 41A-41E, represented as being secured to a patent's maxilla or mandible.

The platform 400 in FIG. 39 has an annular body 400a, one or more (or a plurality of) anchorage device connector elements 400b, and one or more (or a plurality of) appliance connector elements 400c, 400d and 400e. The example in FIG. 39 includes four anchorage device connector elements 400b and three appliance connector elements 400c, 400d and 400e. In other examples, the platform may include more or fewer anchorage device connector elements, or more or fewer appliance connector elements than shown in FIG. 39. In other examples, the platform body 400a may have other suitable shapes and configurations, including but not limited to plate-shaped or cup-shaped configurations that are not annular.

In the example in FIG. 39, each of the anchorage device connector elements 400b extend from the annular body 400a, toward the center of (or inward from) the annular shape. Also in the example in FIG. 39, each of the appliance connector elements 400c, 400d and 400e extend from the annular body 400a, in a direction away from the center of (or outward from) the annular shape. In other examples, some or all of the anchorage device connector elements 400b may extend outward, or one or more of the appliance connector elements 400c, 400d and 400e may extend inward, relative to the annular shape of the body 400a.

Each of the anchorage device connector elements 400b is configured to hold a permanent anchorage device or a temporary anchorage device (TAD). In certain examples, the anchorage device connector elements 400b may correspond to the TAD holders described in U.S. patent application Ser. No. 15/370,704, filed Dec. 5, 2016 (for example, at reference numbers 812, 904 or 1012 in that application). The anchorage device connector elements 400b allow a clinician to secure the annular body 400a of the platform to a patient's palate using one or more anchoring devices such as, but not limited to screws, temporary anchorage devices TADs or other suitable anchorage device that extend into the patient's palate (soft and hard tissue). In certain examples, each anchorage device connector element 400b may have an opening (e.g., an opening in an annular extension) through which a screw, TAD or other anchor device may extend. In other examples, other suitable anchorage device connector element configurations may be employed for receiving or holding a screw, TAD or other anchor device.

Each of the appliance connector elements 400c, 400d and 400e is configured to be selectively connected with a respective platform connection arm on an appliance (such as the appliance 402 in FIG. 40). Each appliance connector element 400c, 400d and 400e may have a configuration corresponding to any of the brackets (or female connector elements) described herein or in U.S. patent application Ser. No. 15/370,704, filed Dec. 5, 2016. Each platform connection arm 402 may have a configuration corresponding to any of the bracket connectors (or male connector elements) described herein or in U.S. patent application Ser. No. 15/370,704, filed Dec. 5, 2016. In other examples, each appliance connector element and each platform connection arm may have any other suitable configuration for selectively connecting and disconnecting from each other. In certain examples, each appliance connector element 400c, 400d and 400e has a configuration that includes a receptacle for receiving and holding a portion of respective platform connection arm of an appliance.

In FIG. 40, an appliance 402 includes a rigid bar 402a and a plurality of arms 402b (for example, in accordance with certain X embodiment features as described herein). The appliance 402 also includes a plurality of platform connector arms 402c, 402d and 402e. In other examples, similar platform connector arms may extend from a rigid bar or rigid bar section of any of the other example appliances, appliance members (or methods) described herein.

Each of the platform connector arms 402c, 402d and 402e has a connector element at its distal end, for selectively connecting to a respective appliance connector element 400c, 400d or 400e of a platform. In certain examples, each connector element (on the arms 402c, 402d and 402e) is configured to be selectively connectable (from a disconnected state) and selectively disconnectable (from a connected state) to a respective one of the appliance connector element 400c, 400d or 400e (on the platform).

In the example in FIG. 40, the connector element at the distal end of each connector arm 402c, 402d or 402e has a Y shape, with each finger of the Y having a laterally projecting end portion (represented as 402c1 and 402c2 on the connector arm 402c) that is configured to be received within a corresponding aperture in one of the appliance connector element 400c, 400d or 400e, to connect the connector element to the appliance connector element. More specifically, the Y shaped arm 402c, 402d and 402e may be made of sufficiently resilient material to allow the fingers of the Y shape to be squeezed together (such as by a dental tool) to allow the fingers of the Y shape to be placed between projecting segments (represented by 400c1 and 400c2 of the appliance connector element 400c in FIG. 39), with the laterally projecting end portion (e.g., 402c1 and 402c2) aligned with receptacles (apertures or indentations) in the appliance connector element (e.g., in the projecting segment 400c1 and 400c2). Once the fingers of the Y shape are squeezed together and placed between the projecting segments of the appliance connector, the fingers may be released to allow the Y shaped arm to resiliently expand back to shape (under its natural spring force). As the Y shaped arm expands back to shape, the laterally projecting end portion (e.g., 402c1 and 402c2) are received within (extend into) the receptacles (apertures or indentations) in the appliance connector element, to secure the Y shaped arm to the platform. In other examples, the connector elements and appliance connector elements may have other suitable shapes and configurations for selective connection (and, in certain examples, for selective dis-connection from a connected state).

Figure 41B:
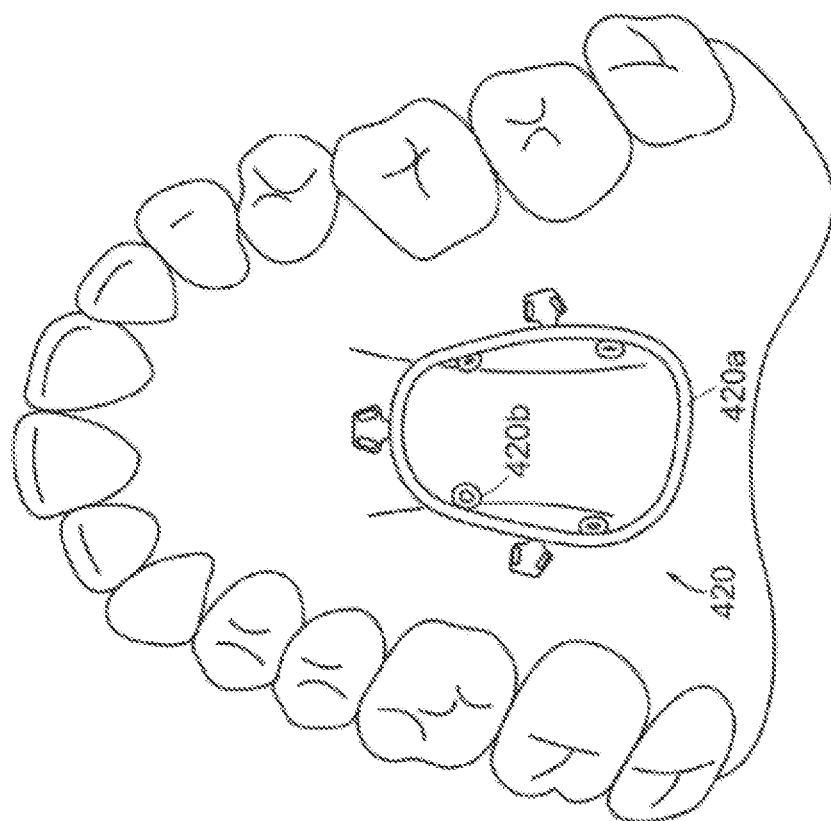
FIGS. 41A and 41B are perspective views of anchoring platforms, represented as being placed on a patient's palate.
Figure 41A:
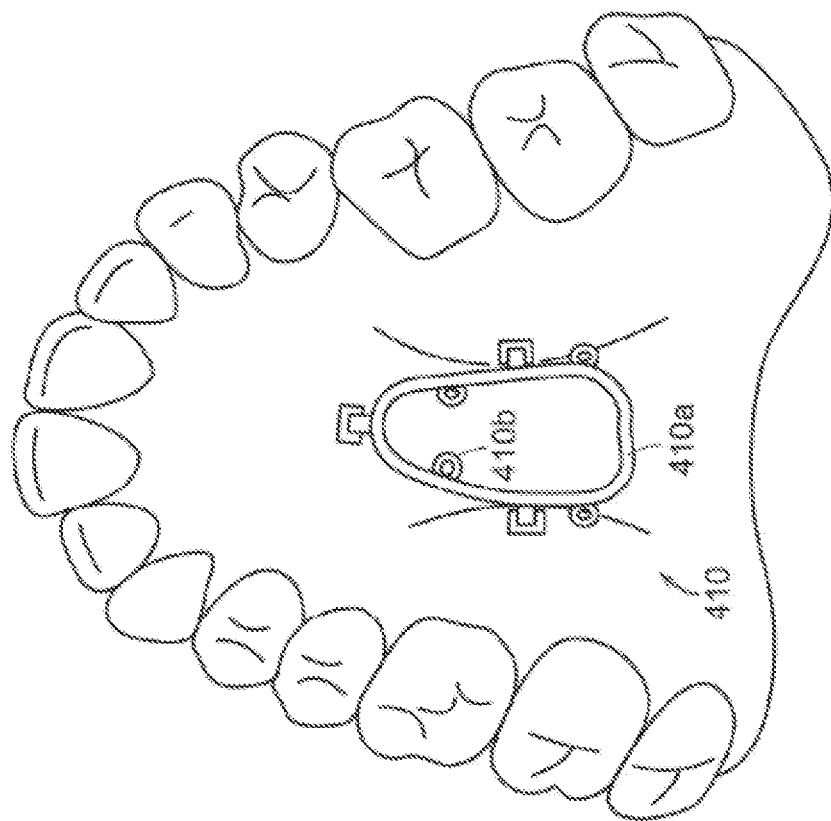

A further example of a platform 410, represented as being secured to a patient's maxilla, is shown in FIG. 41A as having an annular body 410a configured similar to the platform 400. The platform 410 in FIG. 41A includes a plurality of anchorage device connector elements 410b (e.g., similar to the anchorage connector elements 400b described above). However, on the platform 410, two of the anchorage device connector elements 410b extend inward from the annular body 410a, toward the center of the annular body, and two of the anchorage device connector elements 410b extend outward from the annular body 410a.

Another example of a platform 420, represented as being secured to a patient's maxilla, is shown in FIG. 41b as having an annular body 420a configured similar to the platforms 400 and 410. The platform 420 in FIG. 41B includes a plurality of anchorage device connector elements 420b, each of which extend inward toward the center of the annular body (e.g., similar to the anchorage connector elements 400b described above).

Figure 41C:
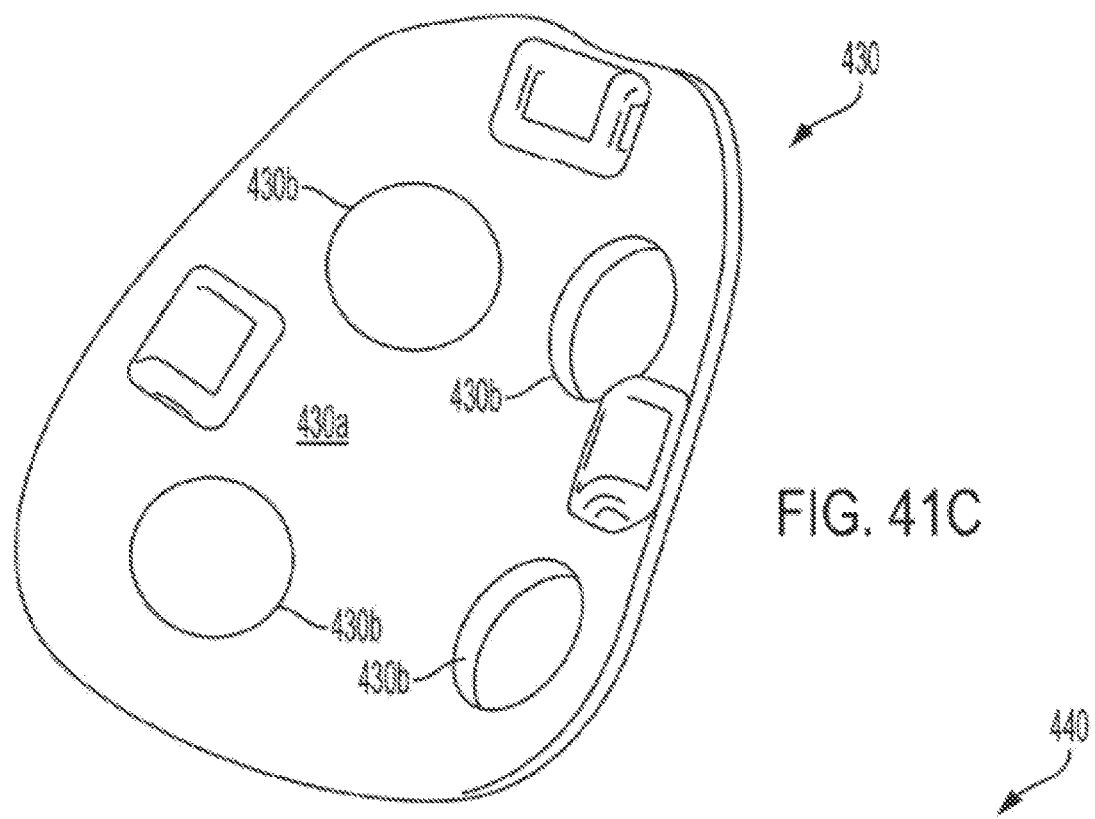
FIGS. 41C and 41D are perspective views of anchoring platforms according to further examples.

Another example of a platform 430 configured to be secured to a patient's maxilla, is shown in FIG. 41C. The platform 430 includes a body 430a having a plate-like shape that is concaved or curved in a shape of a patient's palate. In particular examples, the body 430a is has a surface (e.g., a convex curved surface facing into the page in FIG. 41C) formed to correspond and fit with the palate shape of a particular patient and may be formed from an intraoral scan or an impression mold made from the patient's palate. In other examples, the body 430a may be formed to correspond to and fit with many patient's palates. In some examples, multiple shapes or sizes of the body 430a may be made to fit multiple groups of patients, where each shape or size may fit a defined group of patients. The platform body 430a includes one or more (or a plurality of) openings 430b through which one or more TADs, bolts or other anchoring devices may extend, to secure the platform body to a patient's palate. In the example shown in FIG. 41C, the platform body 430a includes four TAD openings 430b. Other examples may include any other suitable number of TAD openings and locations on the platform body 430a.

The platform 430 includes one or more (or a plurality of) appliance connector elements that extend from the concave surface of the platform body 430. The example in FIG. 41C includes three appliance connector elements 430c, 430d and 430e, which may correspond (in structure and operation) to appliance connector elements 400c, 400d and 400e discussed above. In other examples, the platform 430 may include any suitable number, location and configuration of appliance connector elements. The platform 430 is configured to secure to a patient's palate and be connected with an appliance, similar to the platform 400 discussed above. However, the concave plate-like shape of the platform body 430a can provide additional stability on the patient's palate and comfort.

Figure 41D:
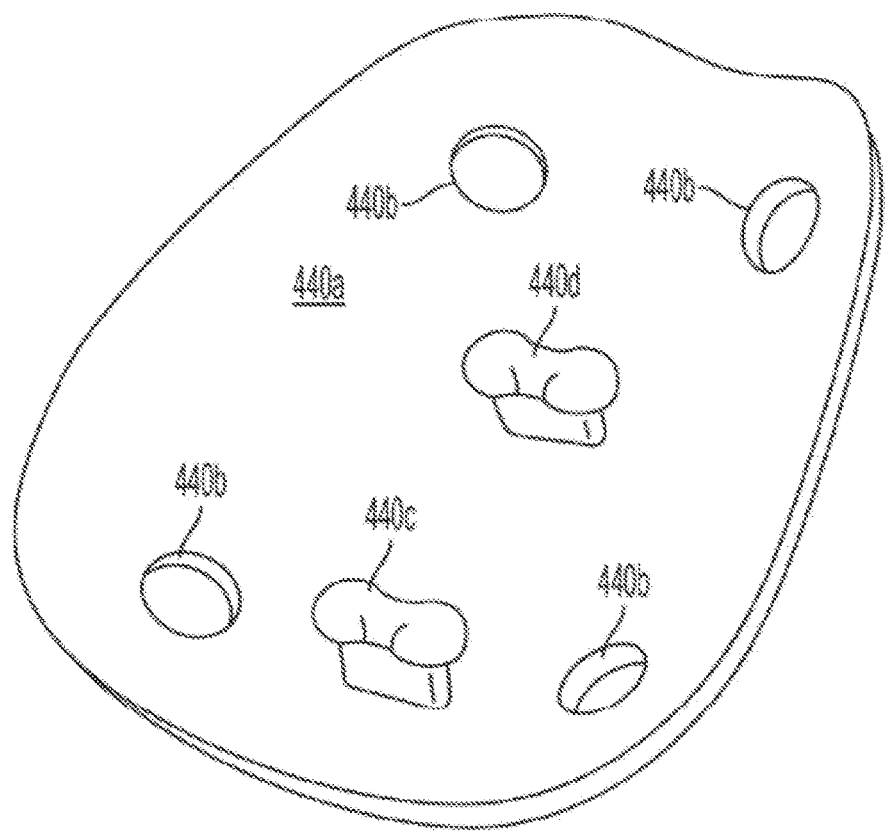

Another example of a platform 440 configured to be secured to a patient's maxilla, is shown in FIG. 41D. The platform 440 includes a body 440a having a concave, plate-like shape, with a plurality of openings 440b (which may be similar to the platform body 430a and openings 430b described above). The platform 440 includes appliance connector elements 440c, 440d extending from a central region of the concave surface of the platform body 440a. Each connector element 440c and 440d is configured to provide a snap fit or friction fit with a corresponding connector element on an appliance (not shown). For example, each appliance connector element 440c and 440d has a free end with a head that has an enlarged width relative to the rest of the appliance connector element (where the head is configured to friction fit or snap fit with a mating shaped receptacle on a platform connection arm of an appliance (not shown). In other examples, each of the appliance connector elements 440c and 440d may be configured to snap together or otherwise connect with an aligner (such as an aligner as described herein or other aligner) having suitable mating receptacles for receiving the appliance connector elements. Other examples may include any other suitable number, location and configurations of appliance connector elements on the platform body 440a.

Figure 41E:
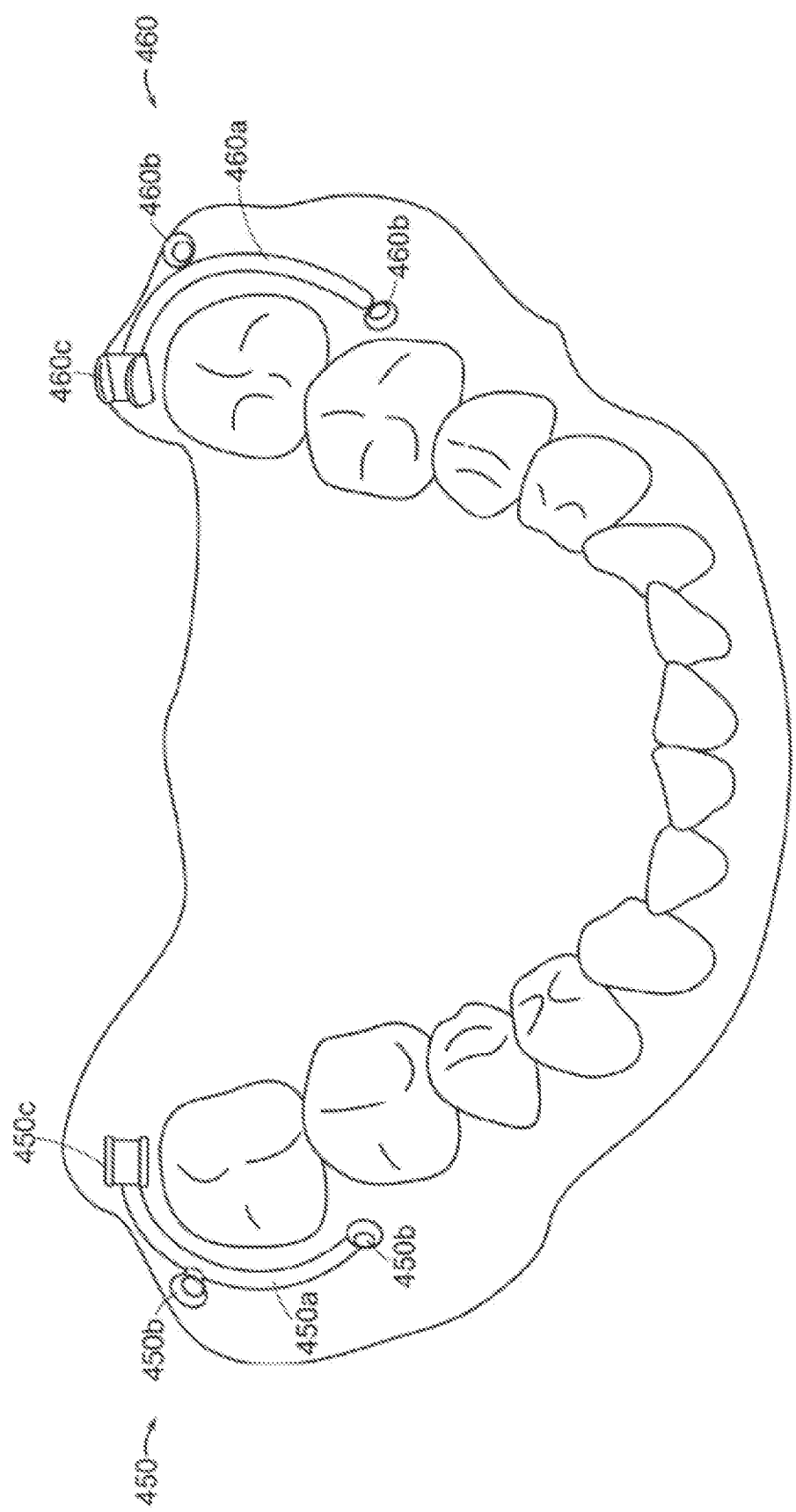
FIG. 41E is a perspective view of an anchoring platform, represented as being placed on a patient's mandible.

In other examples, anchoring platforms are configured to be secured to a patient's mandible. An example of two platforms 450 and 460 is shown in FIG. 41E, represented as secured to a patient's maxilla. Each platform 450 and 460 includes a platform body 450a or 460a, one or more anchorage device connector elements 450b or 460b and one or more appliance connector elements 450c or 460c. In the example in FIG. 41E, each platform 450 and 460 includes one appliance connector element 450b or 460b and two anchorage device connector elements 450c or 460c. The appliance connector elements 450b and 460b may correspond (in configuration and operation) to the appliance connector elements 400c-e discussed above. The anchorage device connector elements 450b and 460b may correspond to the anchorage connector elements 400b discussed above. In other examples, one or both platforms 450 and 460 may include any suitable number, location and configuration of appliance connector elements and anchorage device connector elements.

In the example of FIG. 41E, the platform body 450a or 460a comprises a rigid bar having an arc or curved shape, to correspond to the curvature of a portion of a patient's denture or gingival. In the example in FIG. 41E, each platform body 450a and 460a is configured to curve around a portion of a patient's rear molar, on the lower jaw. In other examples, the platform body 450a or 460a may be shaped to correspond and fit around or adjacent any other suitable portion of the patient's lower jaw, to provide an anchoring location for an appliance at a desired position along the patient's jaw. A platform as shown and described in FIG. 41E may be configured for securing to any suitable location on the patient's mandible, for providing an anchoring position for an appliance. In various examples, platforms may be configured to be secured to the mandible or the maxilla of a patient, in any suitable location, such as, but not limited to the buccal vestibule with TADs between the roots that will not move, buccal shelf in the mandible, plate, zygomatic area, or the like.

Figure 42:
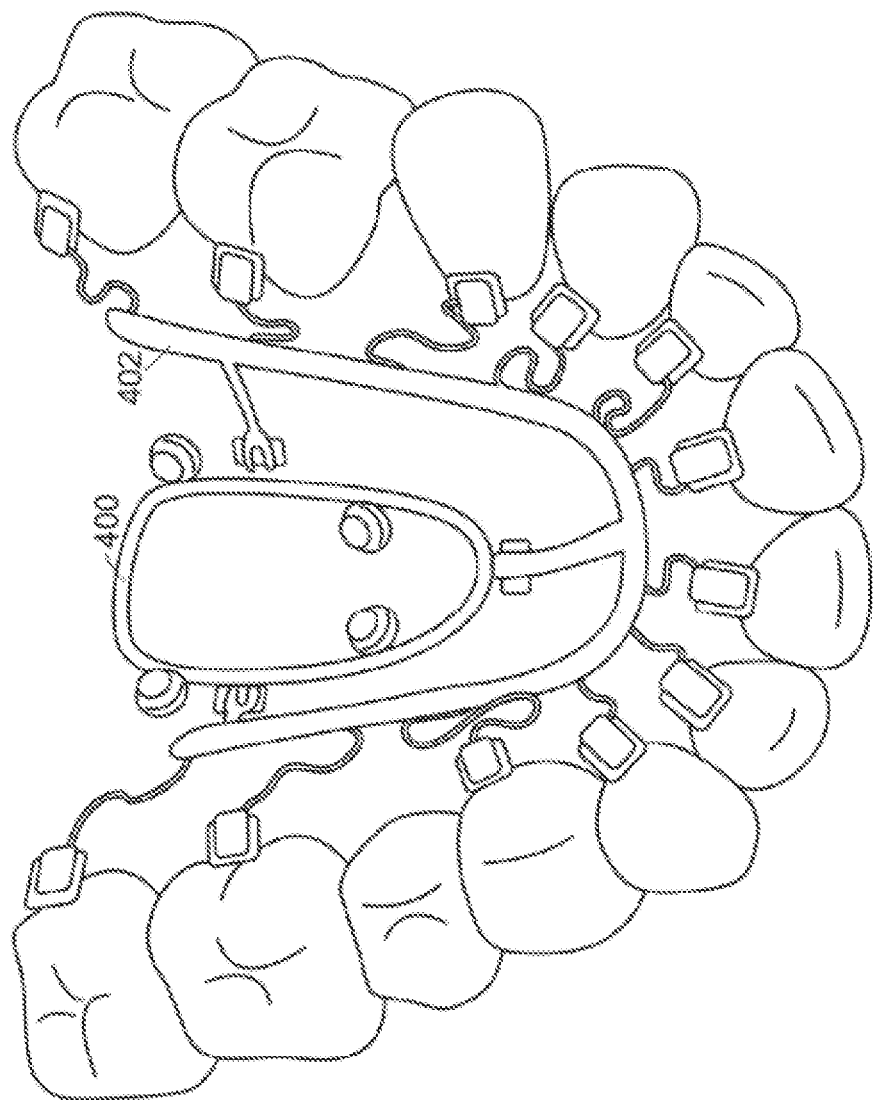
FIG. 42 is a perspective view of the appliance of FIG. 40 connected to the platform of FIG. 39 and installed in a patient's mouth.

In particular examples, a platform as described herein is configured to be installed using anchorage devices and the anchorage device connector elements as described herein. Either before or after installing the platform body on the patient's palate, an appliance (such as, but not limited to the appliance 402 in FIG. 40) is installed on a patient's teeth, as described herein. As part of the installation of the appliance (e.g., the appliance 402 as an example), the connector elements of the platform connector arms (such as, but not limited to the arms 402c, 402d and 402e in FIG. 40) are connected to the appliance connector elements (such as, but not limited to the elements 400c, 400d or 400e of the platform 400, as shown in FIG. 42). In particular examples, an appliance (such as, but not limited to the appliance 402) may be connected with any suitable platform as described herein, to provide additional anchorage and support. In some contexts, the additional anchorage and support can help to move (or more completely move) one or more teeth (or a plurality of teeth independent of each other).

Platforms 400, 410, 420, 430 440, 450, 460 and 6300 (and components of the platforms) as described herein may be made of any suitable material including, but not limited to Nitinol (NiTi), stainless steel, beta-titanium, cobalt chrome or other metal alloy, polymers or ceramics, and may be made as a single, unitarily-formed structure or, alternatively, in multiple separately-formed components connected together in a single structure.

Any of the example appliances described herein (or other suitable appliances) may include or operate with an installation unit, for assisting a clinician or technician to install the appliance. Installation units according to various examples are described with regard to FIGS. 43-49.

Figure 43:
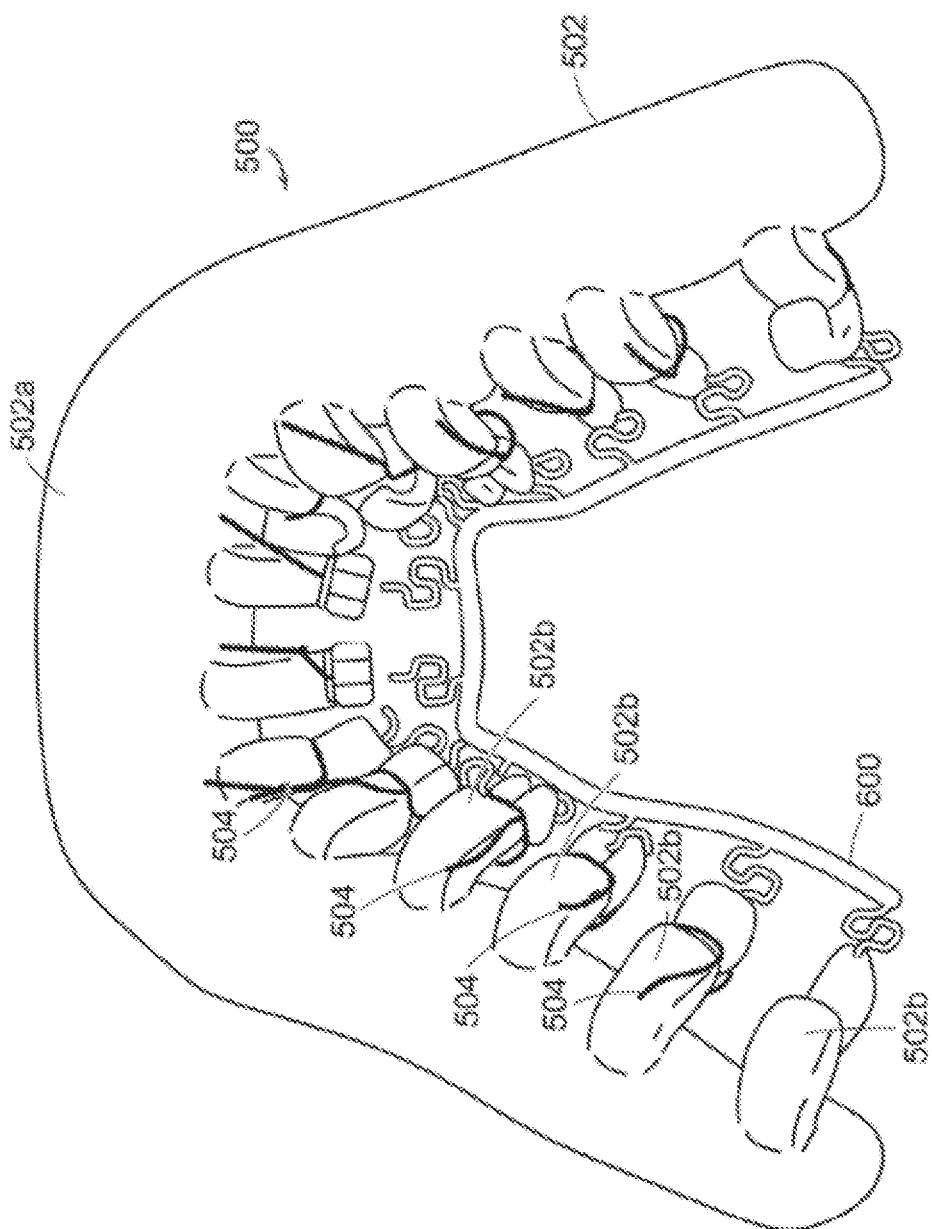
FIGS. 43-49 are each a perspective view of an installation unit and an appliance connected to the installation unit.
Figure 44:
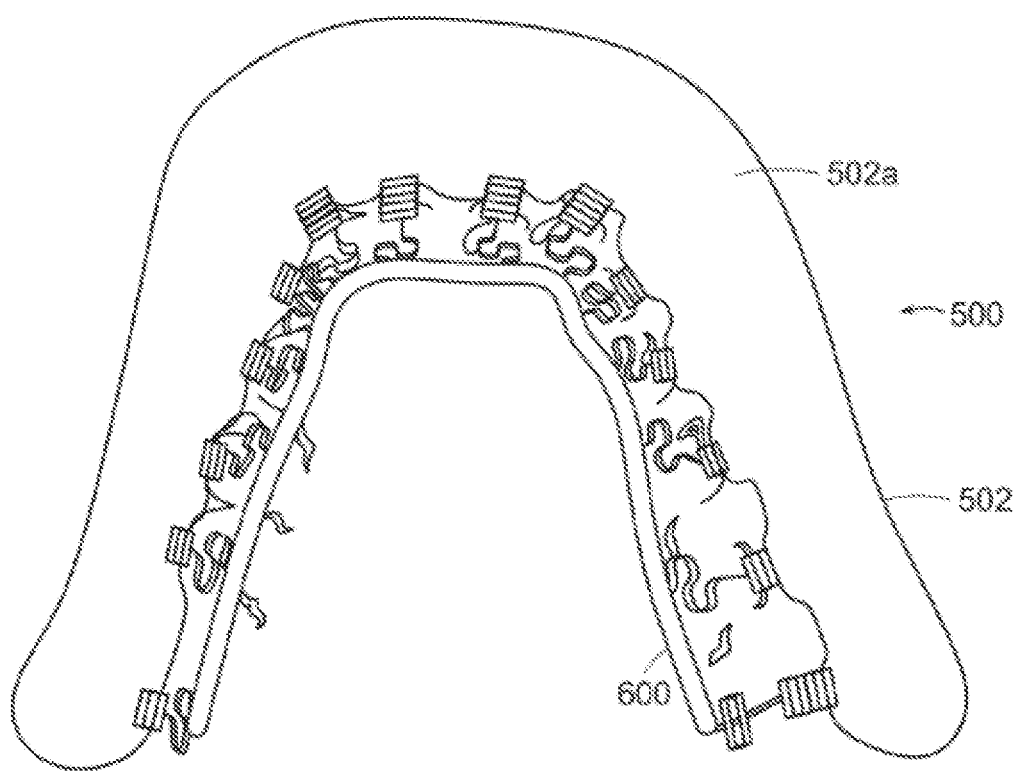
Figure 45:
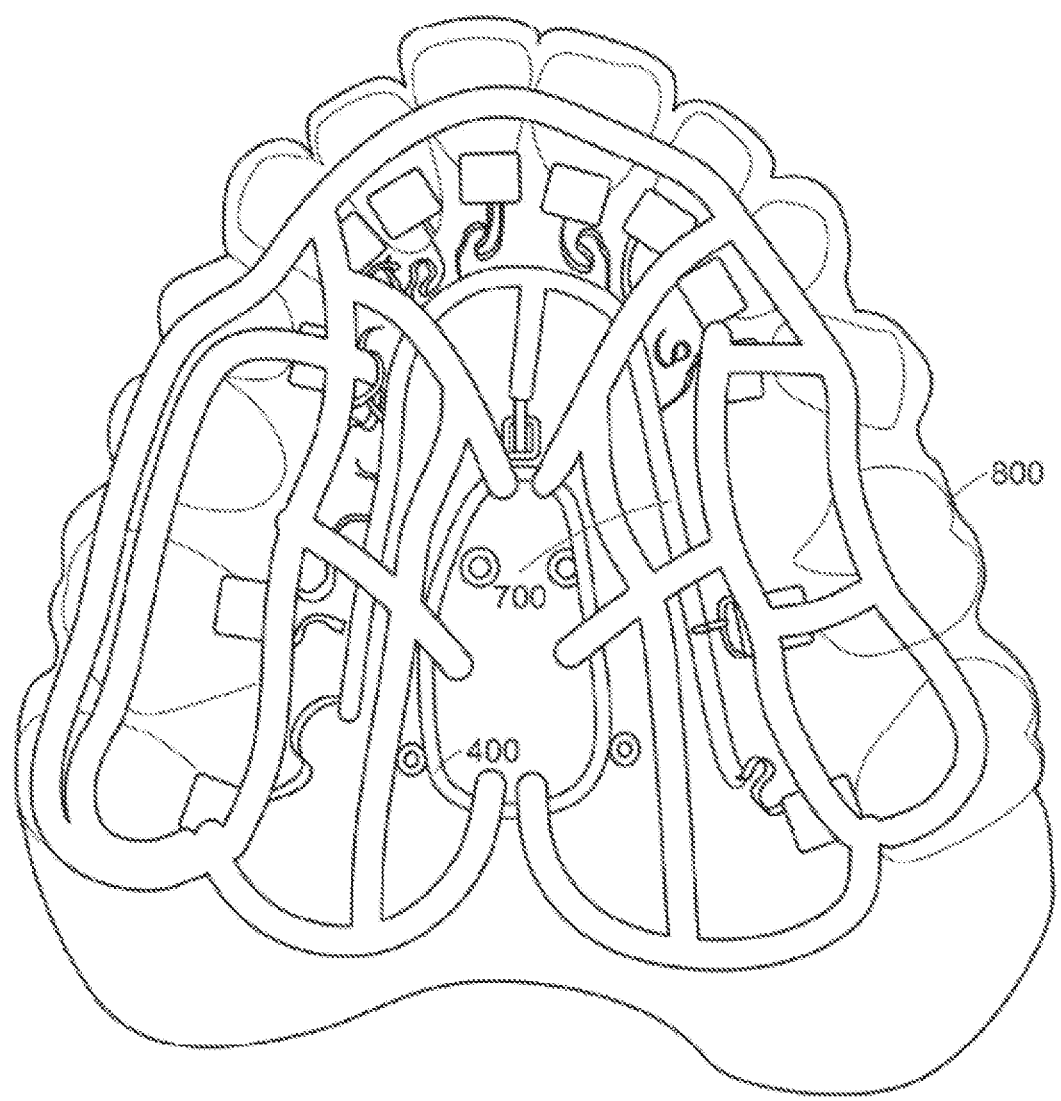
Figure 46:
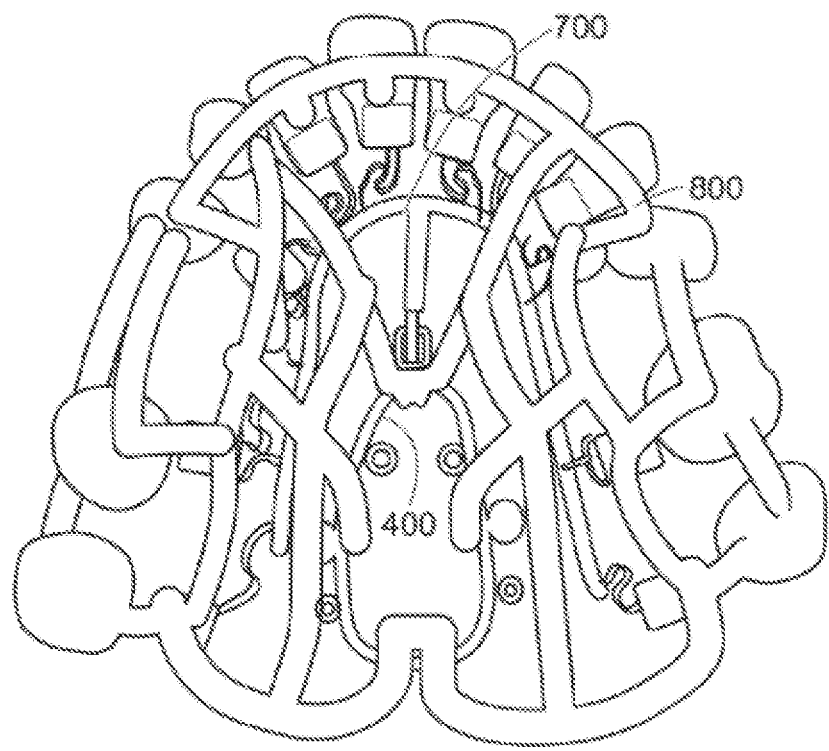
Figure 47:
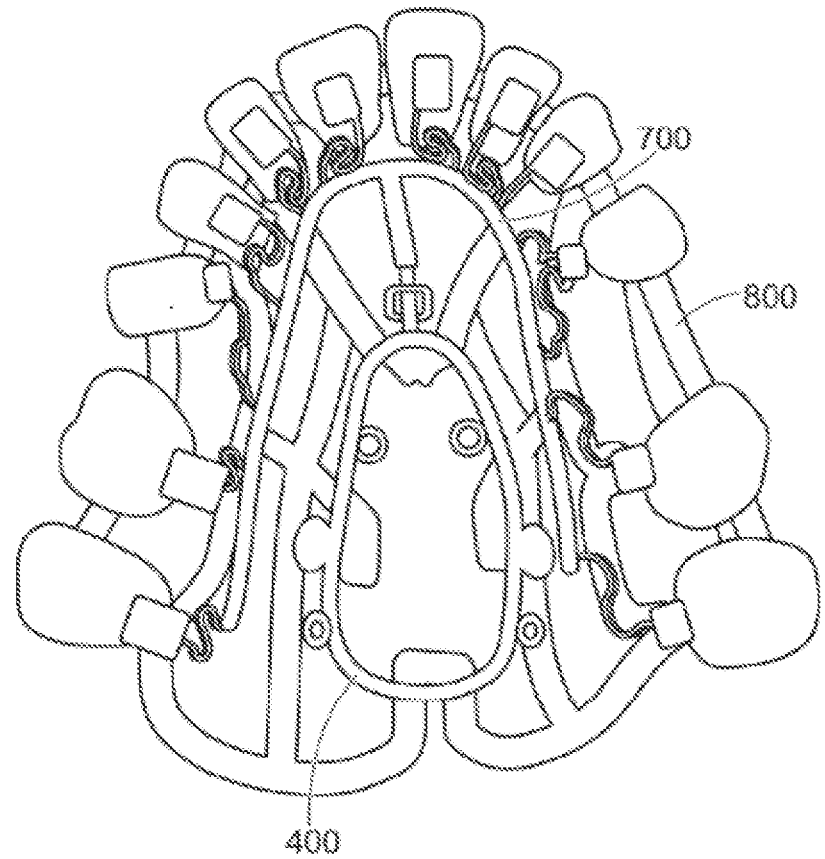
Figure 48:
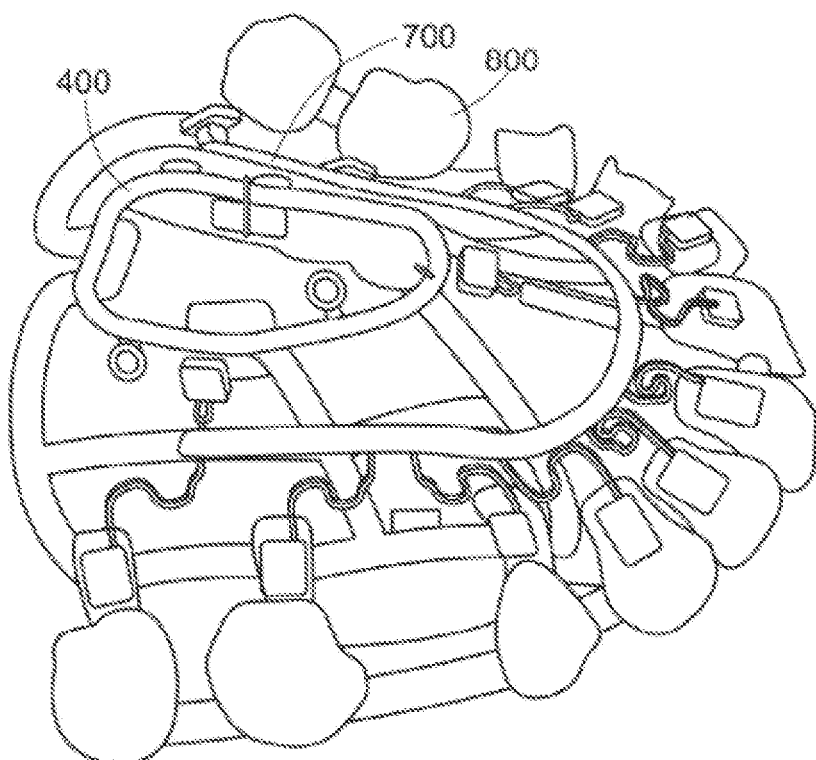
Figure 49:
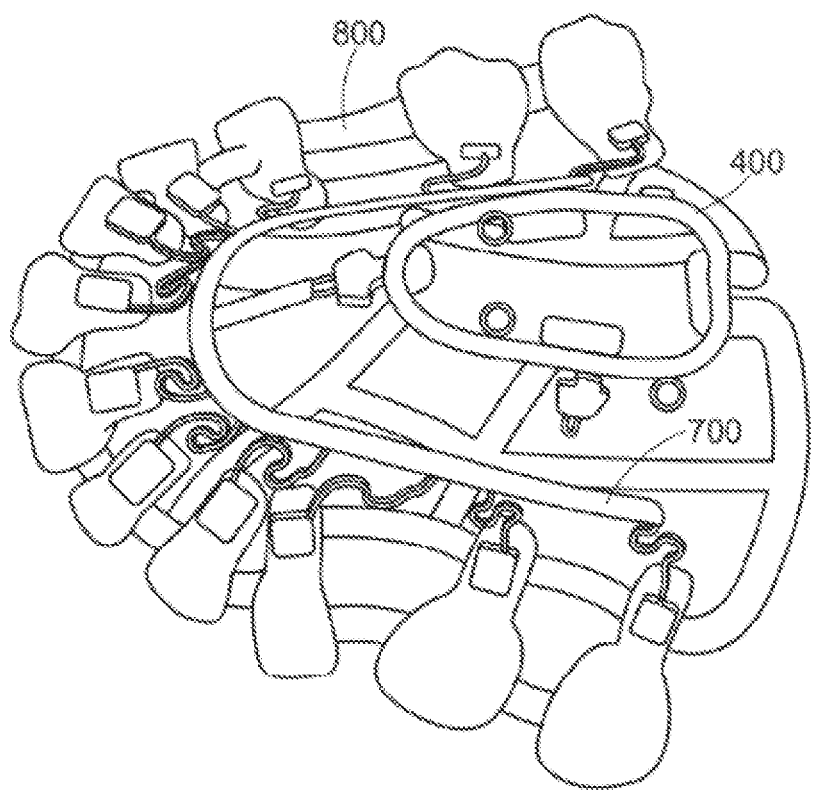

In certain examples, as shown in FIGS. 43 and 44, an installation unit 500 includes a body portion 502 configured to fit onto one or more (or a plurality of) teeth in a patient's jaw (an upper jaw or a lower jaw). In certain examples, the body portion 502 may have a shape that corresponds to the entire set of teeth in one of the patient's jaws. For example, the body portion 502 may have an arch shape (or partial arch shape) of an intraoral scan or a dental impression formed of the patient's jaw. Accordingly, the body portion 502 may include a recess 502a for receiving one or more (or all) of the teeth in a patient's jaw, when installed, so that the installation unit 500 may be fitted onto a patient's jaw. In particular examples, the body portion 502 is formed from an actual impression or computer rendition of the patient's teeth, so that the body portion 502 fits the patient's teeth in a customized manner. In other examples, the body portion 502 may be configured to fit a plurality of patients (and not customized for a particular patient). For example, various installation unit sizes can be made, to fit a large portion of the public, without requiring a customized body portion 502 for each patient.

The installation unit 500 is configured to hold (temporarily) an appliance 600, during installation. In certain examples, the body portion 502 of the installation unit 500 may include a plurality connection sections 502b, such as, but not limited to hooks, tabs, fingers or the like, located or extending along the inward-facing surface of the arch shape (for installing an appliance on the inner or lingual surface of a patient's teeth). In other examples, the body portion of the installation unit may include a similar plurality of connection sections (such as, but not limited to hooks, tabs, fingers or the like) located or extending along the outward-facing surface of the arch shape (for installing an appliance on the outer or buccal surface of a patient's teeth).

The connection sections 502b are configured for retaining temporary wire or tie members 504 that temporarily secure the appliance 600 to the body portion 502 of the installation unit 500. In other examples, the connection sections 502b may be configured with slots or receptacles to receive and temporarily retain arms or other portions of the appliance in a friction fit or snap fitting arrangement. For example, the installation unit 500 may be configured with a plurality of connection sections 502b corresponding in number to the number of arms extending from the rigid bar of the appliance 600 (or corresponding in number to the number of bracket connectors on the appliance 600). As shown in FIG. 43, the appliance 600 may be coupled to the installation unit 500, by a plurality of wires or ties 504, where each wire or tie 504 couples an arm or a bracket connector of the appliance 600 to a respective one of the connection sections 502b of the installation unit 500 (for example, by twisting or tying the wire or tie around or through the arm or bracket connector and around or through the connection section). In this manner, the appliance 600 may be held by the installation unit 500, during an installation procedure (for installing the appliance onto a patient's teeth).

More specifically, an installation process may include forming or selecting an appliance 600 (for example, according to any of the processes described herein or other suitable processes), and forming or selecting an installation unit 500 to correspond to the patient's teeth in that jaw (for example, to match an impression of a patient's teeth) and to correspond to an appliance. After forming the appliance 600, each of the bracket connectors on the appliance may be connected to a corresponding bracket. In addition, the appliance (with the brackets connected) may be secured to the connection sections 502b of the installation unit 500, by wire ties (or other suitable tie structure, or other temporary connection mechanism). Then, the installation unit 500 (with the appliance 600 and brackets attached) can be fitted (placed) on a patient's teeth. In certain examples, the arms of the appliance 600 extend through slots or gaps between adjacent connection sections 502b (such as, but not limited to between hooks, tabs, fingers or the like), located or extending along the arch shape, such that the brackets that are already connected with bracket connectors on the appliance arms are arranged adjacent respective teeth, when the installation unit 500 is fitted (placed) on the patient's teeth. Then, the brackets may be bonded to respective teeth, while the installation unit 500 (holding the appliance 600) is on the patient's teeth. Once the brackets are bonded to the patient's teeth, the appliance 600 may be freed from the installation unit 500 (for example, by untying or cutting the wire or ties), and the installation unit 500 may be removed, while leaving the appliance 600 connected to the brackets in place on the patient's teeth.

In particular examples, the appliance 600 is secured to the installation unit 500 at a position that locates the appliance 600 at its proper installation location on the patient's jaw, when the installation unit 500 is fitted onto the patient's teeth (and the teeth are received within the recess 502a). Therefore, once the installation unit 500 (with the appliance 600 attached) is placed on the patient's teeth, the appliance 600 is automatically aligned with the patient's teeth, in a position for connecting to the brackets on the patient's teeth.

In other examples, the installation unit 500 may be used to install the appliance, after the brackets have been bonded to the patient's teeth. In such examples, the appliance 600 is secured to the installation unit 500 (by wire, other tie structures, or other temporary connection mechanism as described herein). In addition, each bracket is bonded to a respective tooth. Then, the installation unit 500 (with the appliance secured thereto) is placed or fitted onto the patient's teeth. The bracket connector elements on the appliance are then secured to the brackets and the wire, ties or other temporary connection mechanisms are released or removed, to release the appliance from the installation unit 500, while the appliance 600 is secured to the patient's teeth. Then, the installation unit 500 may be removed (slipped off of the patient's teeth), while the appliance 600 remains connected to the patient's teeth.

Another example of an installation unit 700 and an appliance 800 is shown in FIGS. 45-49. The appliance 800 includes (or is connected with) any of the platforms described herein, such as platform 400 as described with regard to FIG. 39 and/or any of the platforms of FIGS. 41A-41E, 42 and 63. Accordingly, the installation unit 700 in FIGS. 45-49 includes a central frame 702 for holding and retaining the platform 400 in place, relative to the appliance 800, for installation with the appliance. The central frame 702 may include one or more hooks, tabs, fingers or the like on which one or more wire ties (or other tie or temporary connection mechanisms) may secure the platform 400 to the hooks, tabs, fingers or the like.

The installation unit 700 and appliance 800 may be installed in a manner similar to the procedure described for the installation unit 500 and the appliance 600. However, further operations of connecting the platform 400 to the appliance 800 may be performed (for example, before the installation unit 700 is placed in the patient's mouth, for simplifying installation procedures). In addition, further operations of installing the platform 400 with one or more TADs or other anchoring devices may be performed, after the installation unit 700 is fitted onto the patient's teeth and before the installation unit 700 is removed.

Accordingly, the installation unit 500 or 700 allows a doctor, clinician or technician to install an appliance (e.g., appliance 600 or 800, or other appliance) or a combination of an appliance and a platform (e.g., platform 400 or other platform) in one procedure. In addition, some of the installation connections (e.g., as between the appliance and the platform) may be carried out prior to inserting the installation unit into the patient's mouth, to further simplify the installation procedure.

While example appliances 600 and 800 and the example platform 400 are shown in FIGS. 43-49, other examples of installation units may be configured as described herein, for any of the other appliances and (or other combinations of appliance and platform) as described herein or in U.S. patent application Ser. No. 15/370,704, filed Dec. 5, 2016.

An installation unit as described herein may be configured of any suitable material including, but not limited to a plastic, a rubber, a metal, a composite material, or the like, or combinations thereof. The installation unit may be formed by any suitable manufacturing process including, but not limited to molding, 3D printing, machining, or the like.

Various example appliances or appliance members described herein (or other suitable appliances or appliance members) include a rigid bar that is configured to extend along two or more (or a plurality of) adjacent teeth in a patient's jaw (the upper jaw or the lower jaw), when installed. In some examples, the rigid bar includes X embodiment features, or Z embodiment features, or a combination of X and Z embodiment features as described herein. In any of those examples (or other suitable examples), the appliance or appliance member may include a first portion that, when installed, extends to or along one or more teeth (or a plurality of adjacent teeth) in one of the patient's jaws, and a second portion that extends to or along one or more teeth (or a plurality of adjacent teeth) in the other one of the patient's jaws. In those examples, the appliance or appliance member may include an inter-arch feature (such as, but not limited to an inter-arch spring member) that extends from the first portion of the appliance to the second portion of the appliance (from one jaw to the other jaw), when installed.

In examples having one or more inter-arch feature, the appliance or appliance member may include one or more (or a plurality of) first bracket connectors (or male connector elements) that are configured to connect to one or more (or a plurality of) corresponding brackets on one or more (or a plurality of) associated teeth in one of the patient's jaws (the upper jaw or the lower jaw), and one or more (or a plurality of) second bracket connectors (or male connector elements) that are configured to connect to one or more (or a plurality of) corresponding brackets on one or more (or a plurality of) associated teeth in the other one of the patient's jaws (the other one of the upper jaw or the lower jaw). The bracket connectors (or male connector elements) and associated brackets may include any of the examples described herein or in U.S. patent application Ser. No. 15/370,704, filed Dec. 5, 2016, or other suitable examples.

Figure 50:
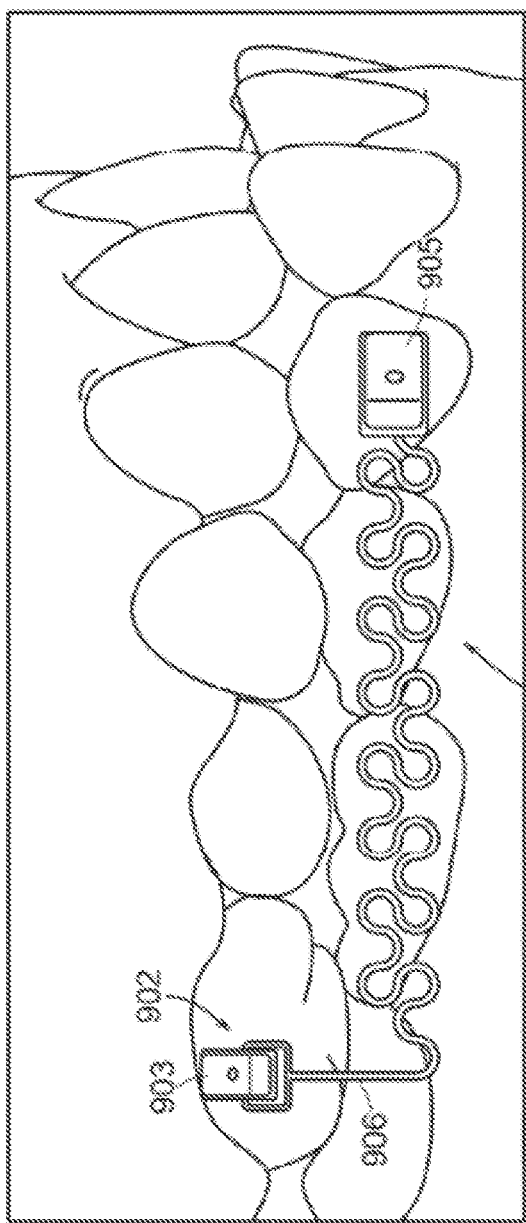
FIGS. 50-55 are perspective views of appliances having inter-arch members.

In FIG. 50, an example appliance 900 having an inter-arch feature, in an installed arrangement, installed on teeth on the patient's upper and lower jaws. The appliance 900 includes a first appliance portion 902 connected to a bracket 903 that is secured on a tooth in the patient's upper jaw, and a second appliance portion 904 connected to a bracket 905 secured on a tooth in the patient's lower jaw. In the example in FIG. 50, the first portion 902 of the appliance 900 includes or is a bracket connector. In the example in FIG. 50, the second portion 904 of the appliance 900 extends along a plurality of teeth in the patient's lower jaw, at least when the patient's jaws are in a closed position as shown in the drawing.

In the example in FIG. 50, the appliance 900 includes an arm 906 that forms the inter-arch feature when the patient's jaws are in a closed position as shown in the drawing. The appliance 900 also includes a rigid bar having a plurality of loop or curved features (for example, according to Z embodiment features) that forms the second portion 904 of the appliance, and can extend to form some of the inter-arch feature when the patient's jaws are in an open or partially open position.

Figure 51:
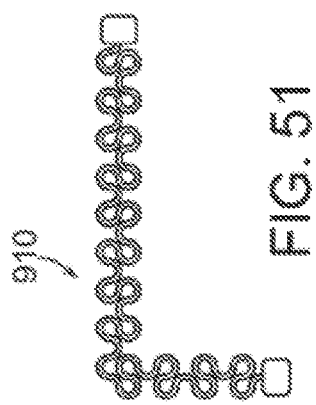
Figure 52:
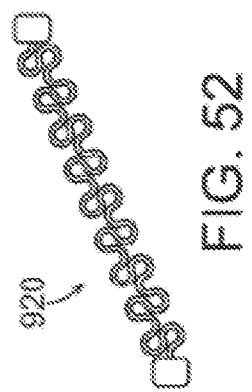
Figure 53:
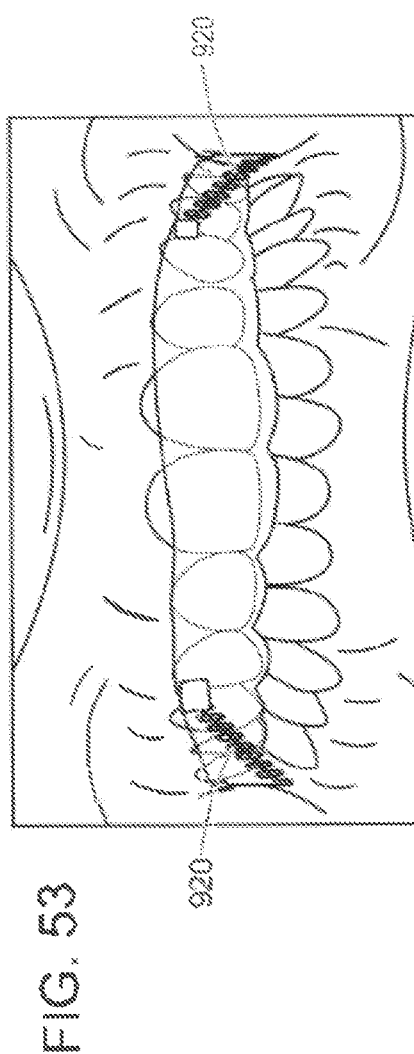
Figure 55:
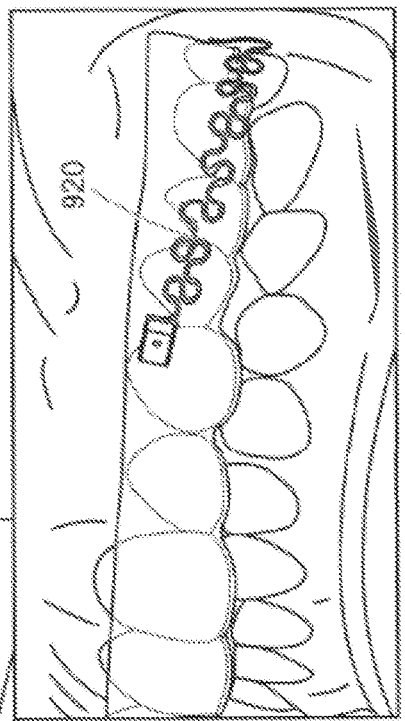
Figure 54:
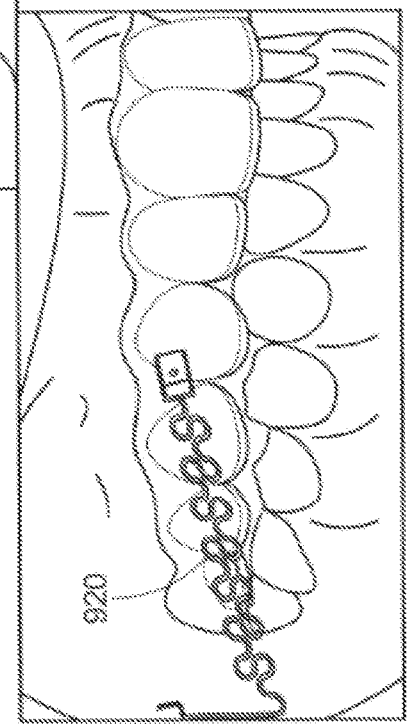

Other examples of appliances 910 and 920 are shown in FIGS. 51 and 52, where the entire length of the appliance includes a rigid bar having a plurality of loop or curved features (for example, according to Z embodiment features). In the example in FIG. 51, the direction of the length dimension of the rigid bar forms an angle (such as a right angle or other suitable angle) along its length, between a first and second end of the appliance. In the example in FIG. 52, the direction of the length dimension of the rigid bar is generally linear. Each of the appliances 910 and 920 may be configured such that the bracket connector on one end of the appliance is configured to connect to a bracket on a tooth in one of the patient's jaws, while the bracket connector on the other end of the appliance is configured to connect to a bracket on a tooth in the other one of the patient's jaws. Further examples of appliances corresponding to appliance 920 are shown in FIGS. 53-55, installed on teeth of a patient.

In each of the examples shown in FIGS. 50-55, the appliance includes one bracket connector at one end of the appliance and a second bracket connector at a second end of the appliance, with no further bracket connectors. In other examples, the appliance (or appliance member) may include one or more (or a plurality of) further bracket connectors between the bracket connectors at the first and second ends (or instead of one or more of the bracket connectors at the first and second ends) of the appliance (or appliance member). In the examples shown in FIGS. 50-53, the bracket connectors and brackets have an annular or ring shape configuration, for example similar to that described for the bracket connector 140a in FIG. 13, and the brackets 903 and 905 have a configuration, for example, similar to that described for the bracket 142 in FIG. 14. In other examples, the appliances or appliance members described with regard to FIGS. 50-53 may include other bracket connectors as described herein or in U.S. patent application Ser. No. 15/370,704, filed Dec. 5, 2016, or other suitable bracket connectors, for connection with associated brackets.

Various example appliances or appliance members described herein (or other suitable appliances or appliance members) are configured to selectively connect with a plurality of brackets secured to a corresponding plurality of teeth in a patient's jaw, as described herein. In certain procedures as described herein and in U.S. patent application Ser. No. 15/370,704, filed Dec. 5, 2016, an appliance (or series of appliances) may be installed and maintained on the patient's teeth for a period of time, to effect a desired FTA (or an ITA), after which the appliance is removed. In some examples, after an appliance has been removed from a patient, it may be desirable for the patient to wear a slip-on teeth aligner to provide additional teeth-movement forces or to maintain a desired tooth or teeth arrangement and position.

Figure 56:
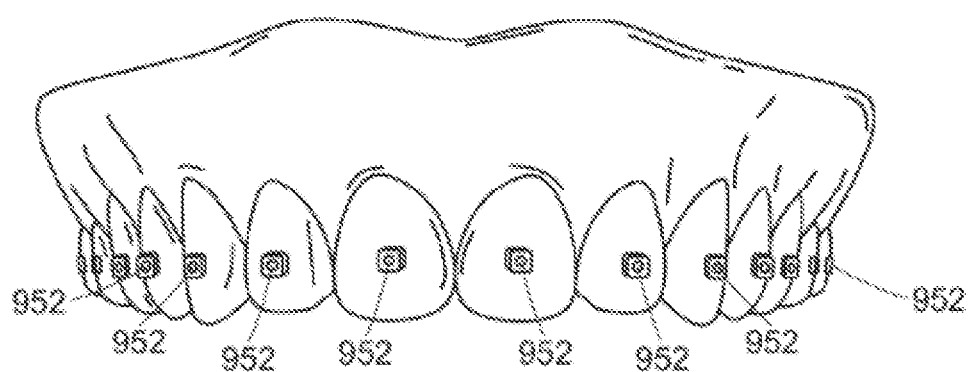
FIG. 56 is a perspective view of a patient's teeth with brackets.
Figure 57:
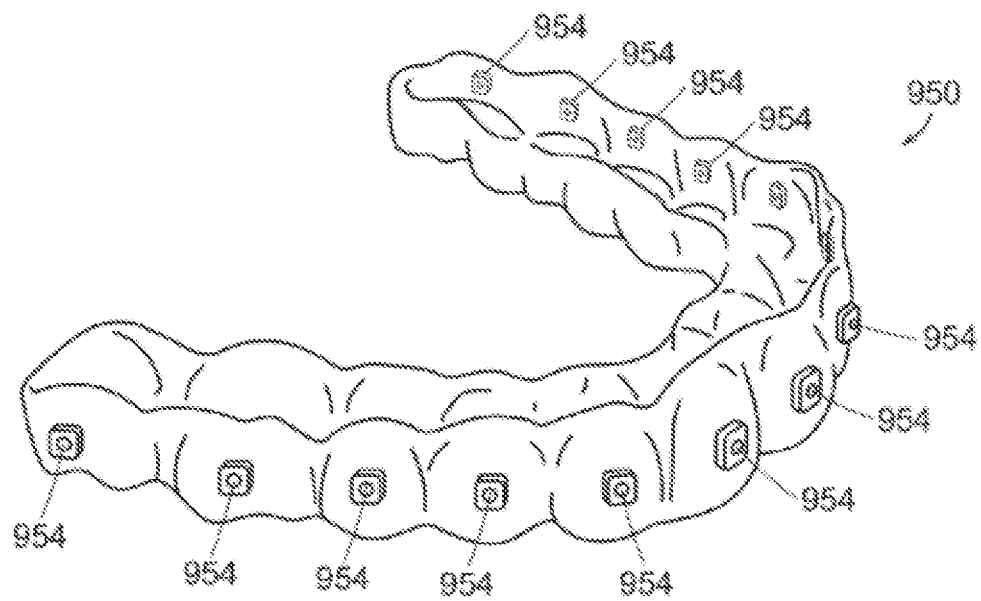
FIG. 57 is a perspective view of an aligner on a patient's teeth.

In particular examples as shown and described with reference to FIGS. 56 and 57, the slip on aligner includes an aligner body 950 configured to fit over a plurality (or all) of the teeth in a patient's jaw (upper jaw or lower jaw, where FIGS. 56 and 57 show teeth and an aligner for an upper jaw). In particular examples, the aligner body 950 is formed from a mold made of an impression of a patient's teeth or jaw. The aligner body 950 may be formed of a plastic, transparent plastic, or other suitable material. The aligner body 950 may be made by any suitable process including, but not limited to molding, 3D printing, machining, or the like. In some examples, the aligner body 950 may be made of a material and shape similar to aligners of the type made and sold under the Invisalign™ trademark by Align Technology. In other examples, the aligner body 950 may be made of other suitable materials or shapes.

In particular examples, the aligner body 950 is configured to engage and interact with one or more brackets 952 that are secured to the patient's teeth. The brackets 952 may correspond to any of the brackets (or female connector elements) described herein or in U.S. patent application Ser. No. 15/370,704, filed Dec. 5, 2016, or may correspond to any other suitable bracket. In particular examples, the aligner body 950 is configured to engage and interact with one or more (or all) of the same brackets 952 that were already secured to the patient's teeth and that were previously connected with an appliance (or series of appliances) before the appliance was removed. In those examples, after removal of the appliance (or of the last of the series of appliances) from the brackets on a patient's teeth, the brackets remain on the patient's teeth and a slip on aligner body is installed on the patient's teeth, over the brackets. In those examples, the appliance (or series of appliances) may correspond to any of the appliances described herein or in U.S. patent application Ser. No. 15/370,704, filed Dec. 5, 2016, or may correspond to any other suitable appliances.

In particular examples, the aligner body 950 has one or more (or a plurality of) engaging surfaces that are configured to engage a corresponding one or more (or plurality of) brackets 952, when the aligner is installed on the patient's teeth, over the teeth on which the brackets are secured. In certain examples, the aligner includes a plurality of receptacles or recesses 954 that include or define the engaging surfaces. Each receptacle or recess 954 has one or more engaging surface or surfaces for receiving and engaging a bracket 952 on the patient's teeth when the aligner body 950 is installed over the patient's teeth (including the tooth on which the bracket is secured). When the aligner body 950 is slipped onto the teeth, over the brackets 952, the brackets 952 function as handles on which the aligner body 950 is able to interface (by abutting) and apply forces on the teeth, for moving, aligning or retaining teeth positions.

A slip on aligner may be made of any suitable material including, but not limited to a plastic, a thermoplastic, a rubber, a metal, a composite material, or the like, or combinations thereof. The aligner may be formed by any suitable manufacturing process including, but not limited to molding, 3D printing, machining, or the like.

Systems and processes according to any of the examples described herein or other examples may include a comfort cover or retainer device that is configured to be worn by a patient, while the patient has the appliance in the mouth.

The cover or retainer may be a comfort cover that covers the brackets and the appliance during treatment, and has a smooth outer surface to provide additional comfort to the user. In some examples, the comfort cover or retainer is configured to fit over and cover an appliance and brackets as described herein. In other examples, the comfort cover or retainer may be configured to cover other types of dental appliances, traditional braces, or the like.

In particular examples, the comfort cover or retainer may include a retainer body having a shape to fit over and cover some or all of the teeth in a patient's jaw (upper jaw or lower jaw). In particular examples, the retainer body is shaped to fit over at least some of the patient's teeth and provide a sufficiently tight or snug fit on the patient's teeth, so as to retain the retainer body on the patient's teeth, yet allow the patient to selectively remove (slide off) the retainer from the teeth.

In some examples, the comfort cover or retainer may be configured similar to (and of similar materials as) the aligner body described above, but is configured to cover the appliance and bracket during treatment, while the appliance is secured to the brackets. In other examples, the comfort cover or retainer may be made of other suitable materials or shapes. The retainer body may be formed by any suitable process as described herein and may be formed from an impression taken of the patient's teeth. In particular examples, the retainer body is shaped to provide a sufficiently tight fit to be retained on a patient's teeth (over an appliance and brackets), yet also provide space for one or more teeth to move, without obstruction, between an OTA and an FTA, or between an OTA and an ITA, or between two ITAs, or between an ITA and an FTA.

In that regard, the retainer body may be configured to have a shape and dimension that corresponds to and fits over the patient's current teeth arrangement (with an appliance and brackets), with sufficiently tight fitting portions on at least some of the teeth covered by the retainer body to hold the retainer onto the teeth, yet also include sufficient spacing adjacent one or more of the teeth to allow the teeth to move (due to the action of an appliance) without obstruction or friction from retainer body. For example, a clearance or spacing may be provided adjacent one or more of the teeth, to allow teeth movement, where the spacing may be uniform along some or all of the retainer body, or may vary along the retainer body so as to be different for different teeth locations. A clearance or spacing of, for example, 0.2 mm may be provided adjacent one or more teeth that are being moved by an underlying appliance. In other examples, the clearance or spacing may range from about 0.1 mm to about 0.3 mm. In other examples, other suitable clearance or spacing may be used.

The retainer body may have a relatively smooth outer surface that avoids or minimizes contact between the patient's tongue or cheek and sharp or protruding portions of the appliance or brackets. In further examples, comfort covers may have sufficient rigidity to provide splints for treating certain conditions, such as, but not limited to temporomandibular joint (TMJ) conditions. In further examples, comfort covers may be configured to provide additional protection of the patient's teeth or appliances secured to the teeth, for example, in sports or other activities, similar to a sports mouth guard.

The retainer body may be formed of any suitable material, such as, but not limited to a flexible, plastic or thermoplastic material, a rubber, a metal, a composite material, or the like, or combinations thereof. The retainer body may be made by any suitable manufacturing process including, but not limited to molding, transforming or suck down machine, 3D printing, machining, or the like.

Any of the example appliances or appliance members described herein (or other suitable appliances or appliance members) may be configured with a computer-aided procedure for selecting or configuring one or more (or all) of the arms on the appliance or appliance member (e.g., arms for an X embodiment feature), one or more (or all) of the loop or curved features (e.g., loop or curved features for a Z embodiment feature).

In particular examples, the computer-aided procedure employs an algorithm for selecting or configuring an arm or a loop or curved feature, for example, from one or more predefined sets of options or one or more ranges of options. Thus, for example, a set of options or a range of options may be predefined for one or more parameters associated with an arm or a loop or curved feature. The one or more parameters associated with an arm may include, but are not limited to, the overall length of the arm, the length of the arm section between the spring member and the bracket connector (e.g., corresponding to arm section 100c of arm 100 in FIG. 10), the shape or configuration of the spring member, the shape or configuration of the bracket connector on the distal end of the arm, the width dimension of one or more sections of the arm, the thickness dimension of one or more sections of the arm, or the like. The one or more parameters associated with a loop or curved feature, or an Z embodiment feature may include, but is not limited to the shape or configuration of the loop or curved feature, the width dimension of one or more sections of the loop or curved feature, the thickness dimension of one or more sections of the loop or curved feature, the shape, configuration or type of bracket connector, or the like.

In particular examples, the computer-aided procedure employs an algorithm for selecting or configuring an appliance or an arm or curved or loop feature of an appliance includes, as input, (but is not limited to) one or more values representing one or more of: (a) up to three translational and up to three rotational movements from an OTA to an ITA or FTA, or from an ITA to another ITA or FTA; (b) the surface of periodontal ligament (PDL) or the area of the root of a or each tooth; (c) bone density of the patient; (d) biological determinants for example, obtained from saliva, gingival fluid (GCF), blood, urine, mucosa, or other sources; (e) gender of the patient; (f) ethnicity of the patient; (g) the jaw (maxilla or mandible) for which the appliance is to be installed; (i) the number of teeth on which the appliance is to be installed; and (j) mechanical properties of the tissue (lips, tongue, gingiva) and bone around the teeth to be moved. An output generated by the computer-aided procedure, based on such input, includes, but is not limited to one or more of: (a) a design of an arm in an X embodiment appliance section, or a design of a curved or loop feature of a Z embodiment appliance section; (b) a width or cut-width of one or more of such arms or curved or loop features; (c) a thickness dimension of the appliance or of curved or loop feature or other sections of the appliance; (d) mechanical properties of such arms or curved or loop features including but not limited to amount of flexibility, or a magnitude of bias force or resilience; (e) transformational temperature of the nitinol (or other material) in one or more (or each) section of the appliance. The algorithm may employ finite element analysis (FEA) or other suitable analysis process.

The procedure may be configured to select one (or more than one) arm, loop or curved feature, bracket connector, or parameter thereof, based on one or more input data. For example, input data may include, but is not limited to, a type of a tooth (e.g., molar, canine, incisor, etc.) or a size of a tooth. A larger tooth (such as a molar) may require larger arms or larger, wider or thicker loop or curved features for providing a greater force, than for a smaller tooth (such as an incisor). Alternatively or in addition, input data may include the size of the periodontal ligament (PDL) of one or more teeth. The size of the PDL may be obtained by any suitable process including, but not limited to, CBCT scan or other imaging technique. Other input data may include, but is not limited to, the number or direction of forces to be applied to a tooth or teeth in a three-dimensional space. For example, a desired tooth movement direction may require one or more shapes or configurations of spring members or of loop or curved features, that differ from the shapes or configurations required for a different tooth movement direction. Other input data may include but is not limited to, the number or direction of rotational forces (or torque) to be applied to a tooth or teeth. For example, a desired tooth movement in a rotational direction may require one or more shapes or configurations of spring members or of loop or curved features, that differ from the shapes or configurations required for a different tooth movement direction. In other examples, other suitable input data may be employed. The computer-aided process employs a computer programed or configured with suitable non-transient software, hardware, firmware, or combinations thereof, to generate an output (such as one or more selected arm configurations or one or more selected loop or curved feature configurations), based on the one or more input data.

In particular examples, computer-aided processes can be employed to make customized appliances or appliance members, for each given patient. In other examples, appliances or appliance members may be made in a plurality (set number) of predefined sizes, shapes, configurations, or the like, based on a population group. Accordingly, a different semi-customized size, shape or configuration (or combination) would be configured to fit each different selected portion of the population group. In that manner, a more limited number of different appliance sizes, shapes and configurations may be made to accommodate a relatively large portion of the population. Similar manufacturing processes, for producing sizes, shapes and configurations suitable for population groups (rather than individual patients) may be applied to the manufacture of aligners and comfort covers or retainers as described herein.

Systems and processes according to any of the example appliances described herein or other example appliances may include or operate with an expander device. An expander device may include, but is not limited to a palatal expansion device, a rapid palatal expander (RPE), a mini screw assisted rapid palatal expansion (MARPE) device, or a Maxillary Skeletal Expansion (MSE) device. Such expander devices are installed on a patient's palate, for applying an expansion force to spread or widen the palate. The expander device may include an expandable platform having one or more openings or TAD connector features through which one or more TADs (or other suitable anchorage devices) may be extended, to secure the expandable platform to the patient's maxilla. In some examples, the expander device may include a threaded screw or other operator that can be operated by a doctor, clinician or technician, to adjust the expansion force (for example, as part of a treatment plan).

An expander device according to examples described herein includes one or more connection features for selectively connecting an appliance to the expander device, such as, but not limited to any of the appliances as described herein. Accordingly, in such examples, expansion and alignment forces may be provided, simultaneously.

In particular examples, an expander device can provide an anchoring platform having one or more anchoring locations for an appliance. An expander device may be provided with one or more (or a plurality) of appliance connector elements, which may correspond to appliance connector elements 400c, 400d and 400e for connecting to a platform connection arm of an appliance, as discussed above, or may have other suitable configuration for connecting to an appliance. For example, each appliance connector element may have a configuration similar to bracket (or female connector elements) described herein, including, but not limited to the bracket 160 described above.

Figure 58:
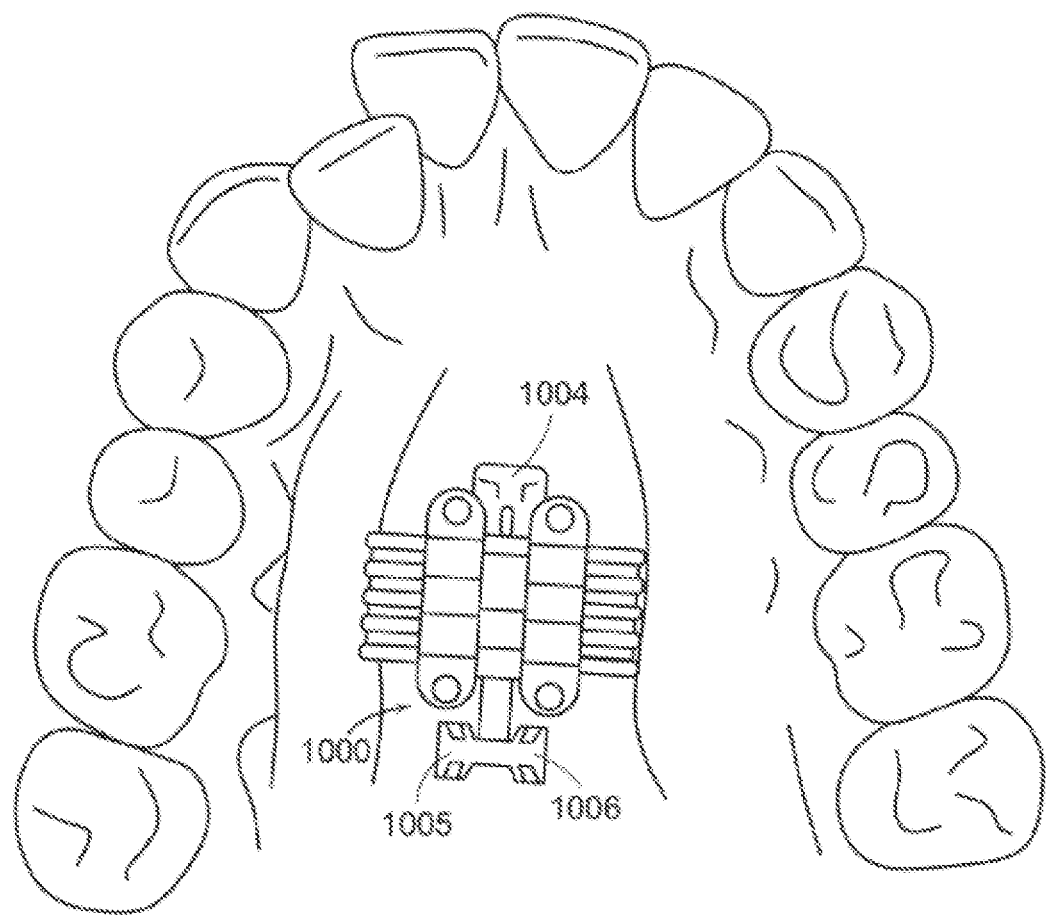
FIG. 58 is a perspective view of an example expander with appliance connectors, represented as installed on a patient's maxilla.
Figure 59:
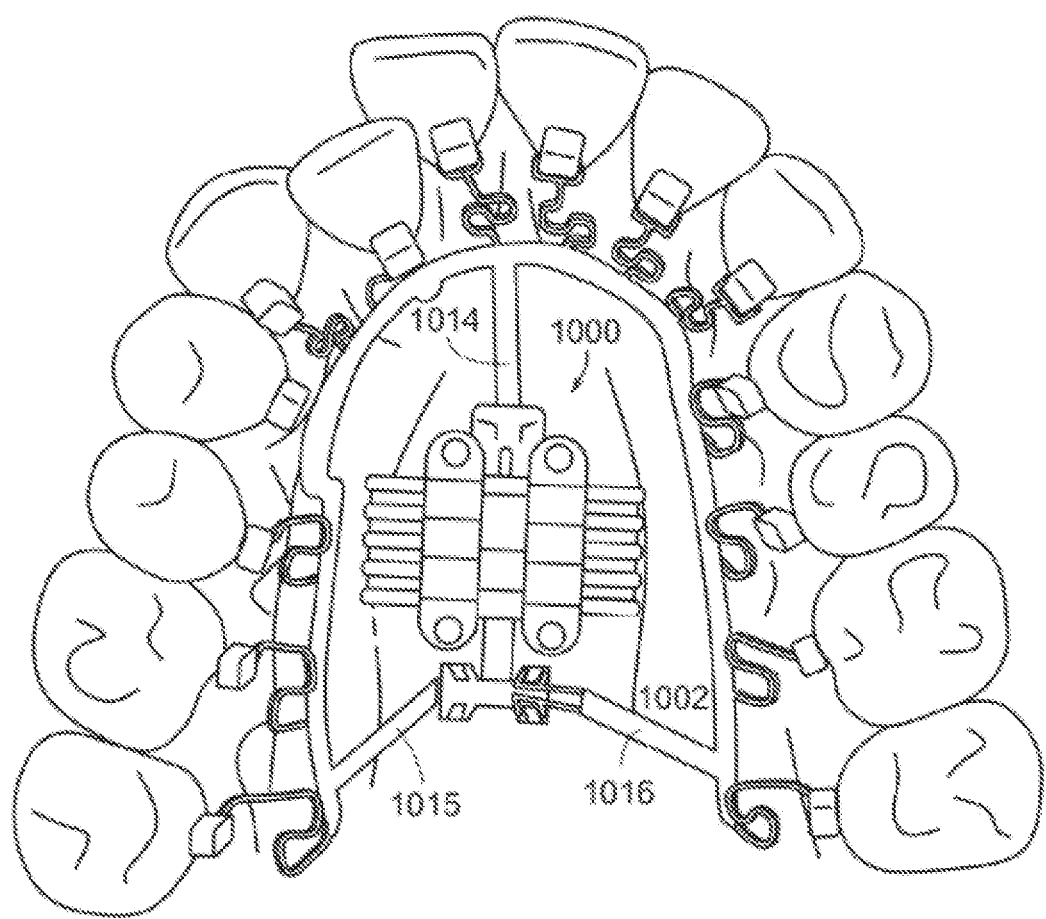
FIG. 59 is a perspective view of the example expander of FIG. 58, connected with an appliance, represented as installed on a patient.

An example of an expander device 1000 that provides an expander function, but also provides an anchoring platform, is shown in FIGS. 58 and 59, as installed on a patient's palate. The expander device 1000 is shown in FIG. 58, as installed on a patient's palate, before connection with an appliance (or after removal of an appliance). The expander device 1000 is shown in FIG. 59, connected with an appliance 1002 that is installed on the patient's teeth. The appliance 1002 may be any of the appliance examples described herein or another suitable appliance.

In particular examples, the expander device 1000 may be installed on the patient, before the appliance is installed. Then the appliance may be installed on the patient's teeth. Then the appliance may be connected to the appliance connection elements on the expander device, to help anchor the appliance.

The expander device 1000 in FIGS. 58 and 59 has or operates with three appliance connector elements 1004, 1005 and 1006. In the example in FIGS. 58 and 59, each appliance connector element 1004, 1005 and 1006 has a winged shape (having two projections or wings), similar to the bracket 160 described above. In the example in FIGS. 58 and 59, two of the appliance connector elements 1005 and 1006 are arranged near the back (or molar teeth end) of the expander device, for positioning near the patient's molars when installed. A third appliance connector element 1004 is arranged near the incisor teeth end of the expander device, for positioning near the patient's incisors when installed. In other examples, the expander device 100 may include any suitable number, configuration and location of appliance connector elements, for providing anchor positions for one or more platform connection arms of an appliance.

The appliance 1002 includes three platform connection arms 1014, 1015 and 1016, for selectively connecting to the appliance connector elements 1004, 1005 and 1006, respectively, as shown in FIG. 59. In other examples, the appliance may include any suitable number of platform connection arms, such as a number corresponding to the number of appliance connector elements provided on the expander device. Each platform connection arm 1014, 1015 and 1016 has a distal end on which a platform connector element is provided, for connecting to a respective appliance connector element 1004, 1005 and 1006. In the example in FIG. 59, each platform connector element has a configuration corresponding to the bracket connector (or male connector element) 150 discussed above, for selectively connecting to the winged shaped appliance connector element 1004, 1005 or 1006 (similar to the manner in which the bracket connector 150 selectively connects with the bracket 160 as discussed above).

Figure 60:
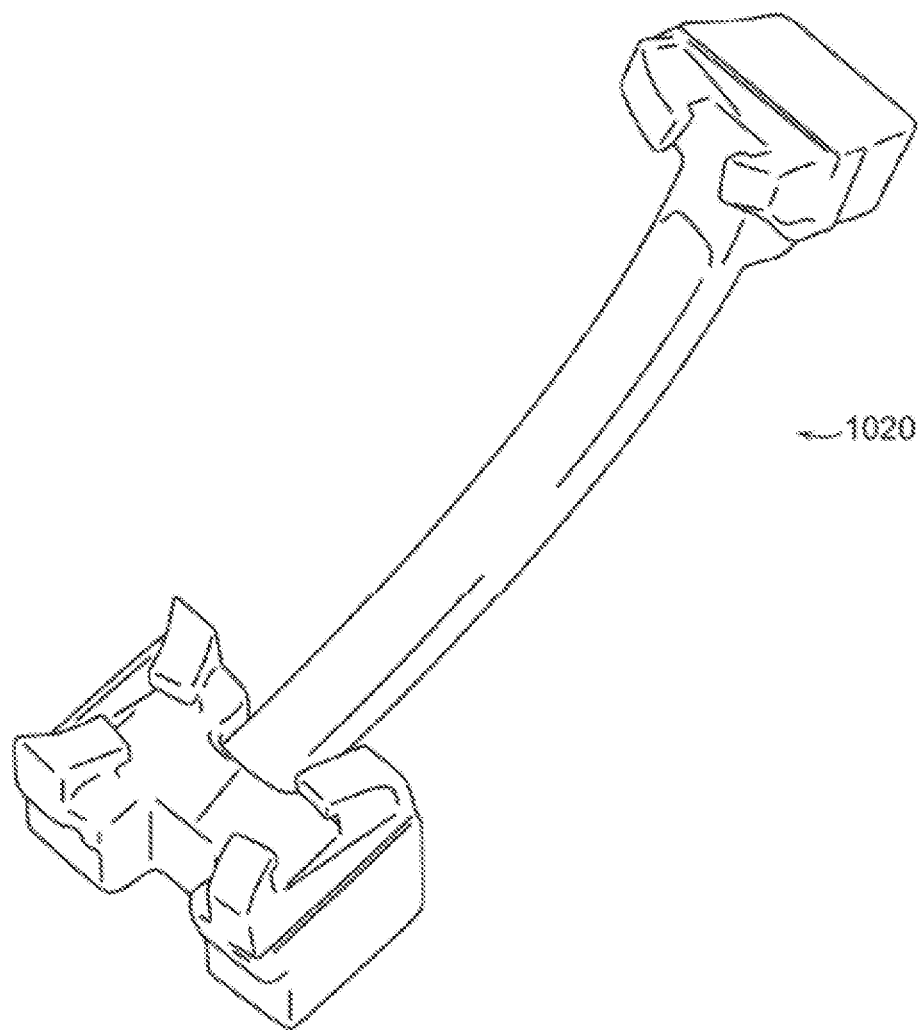
FIG. 60 is a perspective view of an attachment hook for connecting an expander to an appliance.

In certain examples, the appliance connector elements 1004, 1005 and 1006 may be formed on the body of the expander device 1000. In other examples, the appliance connector elements 1004, 1005 and 1006 are provided on a hook member 1020 (FIG. 60) that is configured to be attached to the body of an expander device 1000. In FIG. 59, the hook member 1020 is attached to the body of the expander device 1000, for example, to a bottom surface (in the orientation of FIG. 59) of the expander device 1000 by an adhesive, weld, snap or friction fit or other suitable connection mechanism. In certain examples, the hook member 1020 is configured to attach to the body of a standard expander device 1000. In other examples, the hook member 1020 is configured to attach to a custom-made expander device.

Figure 61:
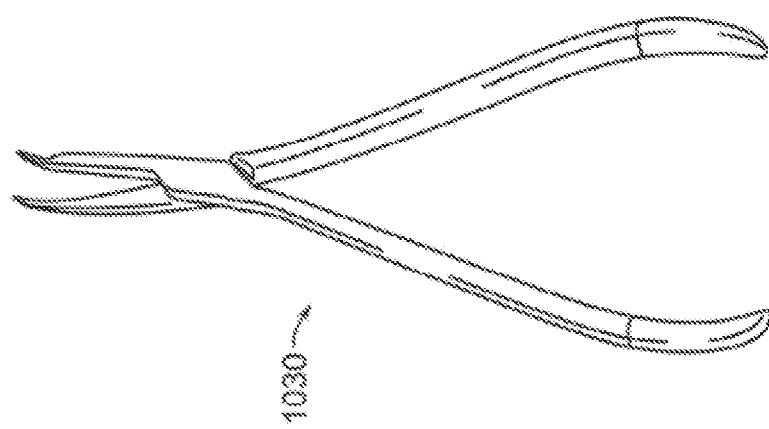
FIG. 61 is a perspective view of a traditional Weingart tool.

Systems and processes according to any of the examples described herein or other examples may be installed on a patient in any suitable manner. Typically, tools are used to hold and selectively squeeze and release bracket connectors or other components during installation. A common dental tool is shown in FIG. 61 and is referred to as a Weingart orthodontic pliers 1030. However, as appliance components located in molar or other regions of a patient's jaw can be difficult to reach and manipulate, using standard Weingart style tools.

Figure 62:
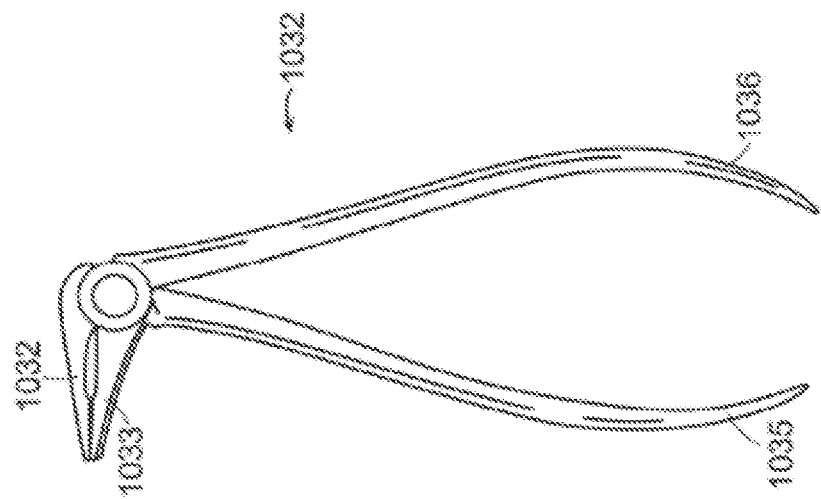
FIG. 62 is a perspective view of a tool according to an example embodiment.

Accordingly, an example of an orthodontic pliers tool 1032 having a configuration similar in some manners to a Weingart pliers is shown in FIG. 62. The Weingart tool has a pair of handles that are pivotally connected to each other at a pivot point, and are manually pivotal to move in a direction to spread apart or close together. The Weingart tool has a pair of jaws that are moveable to spread apart or close together, with the pivotal movement of the handles.

However, the tool 1030 has a pair of jaws 1033 and 1034 that extend from the pivot point, at an angle relative to an axis AA extending (symmetrically) between handles 1035 and 1036. In the example in FIG. 62, the jaws 1033 and 1034 are directed at an angle of about 90 degrees from the axis AA. In other examples, the jaws 1033 and 1034 may be directed at other angles (e.g., within the range of 60 to 120 degrees) of the axis AA.

The embodiments disclosed herein are to be considered in all respects as illustrative, and not restrictive. The present disclosure is in no way limited to the embodiments described above. Various modifications and changes may be made to the embodiments without departing from the spirit and scope of the disclosure. Various modifications and changes that come within the meaning and range of equivalency of the claims are intended to be within the scope of the disclosure.

Figure 63:
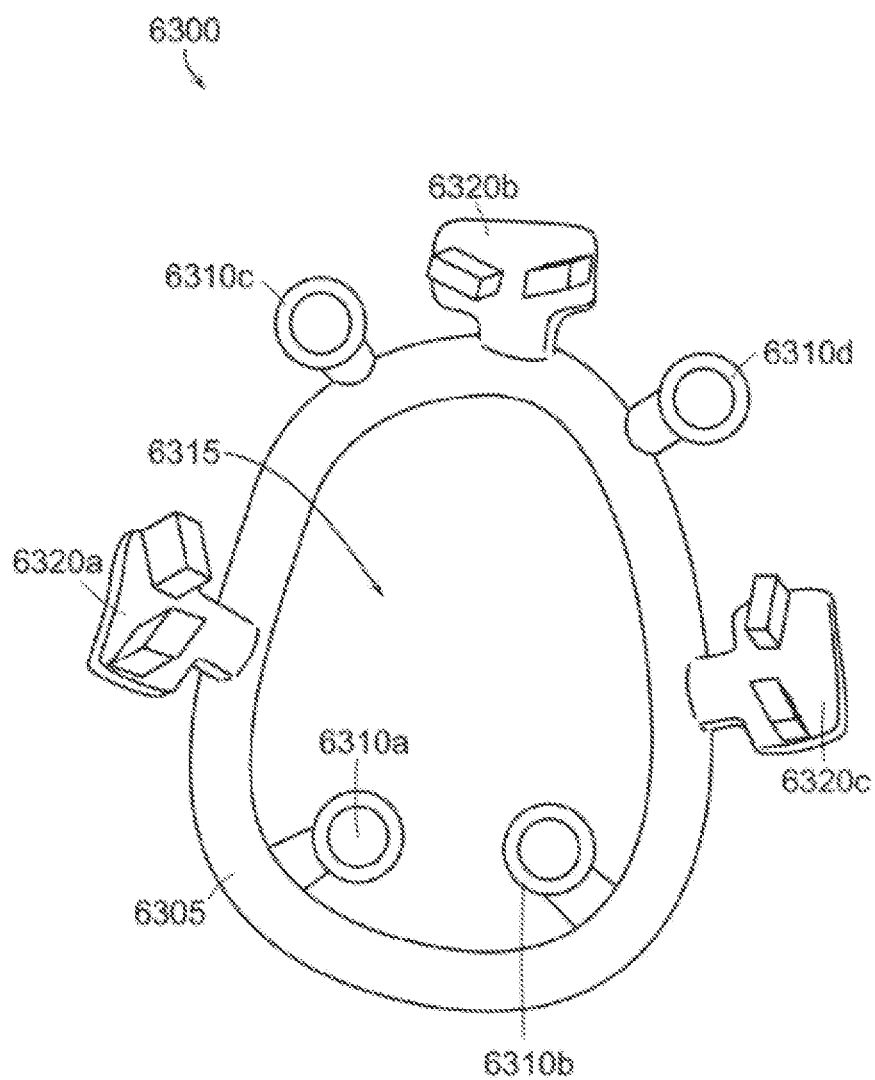
FIG. 63 is a perspective view of a device to be installed in a patient's mouth, in accordance with embodiments of the present technology.

FIG. 63 is a perspective view of an anchoring platform 6300 (or "platform 6300") configured to be installed in a patient's mouth, in accordance with embodiments of the present technology. Similar to the anchoring platforms described herein, for example with respect to FIGS. 39-42, the platform 6300 is configured to be positioned within the patient's oral cavity to secure the appliances of the present technology to local hard and/or soft tissue, including tissue comprising the palate, the maxilla bone, and/or the mandible bone. According to some embodiments, for example as shown in FIG. 63, the platform 6300 includes an annular body 6305 defining an opening 6315, one or more anchorage connector elements 6310a, 6310b, 6310c, 6310d (collectively referred to as "anchorage connector elements 6310") configured to facilitate fastening of the platform 6300 to the patient's palate, and one or more appliance connector elements 6320a, 6320b, 6320c (collectively referred to as "appliance connector elements 6320") configured to be coupled to an orthodontic appliance for repositioning a patient's dentition. Each of the anchorage connector elements 6310 and/or appliance connector elements 6320 can extend inwardly from the body 6305 toward the opening 6315 or can extend outwardly from the body 6305, away from the opening 6315. In the embodiments depicted by FIG. 63, connector elements 6310a, 6310b extend inwardly toward the opening 6315 and connector elements 6310c, 6310d, and 6320a-c extend outwardly, away from the opening 6315. Other configurations are within the scope of the present technology.

The body 6305 can have an ovular shape (as shown in FIG. 63) or can define or enclose other shapes, such as a circle, rectangle, a square, a polygon, any non-polygonal shape, etc. In some embodiments, the body 6305 forms an open frame, such as a C-shape, an arch, and/or any other structure having two longitudinal ends that are spaced apart and/or not connected. According to various embodiments, the body 6305 comprises a solid structure. The body 6305 can be formed of one or more metals, polymers, or other substantially rigid materials.

Although the device 6300 shown in FIG. 63 includes four anchorage connector elements 6310 and three appliance connector elements 6320, in some embodiments the device 6300 may include more or fewer anchorage connector elements 6310 (e.g., one, two, three, five, seven, etc.) and/or more or fewer appliance connector elements 6320 (e.g., one, two, four, five, seven, etc.). Each of the anchorage connector elements 6310a-d is configured to hold a permanent anchorage device or a temporary anchorage device (TAD). In certain examples, the anchorage connector elements 6310 may correspond to the TAD holders described in U.S. patent application Ser. No. 15/370,704, filed Dec. 5, 2016 (for example, at reference numbers 812, 904 or 1012 in that application). The anchorage connector elements 6310 allow a clinician to secure the body 6305 of the platform 6300 to a patient's palate using one or more anchoring devices such as, but not limited to screws, temporary anchorage devices TADs or other suitable anchorage device that extend into the patient's palate (soft and hard tissue). In certain examples, each anchorage device connector element 6310a-d may have an opening (e.g., an opening in an annular extension) through which a screw, TAD or other anchor device may extend. In some examples, other suitable connector element configurations may be employed for receiving or holding a screw, TAD or other anchor device.

Each of the appliance connector elements 6320 can include a base portion 6325 extending directly from the body 6305 and one or more protrusions 6330 (only one labeled) extending from the base portion 6325. When the platform 6300 is installed within the patient's mouth on or adjacent the palate, the base portions 6325 may angle away from the body 6305 along a dimension generally parallel to palate, and the protrusions 6330 may extend away from the base portions 625 substantially perpendicular to the plane of the respective base portion 6325. In some embodiments, the protrusions 6330 associated with a given base portion 6325 may be spaced apart from one another such that a gap is formed therebetween. In some embodiments, the appliance connector elements 6320 or portions thereof, as well as the positional arrangement of one or more portions of the appliance connector elements 6320 (including the protrusions 6330) can be configured to secure another device thereto. For example, as explained above with respect to FIGS. 39-42, the appliance connector elements 6320 or portions thereof may be configured to be selectively connected with a respective platform connection arm on an appliance (such as any of the appliances disclosed herein). Each appliance connector element 6320a-c may have a configuration corresponding to any of the brackets (or female connector elements) described herein, described in U.S. patent application Ser. No. 15/370,704, filed Dec. 5, 2016. Each platform connection arm of the appliance may have a configuration corresponding to any of the bracket connectors (or male connector elements) described herein, described in U.S. patent application Ser. No. 15/370,704, filed Dec. 5, 2016. In other examples, each appliance connector element and each platform connection arm may have any other suitable configuration for selectively connecting and disconnecting from each other. In certain examples, each appliance connector element 6320a-c has a configuration that includes a receptacle for receiving and holding a portion of respective platform connection arm of an appliance.

The anchorage connector elements 6310 and/or the appliance connector elements 6320 can be formed of one or more metals, polymers, or other substantially rigid materials. In some embodiments, the body 6305 and/or one, some, or all of the anchorage connector elements 6310 and/or one, some, or all of the appliance connector elements 6320 may comprise a single component having a continuous surface. In several embodiments, the body 6305, all of the anchorage connector elements 6310, and all of the appliance connector elements 6320 comprise a unitary, integrally formed structure.

Figure 64:
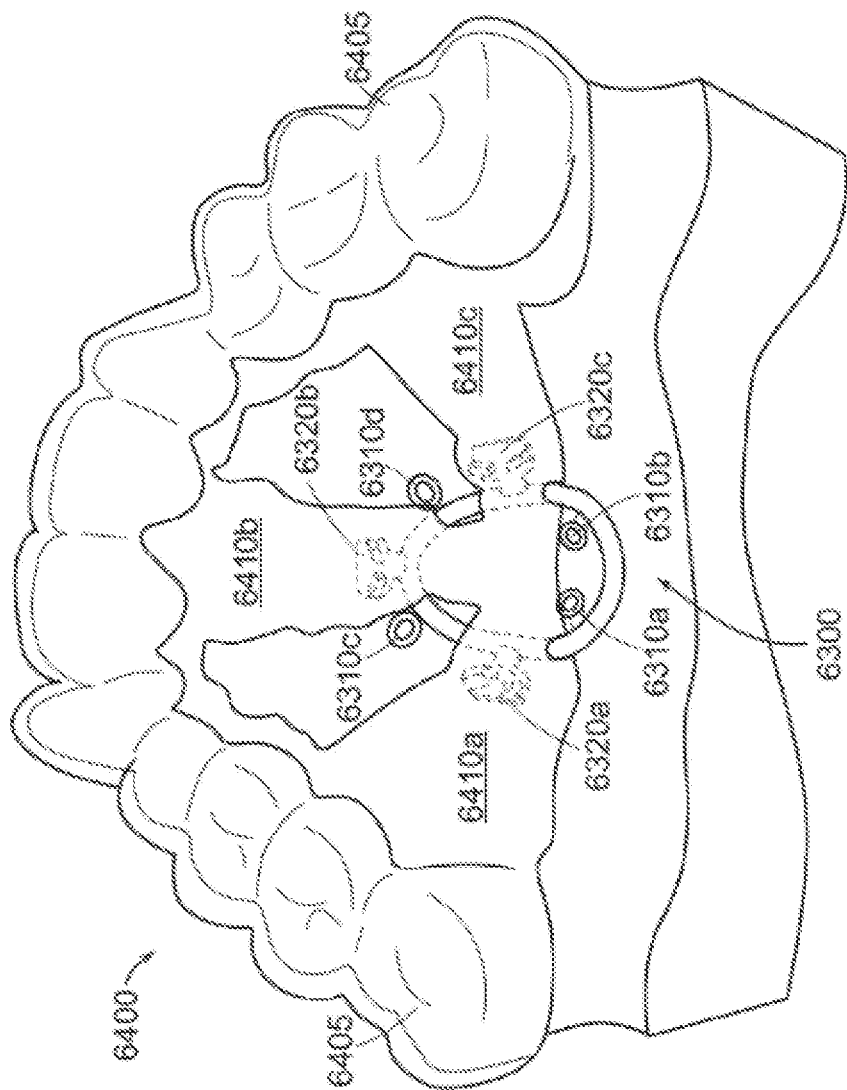
FIG. 64 is a perspective view of the device of FIG. 63 coupled to a positioning member disposed over a patient's teeth, in accordance with embodiments of the present technology.

Several aspects of the present technology may include a positioning member to guide installation of the platforms disclosed herein within the patient's mouth. In particular, the positioning members may be configured to position the anchorage connector elements at a desired location(s) along the palate and/or mandible to ensure correct placement of the platform once installed. FIG. 64, for example, is a perspective view of the platform 6300 of FIG. 63 coupled to a positioning member 6400 disposed over a patient's teeth, in accordance with embodiments of the present technology. While the positioning member 6400 is described below with reference to the platform 6300, it will be appreciated that the positioning member 6400 can be used with any of the platforms disclosed herein, including platforms 400, 410, 420, 430, 440, 450 and 460. As shown in FIG. 64, the positioning member 6400 can include a first portion 6405 configured to be positioned at the patient's teeth, and one or more second portions 6410a, 6410b, 6410c (collectively referred to as "second portions 6410") coupled to and extending from the first portion 6405 and configured to engage the platform.

According to some embodiments, for example as shown in FIG. 64, the positioning member 6400 may be configured to be disposed on or adjacent to the occlusal surfaces of the patient's teeth. Additionally or alternatively, the positioning member 6400 may be configured to be disposed on or adjacent other surfaces of the teeth. In some embodiments the first portion 6405 comprises a covering, such as a cap or aligner, configured to fit over the patient's teeth and having a shape specifically resembling the patient's teeth such that the positioning member 6400 is designed to fit the patient's dentition. In some embodiments, the first portion 6405 comprises an open frame, wire, or other structural member that does not cover the patient's teeth. According to several embodiments, the first portion 6405 comprises both a cover portion and an open frame portion. The positioning member 6400 may comprise any suitable material such as a plastic, a polymer, a thermoplastic, a rubber, a metal, a composite material, or the like, or combinations thereof.

The second portion 6410 of the positioning member 6400 may be configured to be temporarily coupled to the platform 6300 such that the positioning member 6400 holds the platform 6300 in a desired location and/or orientation during installation of the platform 6300 but can be removed once the platform 6300 is installed. In some embodiments, for example, the second portion 6410 includes coupling regions configured to releasably engage all or a portion of the platform 6300. The coupling regions may comprise one or more indentations at the underside of the positioning member 6400 (i.e., facing the platform) that are shaped to complement all or a portion of the shape and/or topography of the platform 6300. The indentations may provide a sufficiently tight or snug fit on all or a portion of the platform 6300, yet allow the positioning member 6400 to be removed once the platform is installed. In some embodiments, the coupling regions comprise coupling members attached to the second portion 6410 and/or other releasable fastening means.

It some cases it may be beneficial to design the positioning member 6400 such that all or a portion of the platform 6300 is visible to the clinician during installation, including the anchorage connector elements 6310. For example, all or a portion of the positioning member 6400 may be sufficiently transparent such that the platform 6300 is visible through the positioning member 6400 when coupled to the platform 6300. In these and other embodiments, the second portion 6410 of the positioning member 6400 may comprise one or more gaps or openings through which portions of the platform 6300 are visible and/or accessible by the clinician, such as the anchorage connector elements 6310. In some embodiments, for example as shown in FIG. 64, the second portion 6410 may comprise three distinct regions with gaps therebetween, each of the regions extending from the first portion 6405 to a corresponding end region that is configured to be coupled to the platform 6300. In some embodiments, the positioning member 6400 has more or fewer regions (e.g., one continuous region, two regions, four regions, etc.). The length of each of the regions of the second portions 6410 may be the same or different depending on the required placement of the platform 6300 relative to the patient's teeth and palate.

One or more portions of the second portion 6410 (including any region thereof) can have a length configured to position the platform 6300 in a desired location and desired arrangement or orientation relative to the teeth and palate. For example, referring to the positioning member 6400 and platform 6300 shown in FIG. 64, the lengths of the individual second portions 6410a, 6410b, 6410c can ensure the platform 6300 is arranged over the patient's palate such that the fasteners received through the anchorage connector elements 6310 secure the platform 6300 to the patient's palate.

The positioning member 6400 may be designed based on an oral scan of the patient's mouth and/or obtained data corresponding to an original tooth arrangement of the patient. Based on the scan and the intended appliance, the clinician or operator may determine the shape and size of the platform 6300, the shape, size, and positioning of the anchorage connector elements 6310, and/or the shape, size, and positioning of the appliance connector elements 6320. The positioning member 6400 may be formed by any suitable manufacturing process including, but not limited to molding, thermoforming, 3D printing, machining, or the like.

In use, the platform 6300 can be coupled to the positioning member 6400, for example by inserting the platform 6300 in pre-made grooves within the positioning member 6400. For example, the platform 6300 can snap into the grooves so that the platform 6300 and positioning member 6400 are temporarily connected. The positioning member and platform assembly can then be disposed over the patient's teeth such that the platform 6300 (including the anchorage connector elements 6310) is disposed at a desired location along the patient's palate. One or more fastening elements may then be used to secure the anchorage connector elements 6310 in place. With the platform 6300 secured to the patient's palate, the positioning member 6400 can be decoupled from the platform 6300 and removed from the patient's mouth. For example, the positioning member 6400 may be pulled away from the platform 6300 such that the platform 6300 is freed from the indentations of the positioning member 6400.

We claim:

1. An orthodontic appliance system comprising:
an appliance for installing on a patient's teeth, the appliance configured to extend along the surfaces of two or more adjacent teeth in a jaw of the patient when the appliance is installed, the appliance having at least one platform connector element;
an anchoring platform including an annular body for installing on the patient's maxilla or mandible, the anchoring platform having at least one appliance connector element configured to selectively connect with the at least one platform connector element of the appliance, wherein the anchoring platform further includes a plurality of anchorage connector elements extending from the annular body and configured to receive at least one temporary anchoring device (TAD) for holding the anchoring platform onto the patient's maxilla or mandible, the plurality of anchorage connector elements including one or more first anchorage connector elements extending inward from the annular body toward a central area surrounded by the annular body.

2. The system of claim 1, wherein the appliance includes at least one first rigid segment and at least one platform connector arm extending from the at least one first rigid segment, and wherein the at least one platform connector element of the appliance is provided on the at least one arm.

3. The system of claim 2, wherein the appliance includes at least one further arm extending from the at least one first rigid segment; and a bracket connector on each further arm, each bracket connector configured to selectively connect to a bracket that may be secured to a respective one of the patient's teeth.

4. The system of claim 2, wherein the appliance includes a plurality of further arms extending from the at least one first rigid segment; and a plurality of bracket connectors including a bracket connector on each further arm, each bracket connector configured to selectively connect to a bracket that may be secured to a respective one of the patient's teeth.

5. The system of claim 1, wherein the at least one platform connector element comprises at least one Y shaped member having laterally projecting end portions configured to be received within corresponding apertures of the at least one appliance connector element.

6. The system of claim 1, wherein the anchorage connector elements are configured to receive the at least one TAD for holding the anchoring platform onto the patient's maxilla.

7. The system of claim 1, wherein the anchorage connector elements are configured to receive the at least one TAD for holding the anchoring platform onto the patient's mandible.

8. The system of claim 1, wherein the plurality of anchorage connector elements further includes one or more second anchorage connector elements extending outward from the annular body toward an area outside of the annular body.

9. The system of claim 1, wherein the anchoring platform includes a plate-like body configured to be installed on the patient's mandible.

10. The system of claim 9, wherein the plate-like body of the anchoring platform further includes at least one opening through which at least one TAD may extend for holding the anchoring platform onto the patient's mandible.

11. The system of claim 10, wherein the plate-like body of the anchoring platform has a convex surface for abutting against a patient's palate and a concave surface facing opposite to the convex surface.

12. The system of claim 11, wherein the plate-like body of the anchoring platform is configured to correspond to an impression mold of the patient's palate.

13. The system of claim 11, wherein the anchoring platform further includes one or more appliance connector elements extending from the concave surface, and configured to selectively connect with the one or more platform connector elements of the appliance.

14. A method of making an orthodontic appliance system comprising:
configuring an appliance for installing on a patient's teeth, to extend along the surfaces of two or more adjacent teeth in a jaw of the patient when the appliance is installed; providing the appliance with at least one platform connector element;
configuring an anchoring platform including an annular body for installing on the patient's maxilla or mandible; providing the anchoring platform with at least one appliance connector element configured to selectively connect with the at least one platform connector element of the appliance and at least one anchorage connector element extending from the annular body and configured to receive at least one temporary anchoring device (TAD) for holding the anchoring platform onto the patient's maxilla or mandible, the at least one anchorage connector element extending inward from the annular body toward a central area surrounded by the annular body.

15. The method of claim 14, wherein configuring the appliance comprises configuring at least one first rigid segment and at least one platform connector arm extending from the at least one first rigid segment, and wherein the at least one platform connector element of the appliance is provided on the at least one arm.

16. The method of claim 15, wherein configuring the appliance comprises configuring at least one further arm extending from the at least one first rigid segment, and providing a bracket connector on each further arm, wherein each bracket connector is configured to selectively connect to a bracket that may be secured to a respective one of the patient's teeth.

17. The method of claim 14, wherein providing the anchoring platform comprises forming a plate-like body configured to be installed on the patient's mandible.

18. An orthodontic appliance system comprising:
an appliance for installing on a patient's teeth, the appliance configured to extend along two or more adjacent teeth in a jaw of the patient when the appliance is installed, the appliance having at least one platform connector element;
an anchoring platform including an annular body for installing on the patient's maxilla or mandible, the anchoring platform having at least one appliance connector element configured to selectively interlock with the at least one platform connector element of the appliance and at least one anchorage connector element extending from the annular body and configured to receive at least one temporary anchoring device (TAD) for holding the anchoring platform onto the patient's maxilla or mandible, the at least one anchorage connector element extending inward from the annular body toward a central area surrounded by the annular body.

* * * * *